(12) United States Patent
Nishimiya et al.

(10) Patent No.: US 9,371,543 B2
(45) Date of Patent: Jun. 21, 2016

(54) DNA ELEMENT HAVING THE ACTIVITY OF ENHANCING FOREIGN GENE EXPRESSION

(71) Applicant: Daiichi Sankyo Company, Limited, Chuo-ku, Tokyo (JP)

(72) Inventors: Daisuke Nishimiya, Tokyo (JP); Tatsuya Inoue, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 80 days.

(21) Appl. No.: 13/728,809

(22) Filed: Dec. 27, 2012

(65) Prior Publication Data

US 2013/0171694 A1 Jul. 4, 2013

Related U.S. Application Data

(63) Continuation of application No. PCT/JP2011/065916, filed on Jul. 6, 2011.

(30) Foreign Application Priority Data

Jul. 7, 2010 (JP) .................................. 2010-154782

(51) Int. Cl.
*C12N 15/85* (2006.01)

(52) U.S. Cl.
CPC .......... *C12N 15/85* (2013.01); *C12N 2800/107* (2013.01); *C12N 2830/46* (2013.01)

(58) Field of Classification Search
CPC ... C07H 21/04; C12N 15/85; C12N 2800/107
See application file for complete search history.

(56) References Cited

FOREIGN PATENT DOCUMENTS

| JP | 2010-154782 | * | 7/2011 | |
|---|---|---|---|---|
| WO | 89/07644 A1 | | 8/1989 | |
| WO | 2009/118137 A1 | | 10/2009 | |
| WO | WO/2013/080934 | * | 6/2013 | ............. C12N 15/09 |

OTHER PUBLICATIONS

Feng et al. (GenBank AC182841.2 Mar 18, 2006).*
Extended European Search Report mailed Dec. 16, 2013, issued in corresponding European Application No. 13 186 031.4, filed Sep. 25, 2013, 9 pages.
"*Homo sapiens* Genomic DNA, Chromosome 11q, Clone:RP11-643G5," Database EMBL Accession No. AP003400, Mar. 19, 2001, retrieved from EB Accession No. EM_STD:AP003400, <http://ibis.internal.epo.org/exam/dbfetch.jsp?id=EM_STD:AP003400>, [retrieved Nov. 28, 2013], 29 pages.
Database Genbank: *Homo sapiens* all assemblies "*Homo sapiens* chromosome 15 genomic scaffold, GRCh38 alternate locus group ALT_REF_LOCI_1 HSCHR15_5_CTG8," NCBI Reference Sequence: NT_187606.1, Feb. 3, 2014, <http://www.ncbi.nlm.nih.gov/nuccore/568815403?report=genbank&to=43088> [retrieved Aug. 21, 2014], 16 pages.

(Continued)

*Primary Examiner* — Alexander Kim
(74) *Attorney, Agent, or Firm* — Christensen O'Connor Johnson Kindness PLLC

(57) ABSTRACT

A method for stably achieving high expression of a foreign gene in mammalian cells using a novel DNA element is disclosed. More specifically, the present application discloses a DNA element which enhances the activation of transcription by changing the chromatin structure around a gene locus into which a foreign gene expression unit has been introduced.

30 Claims, 14 Drawing Sheets

(56) References Cited

OTHER PUBLICATIONS

Written Opinion mailed May 16, 2014, issued in corresponding Singapore Application No. 201209433-0, filed Jul. 6, 2011, 8 pages.

Bell, A.C., et al., "Insulators and Boundaries: Versatile Regulatory Elements in the Eukaryotic Genome," Science 291(5503):447-450, Jan. 2001.

"European Bioinformatics Institute, European Nucleotide Archive (ENA)", Sequence No. CZ458076.1, "MCF745107TF Human MCF7 Breast Cancer Cell Line Library (MCF7_1) *Homo sapiens* Genomic Clone MCF7_45I07, Genomic Survey Sequence," Database ENA [Online], Oct. 21, 2005, <http://www.ebi.ac.uk/ena/data/view/CZ458076> [retrieved Feb. 22, 2013], 3 pages.

"European Bioinformatics Institute, European Nucleotide Archive (ENA)", Sequence No. AC010724.6, "*Homo sapiens* BAC Clone RP11-152F13 From 15, Complete Sequence," Database ENA [Online], Sep. 23, 1999, <http://www.ebi.ac.uk/ena/data/view/AC010724> [retrieved Feb. 22, 2013], 6 pages.

Girod, P.A., et al., "Genome-Wide Prediction of Matrix Attachment Regions That Increase Gene Expression in Mammalian Cells," Nature Methods 4(9):747-753, Sep. 2007.

International Search Report mailed Feb. 21, 2012, issued in corresponding International Application No. PCT/JP2011/065916, filed Jul. 6, 2011, 7 pages.

Li, Q., et al., "Locus Control Regions," Blood 100(9):3077-3086, Nov. 2002.

Otte, A.P., et al., "Various Expression-Augmenting DNA Elements Benefit From Star-Select, a Novel High Stringency Selection System for Protein Expression," Biotechnology Progress 23(4):801-807, Jul.-Aug. 2007.

Volik, S., et al., "Decoding the Fine-Scale Structure of a Breast Cancer Genome and Transcriptome," Genome Research 16(3):394-404, Mar. 2006.

International Preliminary Report on Patentability mailed Jan. 8, 2013, issued in corresponding International Application No. PCT/JP2011/065916, filed Jul. 6, 2011, 11 pages.

State Intellectual Property Office of P.R. China (SIPO) First Office Action, dated Nov. 4, 2013, issued in corresponding Chinese Application No. 201180043099.8, filed Jul. 6, 2011, 4 pages.

Gorman, C., et al., "Use of MAR Elements to Increase the Production of Recombinant Proteins," in M. Al-Rubeai (ed.), "Cell Engineering," vol. 6, "Cell Line Development," Springer Science+Business Media, Berlin, 2009, pp. 1-32.

Kwaks, T.H., and A.P. Otte, "Employing Epigenetics to Augment the Expression of Therapeutic Proteins in Mammalian Cells," Trends in Biotechnology 24(3):137-142, Mar. 2006.

Williams, S., et al., "CpG-Island Fragments From the HNRPA2B1/CBX3 Genomic Locus Reduce Silencing and Enhance Transgene Expression From the hCMV Promoter/Enhancer in Mammalian Cells," BMC Biotechnology 5:17, Jun. 2005,9 pages.

Wurm, F.M., "Production of Recombinant Protein Therapeutics in Cultivated Mammalian Cells," Nature Biotechnology 22(11):1393-1398, Nov. 2004.

Alberts, B., et al., "Molecular Cell Biology," Peach Publishers, Moscow, 1994, p. 129.

Birren, B., "Homo sapiens Chromosome 11, Clone RP11-702F3, Complete Sequence," Nucleic Acid Sequence Accession No. AC024475.15, submitted to GenBank on Feb. 28, 2000, <http://www.ncbi.nlm.nih.gov/nuccore/AC024475.15> [retrieved Apr. 5, 2016], 54 pages.

Harrison, E., "Human DNA Sequence From Clone RP6-137J22 on Chromosome 1," Nucleic Acid Sequence Accession No. BX248398.9, submitted to European Nucleotide Archive on Jan. 13, 2009, <http://www.ebi.ac.uk/ena/data/view/BX248398&display=text> [retrieved Apr. 5, 2016], 38 pages.

Hattori, M., et al., "Homo sapiens Genomic DNA, Chromosome 11q, Clone RP11-643G5, Complete Sequence," \Nucleic Acid Sequence Accession No. AP0034002, submitted to GenBank on Mar. 8, 2001, <http://www.ncbi.nlmnih.gov/nuccore/15320508> [retrieved Apr. 5, 2016], 31 pages.

Makatani, Y., "Histone Acetylases—Versatile Players," Genes to Cells 6(2):79-86, Feb. 2001.

Russian Office Action mailed Dec. 9, 2015, issued in corresponding Russian Application No. 2013104989/10 (007422), filed Jul. 6, 2011, 9 pages.

Waterston, R.H., "Homo sapiens BAC Clone RP11-115A14 From 4, Complete Sequence," Nucleic Acid Sequence Accession No. AC093770.4, submitted to GenBank on Sep. 10, 2001, <http://www.ncbi.nlm.nih.gov/nuccore/AC093770> [retrieved Apr. 5, 2016], 32 pages.

Waterston, R.H., "Homo sapiens BAC Clone RP11-152F13 From 15, Complete Sequence," Nucleic Acid Sequence Accession No. AC010724.6, submitted to GenBank on Sep. 21, 1999, <http://www.ncbi.nlm.nih.gov/nuccore/AC010724> [retrieved April 5, 2016], 65 pages; Sulston, J.E., and R. Waterston, "Toward a Complete Human Genome Sequence," Genome Research (11):1097-1108, Nov. 1998.

* cited by examiner

| ID | START LOCATION | END LOCATION | LENGTH (BP) |
|---|---|---|---|
| A2 | 80966429 | 80974878 | 8450 |
| A2-1 | 80966429 | 80969428 | 3000 |
| A2-2 | 80969229 | 80972228 | 3000 |
| A2-3 | 80971829 | 80974878 | 3050 |
| A2-4 | 80967129 | 80969128 | 2000 |
| A2-5 | 80967129 | 80968628 | 1500 |
| A2-6 | 80967129 | 80970128 | 3000 |
| A2-7 | 80968429 | 80971428 | 3000 |
| A2-8 | 80970429 | 80973428 | 3000 |
| A2-9 | 80966429 | 80970128 | 3700 |
| A2-10 | 80968429 | 80972228 | 3800 |
| A2-11 | 80969229 | 80973428 | 4200 |
| A2-12 | 80967129 | 80972228 | 5100 |
| A2-13 | 80968429 | 80973428 | 5000 |
| A2-14 | 80969229 | 80974878 | 5650 |
| A2-15 | 80966429 | 80972228 | 5800 |
| A2-16 | 80967129 | 80973428 | 6300 |
| A2-17 | 80968429 | 80974878 | 6450 |

*FIG. 7.*

| ID | START LOCATION | END LOCATION | LENGTH (BP) |
|---|---|---|---|
| A7 | 88992123 | 89000542 | 8420 |
| A7-1 | 88992723 | 88995722 | 3000 |
| A7-2 | 88995723 | 89000542 | 4820 |
| A7-3 | 88997523 | 89000542 | 3020 |
| A7-4 | 88995523 | 88998522 | 3000 |
| A7-5 | 88993623 | 88996622 | 3000 |
| A7-6 | 88996523 | 88999522 | 3000 |
| A7-7 | 88994523 | 88997522 | 3000 |
| A7-8 | 88992123 | 88995722 | 3600 |
| A7-9 | 88993623 | 88997522 | 3900 |
| A7-10 | 88994523 | 88998522 | 4000 |
| A7-11 | 88995523 | 88999522 | 4000 |
| A7-12 | 88996523 | 89000542 | 4020 |
| A7-13 | 88992123 | 88997522 | 5400 |
| A7-14 | 88993623 | 88998522 | 4900 |
| A7-15 | 88994523 | 88999522 | 5000 |
| A7-16 | 88995523 | 89000542 | 5020 |
| A7-17 | 88992123 | 88998522 | 6400 |
| A7-18 | 88993623 | 88999522 | 5900 |

FIG. 9.

| ID | START LOCATION | END LOCATION | LENGTH (BP) |
|---|---|---|---|
| A18 | 111275976 | 111284450 | 8475 |
| A18-1 | 111275976 | 111281015 | 5040 |
| A18-2 | 111276976 | 111281977 | 5002 |
| A18-3 | 111277976 | 111282975 | 5000 |
| A18-4 | 111278975 | 111282975 | 4001 |

| ID | START LOCATION | END LOCATION | LENGTH (BP) |
|---|---|---|---|
| B5 | 143034684 | 143043084 | 8401 |
| B5-1 | 143034684 | 143038684 | 4001 |
| B5-2 | 143034684 | 143037883 | 3200 |
| B5-3 | 143037174 | 143040284 | 3111 |
| B5-4 | 143040056 | 143043084 | 3029 |
| B5-5 | 143035584 | 143038684 | 3101 |
| B5-6 | 143038684 | 143041683 | 3000 |

| ID | START LOCATION | END LOCATION | LENGTH (BP) |
|---|---|---|---|
| C14 | 46089056 | 46097482 | 8427 |
| C14-1 | 46090015 | 46093070 | 3056 |
| C14-2 | 46091042 | 46094069 | 3028 |
| C14-3 | 46093075 | 46096174 | 3100 |
| C14-4 | 46090015 | 46097196 | 7182 |
| C14-5 | 46090015 | 46095066 | 5052 |
| C14-6 | 46093994 | 46097196 | 3203 |
| C14-7 | 46090015 | 46094069 | 4055 |
| C14-8 | 46092049 | 46096174 | 4126 |
| C14-9 | 46093075 | 46097196 | 4122 |
| C14-10 | 46089056 | 46094069 | 5014 |
| C14-11 | 46091042 | 46096174 | 5133 |
| C14-12 | 46092049 | 46097196 | 5148 |
| C14-13 | 46090015 | 46096174 | 6160 |
| C14-14 | 46091042 | 46097196 | 6155 |

| A2 | THE START AND END POINTS ON THE BASIS OF THE FULL LENGTH SEQUENCE OF THE DNA ELEMENT A2 | |
|---|---|---|
| | START POINT | END POINT |
| A2 | 1 | 8450 |
| A2-1 | 1 | 3000 |
| A2-2 | 2801 | 5800 |
| A2-3 | 5401 | 8450 |
| A2-4 | 701 | 2700 |
| A2-5 | 701 | 2200 |
| A2-6 | 701 | 3700 |
| A2-7 | 2001 | 5000 |
| A2-8 | 4001 | 7000 |
| A2-9 | 1 | 3700 |
| A2-10 | 2001 | 5800 |
| A2-11 | 2801 | 7000 |
| A2-12 | 701 | 5800 |
| A2-13 | 2001 | 7000 |
| A2-14 | 2801 | 8450 |
| A2-15 | 1 | 5800 |
| A2-16 | 701 | 7000 |
| A2-17 | 2001 | 8450 |

| A7 | THE START AND END POINTS ON THE BASIS OF THE FULL LENGTH SEQUENCE OF THE DNA ELEMENT A7 | |
|---|---|---|
| | START POINT | END POINT |
| A7 | 1 | 8420 |
| A7-1 | 601 | 3600 |
| A7-2 | 3601 | 8420 |
| A7-3 | 5401 | 8420 |
| A7-4 | 3401 | 6400 |
| A7-5 | 1501 | 4500 |
| A7-6 | 4401 | 7400 |
| A7-7 | 2401 | 5400 |
| A7-8 | 1 | 3600 |
| A7-9 | 1501 | 5400 |
| A7-10 | 2401 | 6400 |
| A7-11 | 3401 | 7400 |
| A7-12 | 4401 | 8420 |
| A7-13 | 1 | 5400 |
| A7-14 | 1501 | 6400 |
| A7-15 | 2401 | 7400 |
| A7-16 | 3401 | 8420 |
| A7-17 | 1 | 6400 |
| A7-18 | 1501 | 7400 |

| A18 | THE START AND END POINTS ON THE BASIS OF THE FULL LENGTH SEQUENCE OF THE DNA ELEMENT A18 | |
|---|---|---|
| | START POINT | END POINT |
| A18 | 1 | 8475 |
| A18-1 | 1 | 5040 |
| A18-2 | 1001 | 6002 |
| A18-3 | 2001 | 7000 |
| A18-4 | 3000 | 7000 |

FIG. 19.

| | THE START AND END POINTS ON THE BASIS OF THE FULL LENGTH SEQUENCE OF THE DNA ELEMENT B5 | |
|---|---|---|
| | START POINT | END POINT |
| B5 | 1 | 8401 |
| B5-1 | 1 | 4001 |
| B5-2 | 1 | 3200 |
| B5-3 | 2491 | 5601 |
| B5-4 | 5373 | 8401 |
| B5-5 | 901 | 4001 |
| B5-6 | 4001 | 7000 |

| | THE START AND END POINTS ON THE BASIS OF THE FULL LENGTH SEQUENCE OF THE DNA ELEMENT C14 | |
|---|---|---|
| | START POINT | END POINT |
| C14 | 1 | 8427 |
| C14-1 | 960 | 4015 |
| C14-2 | 1987 | 5014 |
| C14-3 | 4020 | 7119 |
| C14-4 | 960 | 8141 |
| C14-5 | 960 | 6011 |
| C14-6 | 4939 | 8141 |
| C14-7 | 960 | 5014 |
| C14-8 | 2994 | 7119 |
| C14-9 | 4020 | 8141 |
| C14-10 | 1 | 5014 |
| C14-11 | 1987 | 7119 |
| C14-12 | 2994 | 8141 |
| C14-13 | 960 | 7119 |
| C14-14 | 1987 | 8141 |

DNA ELEMENT HAVING THE ACTIVITY OF ENHANCING FOREIGN GENE EXPRESSION

CROSS-REFERENCE TO RELATED APPLICATION

This application is a continuation of the National Stage of International Application No. PCT/JP2011/065916, filed Jul. 6, 2011, the disclosure of which is incorporated by reference herein.

STATEMENT REGARDING SEQUENCE LISTING

The sequence listing associated with this application is provided in text format in lieu of a paper copy and is hereby incorporated by reference into the specification. The name of the text file containing the sequence listing is 40304_Seq_Amend_Final_2014-12-10.txt. The text file is 80 KB; was created on Dec. 10, 2014 and is being submitted via EFS-Web with the filing of the specification.

TECHNICAL FIELD

The present invention relates to a transformed mammalian host cell whose ability to secrete a foreign protein has been enhanced by using a foreign gene expression vector having a DNA element and a method for producing the foreign protein using the host cell.

BACKGROUND ART

Due to the development of genetic recombination techniques, the market for protein pharmaceutical products such as therapeutic proteins and antibody drugs has rapidly expanded. In particular, antibody drugs have high specificity and do not cause an adverse immunoreaction even if they are administered to the human body, and therefore, the development thereof has been actively performed.

As a host cell in which a protein pharmaceutical typified by an antibody drug is produced, a microorganism, a yeast, an insect, an animal or plant cell, a transgenic animal or plant cell, or the like can be used. In order for the protein pharmaceutical to have biological activity or immunogenicity, post-translational modification such as folding or glycosylation is essential, and therefore a microorganism with which complicated post-translational modification cannot be performed or a plant having a different glycan structure is not suitable as a host cell operating as a bioreactor. The use of a cultured mammalian cell such as a CHO cell which is from a species closely related to humans is currently standard considering that such a cell has a glycan structure similar to that of humans and is safe, and post-translational modification can be performed using such a cell.

In cases where a cultured mammalian cell is used as a host cell, there are the problems that the growth rate is low, the productivity is low, the cost is high, etc., as compared with a microorganism or the like (see Non-Patent Document 1). In addition, in order to use a protein pharmaceutical product in a clinical trial, it is necessary to administer a large amount of the product. Therefore, the lack of production ability thereof is also a worldwide problem. Accordingly, in order to improve the productivity of a foreign gene in a cultured mammalian cell, a lot of studies of promoters, enhancers, drug selection markers, gene amplification and culturing engineering techniques, and the like have been performed so far. However, the current situation is that a system capable of uniformly increasing gene expression has not yet been established. As one of the causes of the low productivity of a foreign protein, a "position effect" is considered (see Non-Patent Document 2). When a foreign gene is introduced into a host cell, it is randomly integrated into the host chromosomal genome, and the transcription of the foreign gene is greatly affected by DNA around the region where the foreign gene has been integrated. A position effect is affected by factors such as the insertion site, copy number, structure, etc., of the foreign gene, however, it is very difficult to control the insertion site in the chromosome.

In order to solve the problem, regulatory polynucleotide sequences (also known as DNA elements) such as a locus control region (LCR), a scaffold/matrix attachment region (S/MAR), an insulator, a ubiquitous chromatin opening element (UCOE), and an anti-repressor (STAR element) have recently been identified (see Non-Patent Documents 3 to 6). LCR is not required to open the chromatin structure at an endogenous gene locus. However, LCR is a transcription regulatory element having an ability to open the chromatin structure around the DNA where the foreign gene has been integrated and to remodel a wide range of chromatin when it is used along with a foreign gene expression unit, and is said to require an AT-rich region (see Non-Patent Document 7).

The above-mentioned DNA element typified by LCR is often used in combination with a promoter, and it is known that in cases where a DNA element is used in combination with a promoter, the expression level of a foreign gene is increased as compared with cases where only the promoter is used. However, very few types of DNA elements have been reported so far, and the various mechanisms contributing to the enhancement of foreign gene expression are different from one another. Further, even if a DNA element and a promoter are used in combination, sufficient amounts of a therapeutic protein under the control of the DNA element and the promoter are not produced. Therefore, it cannot be said that sufficient knowledge of a DNA element capable of increasing the productivity of a foreign protein has been obtained.

Accordingly, an object of the invention is to provide a method for increasing the production of a foreign protein to be used in a protein pharmaceutical product using a DNA element having high activity in enhancing foreign gene expression in a host cell such as a cultured mammalian cell.

CITATION LIST

Non Patent Literature

NPL 1: Florian M. Wurm. (2004) Production of recombinant protein therapeutics in cultivated mammalian cells. Nat. Biotechnol. 22(11): 1393-1398

NPL 2: Ted H. J. Kwaks and Arie P. Otte. (2006) Employing epigenetics to augment the expression of therapeutic proteins in mammalian cells. TRENDS in Biotechnol. 24(3): 137-142

NPL 3: Pierre-Alain Girod, Duc-Quang Nguyen. et al. (2007) Genome-wide prediction of matrix attachment regions that increase gene expression in mammalian cells. Nat. Methods. 4(9): 747-753

NPL 4: Adam C. Bell, Adam G. West, Gary Felsenfeld (2001) Insulators and Boundaries: Versatile Regulatory Elements in the Eukaryotic Genome, Science 291: 447-450

NPL 5: Steven Williams, Tracey Mustoe. et al. (2005) CpG-island fragments from the HNRPA2B1/CBX3 genomic locus reduce silencing and enhance transgene expression from the hCMV promoter/enhancer in mammalian cells. BMC Biotechnol. 5(17): 1-9
NPL 6: Arie P. Otte, Ted H. J. Kwaks. et al. (2007) Various Expression-Augmenting DNA Elements Benefit from STAR-Select, a Novel High Stringency Selection System for Protein Expression. Biotechnol. Prog. 23: 801-807
NPL 7: Qiliang Li, Kenneth R. Peterson, Xiangdong Fang, and George Stamatoyannopoulos, (2002) Locus control regions, Blood 100(9): 3077-3086

SUMMARY OF INVENTION

Technical Problems

As described above, there are still not many types of DNA elements which are regulatory polynucleotide sequences, and, further, there are very few DNA elements among them that are highly effective in enhancing foreign gene expression. An object of the invention is to provide a method for stably achieving high expression in a mammalian cell using a DNA element which enhances the activation of transcription by being accompanied by a change in chromatin structure around a gene locus into which a foreign gene expression unit has been introduced, etc.

Solution to Problem

The present inventors made intensive studies in order to solve the above problems, and as a result, they found that the productivity and secretion of a foreign protein which is to be expressed can be improved by using one or more specific types of DNA elements in a cultured mammalian cell, and thus, completed the invention.

That is, the invention includes the following inventions.

(1) A polynucleotide consisting of a polynucleotide sequence represented by SEQ ID NO: 1 in the Sequence Listing.

(2) A polynucleotide consisting of a polynucleotide sequence represented by SEQ ID NO: 2 in the Sequence Listing.

(3) A polynucleotide consisting of a polynucleotide sequence represented by SEQ ID NO: 3 in the Sequence Listing.

(4) A polynucleotide consisting of a polynucleotide sequence represented by SEQ ID NO: 4 in the Sequence Listing.

(5) A polynucleotide consisting of a polynucleotide sequence represented by SEQ ID NO: 5 in the Sequence Listing.

(6) A polynucleotide comprising at least 3000 consecutive nucleotides of a polynucleotide sequence represented by any one of SEQ ID NOS: 1 to 5 in the Sequence Listing.

(7) A polynucleotide comprising at least 2000 consecutive nucleotides of a polynucleotide sequence represented by any one of SEQ ID NOS: 1 to 5 in the Sequence Listing.

(8) A polynucleotide comprising at least 1500 consecutive nucleotides of a polynucleotide sequence represented by any one of SEQ ID NOS: 1 to 5 in the Sequence Listing.

(9) A polynucleotide consisting of a polynucleotide sequence having a homology of 95% or more to the polynucleotide sequence of the polynucleotide according to any one of (1) to (8).

(10) A polynucleotide consisting of a polynucleotide sequence having a homology of 99% or more to the polynucleotide sequence of the polynucleotide according to any one of (1) to (8).

(11) A polynucleotide consisting of a polynucleotide sequence containing two or more sequences of the polynucleotide sequence of the polynucleotide according to any one of (1) to (10).

(12) A polynucleotide consisting of two or more types of polynucleotides selected from the polynucleotides according to any one of (1) to (10).

(13) A foreign gene expression vector comprising the polynucleotide sequence of a polynucleotide according to any one of (1) to (12).

(14) The foreign gene expression vector according to (13), wherein the protein encoded by the foreign gene is a multimeric protein.

(15) The foreign gene expression vector according to (14), wherein the protein encoded by the foreign gene is a hetero-multimeric protein.

(16) The foreign gene expression vector according to (15), wherein the protein encoded by the foreign gene is an antibody or a functional fragment thereof.

(17) A transformed cell into which the foreign gene expression vector according to any one of (13) to (16) has been introduced.

(18) The transformed cell according to (17), wherein the cell is a cultured cell derived from a mammal.

(19) The transformed cell according to (18), wherein the cultured cell derived from a mammal is a cell selected from the group consisting of COS-1 cells, 293 cells, and CHO cells.

(20) The transformed cell according to any one of (17) to (18), wherein the protein encoded by the foreign gene is a multimeric protein.

(21) The transformed cell according to (20), wherein the protein encoded by the foreign gene is a hetero-multimeric protein.

(22) The transformed cell according to (21), wherein the protein encoded by the foreign gene is an antibody or a functional fragment thereof.

(23) A method for producing a protein characterized by comprising culturing the transformed cell according to any one of (17) to (22) and obtaining the protein encoded by the foreign gene from the resulting culture product.

(24) A method for enhancing foreign gene expression in a transformed cell into which a foreign gene or a foreign gene expression vector has been introduced, characterized by using a polynucleotide according to any one of (1) to (12) or a foreign gene expression vector according to any one of (13) to (16).

(25) Use of the polynucleotide according to any one of (1) to (12) for enhancing foreign gene expression in a transformed cell.

Advantageous Effects of Invention

According to the invention, by introducing a foreign gene expression vector using a DNA element into a mammalian host cell, the expression of a foreign gene for a therapeutic protein, an antibody, or the like can be significantly enhanced.

BRIEF DESCRIPTION OF DRAWINGS

FIG. 7 is a table showing the sequence lengths of DNA element A2 and related sequences.

FIG. 4A through FIG. 8C comprise three graphs showing the expression of SEAP in a stably expressing CHO cell line either without a DNA element or with DNA element A2 or a related sequence.

FIG. 9 is a table showing the sequence lengths of DNA element A7 and related sequences.

FIG. 10A (A7-1-A7-7), FIG. 10B (A7-8-A7-12), and FIG. 10C (A7-13-A7-18). The effects of DNA element A7 and related sequences on enhancement of expression were confirmed.

FIG. 15 is a table showing the sequence lengths of DNA element C14 and related sequences.

FIG. 16A (C14-1-C14-6), FIG. 16B (C14-7-C14-9), and FIG. 16C (C14-10-C14-14). The effects of DNA element C14 and related sequences on enhancement of expression were confirmed.

FIG. 18 is a view showing nucleotides at the starting and end points on the basis of the full-length sequence of a DNA element A2, A7, or A18.

FIG. 19 is a view showing nucleotides at the starting and end points on the basis of the full-length sequence of a DNA element B5 or C14.

DESCRIPTION OF EMBODIMENTS

Figure 1:
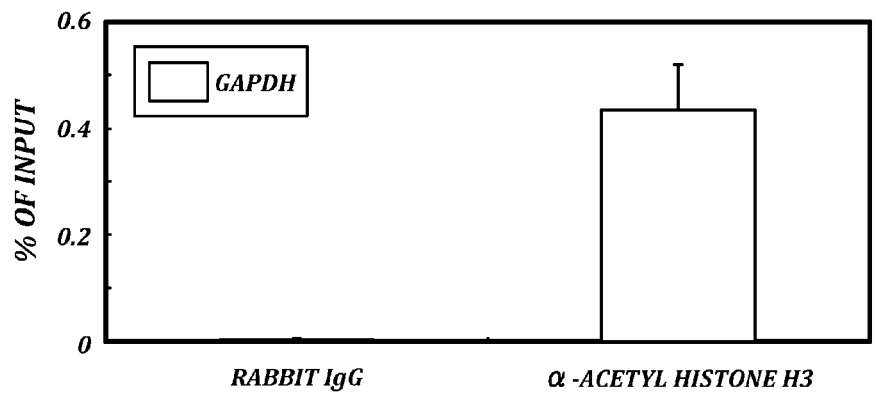
FIG. 1 shows a graph in which it was confirmed by the amplification of a GAPDH region that a sample subjected to ChIP-on-chip was chromatin-immunoprecipitated specifically with an anti-acetylated histone H3 antibody.

Hereinafter, the invention will be specifically described with reference to the Examples. However, these Examples do not limit the technical scope of the invention. The plasmids, restriction enzymes, DNA modification enzymes, and the like to be used in the Examples of the invention are commercially available products and can be used according to common procedures. Further, procedures used for DNA cloning, polynucleotide sequence determination, transformation of a host cell, culturing of a transformed host cell, isolation of an antibody from an obtained culture solution, purification of an antibody, and the like are also well known to those skilled in the art or are available from the literature.

The term "gene" as used herein includes not only DNA, but also mRNA thereof, cDNA, and RNA thereof.

The term "polynucleotide" as used herein is used in the same meaning as a nucleic acid and also includes DNA, RNA, probes, oligonucleotides, and primers.

The terms "polypeptide" and "protein" as used herein are used without distinction.

The term "gene expression" as used herein refers to a phenomenon in which an mRNA is transcribed from a gene and/or a phenomenon in which a protein is translated from the mRNA.

The term "foreign gene" as used herein refers to a gene which is artificially introduced into a host cell.

The term "foreign protein" as used herein refers to a protein encoded by a foreign gene.

The term "gene expression unit" as used herein refers to a polynucleotide having, in the direction of the reading frame of transcription, at least a promoter region, a foreign gene, and a transcription terminator region (poly(A) addition signal).

The term "activity of enhancing foreign gene expression" as used herein refers to the activity of enhancing the production of a foreign protein in a host cell by creating an environment advantageous to transcription and translation for DNA around a gene expression unit containing a foreign gene and significantly improving the transcription and translation efficiency.

The term "DNA element" as used herein refers to a polynucleotide having an activity of enhancing foreign gene expression in cases where the polynucleotide is located in the vicinity of a gene expression unit or in a foreign gene expression vector containing a gene expression unit.

The term "functional fragment of an antibody" as used herein refers to a partial fragment of an antibody having antigen-binding activity and includes Fab, F(ab')$_2$, and the like. However, the term is not limited to these molecules as long as the fragment has a binding affinity for an antigen.

1. DNA Element to be Used for Enhancing Foreign Gene Expression

As shown in Example 1, a DNA element according to the invention can be obtained by using the interaction between acetylated histone H3 and genomic DNA. In general, it is said that the acetylation of histones (H3 and H4) is associated with the activation of transcription, and two main theories have been advocated. One theory is that the acetylation of histones is associated with a change in nucleosome conformation in such a manner that histone tails are acetylated, thereby being electrically neutralized, resulting in weakening of DNA-histone interactions (Mellor J. (2006) Dynamic nucleosomes and gene transcription. Trends Genet. 22(6): 320-329). The other theory is that the acetylation of histones is associated with the recruitment of various transcription factors (Nakatani Y. (2001) Histone acetylases—versatile players. Genes Cells. 6(2): 79-86). In either theory, there is a high possibility that the acetylation of histones is associated with the activation of transcription, and by performing chromatin immunoprecipitation (ChIP) using an anti-acetylated histone H3 antibody, it is possible to concentrate a DNA element interacting with acetylated histone H3.

In the present invention, A2 is an example of a DNA element to be used for enhancing foreign gene expression. A2 is located in the region from 80966429 to 80974878 of human chromosome 15 and is a polynucleotide sequence of 8450 bp, having an AT content of 62.2%. The polynucleotide sequence of A2 is represented by SEQ ID NO: 1 in the Sequence Listing.

A7, A18, B5, and C14 are examples of similar DNA elements. A7 is located in the region from 88992123 to 89000542 of human chromosome 11 and is a polynucleotide sequence of 8420 bp, having an AT content of 64.52%. The polynucleotide sequence of A7 is represented by SEQ ID NO: 2 in the Sequence Listing.

A18 is located in the region from Ser. No. 11/275,976 to Ser. No. 11/284,450 of human chromosome 4 and is a polynucleotide sequence of 8475 bp, having an AT content of 62.54%. The polynucleotide sequence of A18 is represented by SEQ ID NO: 3 in the Sequence Listing.

B5 is located in the region from 143034684 to 143043084 of human chromosome 1 and is a polynucleotide sequence of 8401 bp, having an AT content of 66.37%. The polynucleotide sequence of B5 is represented by SEQ ID NO: 4 in the Sequence Listing.

Finally, C14 is located in the region from 46089056 to 46097482 of human chromosome 11 and is a polynucleotide sequence of 8427 bp, having an AT content of 63.81%. The polynucleotide sequence of C14 is represented by SEQ ID NO: 5 in the Sequence Listing.

In the invention, the activity of enhancing foreign gene expression of the DNA element can be assayed by using the activity of a protein encoded by a reporter gene such as SEAP as an index. In cases where the activity of a reporter protein in the presence of the DNA element is increased, preferably by two times or more, more preferably four times or more, even more preferably five times or more as compared with the case where the DNA element is not present, the DNA element can be determined to have an activity of enhancing foreign gene expression. Even in cases where the activity is increased by two times or more, it is expected that this will reduce the cell culture scale and the cell culture time, and as a result, it is possible to increase the yield and reduce the cell culture cost. If the yield is increased, then it is possible to supply stably a foreign protein to be used as a pharmaceutical. In addition, if the cell culture cost is reduced, the cost for the foreign protein to be used as a pharmaceutical is reduced, and the financial burden on patients to whom the foreign protein is to be administered is also reduced.

In the invention, any one of the above DNA elements may be used alone, and two or more copies of one type of the DNA element may be used. Alternatively, two or more different types of the above DNA elements may be used in combination.

A2, A7, A18, B5, and C14 are preferred examples of the DNA element to be used in the invention.

The DNA element to be used in the invention may be a polynucleotide sequence which comprises a polynucleotide sequence having a homology of 80% or more to any of the polynucleotide sequences represented by SEQ ID NOS: 1 to 5 and has an activity of enhancing foreign gene expression. The homology of 80% or more is preferably a homology of 90% or more, more preferably a homology of 95% or more, most preferably a homology of 99% or more. The polynucleotide sequence homology search can be performed in, for example, the DNA Databank of Japan or the like using a program such as FASTA or BLAST.

The DNA element to be used in the invention may be a DNA element which hybridizes to a polynucleotide consisting of a polynucleotide sequence complementary to a polynucleotide consisting of a polynucleotide sequence selected from the group consisting of the polynucleotide sequences represented by SEQ ID NOS: 1 to 5 under stringent conditions and has an activity of enhancing foreign gene expression.

The term "stringent conditions" as used herein refers to conditions in which a so-called specific hybrid is formed but a non-specific hybrid is not formed. For example, conditions in which a complementary strand of a nucleic acid consisting of a polynucleotide sequence having a high homology, i.e., a polynucleotide sequence having a homology of 80% or more, preferably 90% or more, more preferably 95% or more, most preferably 99% or more to a polynucleotide sequence selected from the group consisting of the polynucleotide sequences represented by SEQ ID NOS: 1 to 5 hybridizes, and a complementary strand of a nucleic acid comprising a polynucleotide sequence having a lower homology does not hybridize are exemplary stringent conditions. To be more specific, conditions in which the concentration of sodium salt is from 15 to 750 mM, preferably from 50 to 750 mM, more preferably from 300 to 750 mM, the temperature is from 25 to 70° C., preferably from 50 to 70° C., more preferably from 55 to 65° C., and the concentration of formamide is from 0 to 50%, preferably from 20 to 50%, more preferably from 35 to 45% can be exemplified. Further, as the stringent conditions, conditions for washing a filter after hybridization in which the concentration of sodium salt is generally from 15 to 600 mM, preferably from 50 to 600 mM, more preferably from 300 to 600 mM, and the temperature is from 50 to 70° C., preferably from 55 to 70° C., more preferably from 60 to 65° C. can be exemplified.

A person skilled in the art can easily obtain such a homologue gene with reference to Molecular Cloning (Sambrook, J. et al., Molecular Cloning: a Laboratory Manual 2nd ed., Cold Spring Harbor Laboratory Press, 10 Skyline Drive Plainview, N.Y. (1989)) or the like. Further, the homology of the above-mentioned polynucleotide sequence can be determined by a FASTA search or BLAST search in the same manner.

Introduction of a mutation (deletion, substitution, and/or addition) into the above-mentioned polynucleotide sequence can be performed by a method known in this technical field such as a Kunkel method or a gapped duplex method, or based on this method. For example, a mutation introduction kit utilizing a site-directed mutagenesis method (for example, Mutant-K (manufactured by TaKaRa Bio, Inc.), Mutant-G (manufactured by TaKaRa Bio, Inc.), or a LA PCR in vitro Mutagenesis series kit (manufactured by TaKaRa Bio, Inc.)), or the like can be used. Such a mutated polynucleotide can also be used as the DNA element of the invention.

As the DNA element of the invention, a partial fragment comprising at least 3000 or at least 2000 consecutive nucleotides of a polynucleotide sequence represented by any one of SEQ ID NOS: 1 to 5 in the Sequence Listing can be used. Examples of such a partial fragment include: A2-1 to A2-17 which are partial fragments of A2; A7-1 to A7-18 which are partial fragments of A7; A18-1 to A18-4 which are partial fragments of A18; B5-1 to B5-6 which are partial fragments of B5; and C14-1 to C14-14 which are partial fragments of C14. However, the DNA element is not limited to these partial fragments as long as it has an activity of enhancing foreign gene expression.

In the invention, any one of the above partial fragments may be used alone, and also two or more copies of one type of the partial fragment may be used. Alternatively, two or more different types of the partial fragments may be used in combination. Further, a full-length sequence and a partial fragment of any of the above-mentioned DNA elements may be used in combination. In the above combination, the full-length sequence and the partial fragment may be derived from the same DNA element or from different DNA elements.

As for the polynucleotide sequences of the respective fragments of A2, A2-1 corresponds to the polynucleotide sequence of nucleotides 1 to 3000 of SEQ ID NO: 1 in the Sequence Listing; A2-2 corresponds to the polynucleotide sequence of nucleotides 2801 to 5800 of SEQ ID NO: 1 in the Sequence Listing; A2-3 corresponds to the polynucleotide sequence of nucleotides 5401 to 8450 of SEQ ID NO: 1 in the Sequence Listing; A2-4 corresponds to the polynucleotide sequence of nucleotides 701 to 2700 of SEQ ID NO: 1 in the Sequence Listing; A2-5 corresponds to the polynucleotide sequence of nucleotides 701 to 2200 of SEQ ID NO: 1 in the Sequence Listing; A2-6 corresponds to the polynucleotide sequence of nucleotides 701 to 3700 of SEQ ID NO: 1 in the Sequence Listing; A2-7 corresponds to the polynucleotide sequence of nucleotides 2001 to 5000 of SEQ ID NO: 1 in the Sequence Listing; A2-8 corresponds to the polynucleotide sequence of nucleotides 4001 to 7000 of SEQ ID NO: 1 in the Sequence Listing; A2-9 corresponds to the polynucleotide sequence of nucleotides 1 to 3700 of SEQ ID NO: 1 in the Sequence Listing; A2-10 corresponds to the polynucleotide sequence of nucleotides 2001 to 5800 of SEQ ID NO: 1 in the Sequence Listing; A2-11 corresponds to the polynucleotide sequence of nucleotides 2801 to 7000 of SEQ ID NO: 1 in the Sequence Listing; A2-12 corresponds to the polynucleotide sequence of nucleotides 701 to 5800 of SEQ ID NO: 1 in the Sequence Listing; A2-13 corresponds to the polynucleotide sequence of nucleotides 2001 to 7000 of SEQ ID NO: 1 in the Sequence Listing; A2-14 corresponds to the polynucleotide sequence of nucleotides 2801 to 8450 of SEQ ID NO: 1 in the Sequence Listing; A2-15 corresponds to the polynucleotide sequence of nucleotides 1 to 5800 of SEQ ID NO: 1 in the Sequence Listing; A2-16 corresponds to the polynucleotide sequence of nucleotides 701 to 7000 of SEQ ID NO: 1 in the Sequence Listing; and A2-17 corresponds to the polynucleotide sequence of nucleotides 2001 to 8450 of SEQ ID NO: 1 in the Sequence Listing.

As for the polynucleotide sequences of the respective fragments of A7, A7-1 corresponds to the polynucleotide sequence of nucleotides 601 to 3600 of SEQ ID NO: 2 in the Sequence Listing; A7-2 corresponds to the polynucleotide sequence of nucleotides 3601 to 8420 of SEQ ID NO: 2 in the Sequence Listing; A7-3 corresponds to the polynucleotide sequence of nucleotides 5401 to 8420 of SEQ ID NO: 2 in the Sequence Listing; A7-4 corresponds to the polynucleotide sequence of nucleotides 3401 to 6400 of SEQ ID NO: 2 in the Sequence Listing; A7-5 corresponds to the polynucleotide sequence of nucleotides 1501 to 4500 of SEQ ID NO: 2 in the Sequence Listing; A7-6 corresponds to the polynucleotide sequence of nucleotides 4401 to 7400 of SEQ ID NO: 2 in the Sequence Listing; A7-7 corresponds to the polynucleotide sequence of nucleotides 2401 to 5400 of SEQ ID NO: 2 in the Sequence Listing; A7-8 corresponds to the polynucleotide sequence of nucleotides 1 to 3600 of SEQ ID NO: 2 in the Sequence Listing; A7-9 corresponds to the polynucleotide sequence of nucleotides 1501 to 5400 of SEQ ID NO: 2 in the Sequence Listing; A7-10 corresponds to the polynucleotide sequence of nucleotides 2401 to 6400 of SEQ ID NO: 2 in the Sequence Listing; A7-11 corresponds to the polynucleotide sequence of nucleotides 3401 to 7400 of SEQ ID NO: 2 in the Sequence Listing; A7-12 corresponds to the polynucleotide sequence of nucleotides 4401 to 8420 of SEQ ID NO: 2 in the Sequence Listing; A7-13 corresponds to the polynucleotide sequence of nucleotides 1 to 5400 of SEQ ID NO: 2 in the Sequence Listing; A7-14 corresponds to the polynucleotide sequence of nucleotides 1501 to 6400 of SEQ ID NO: 2 in the Sequence Listing; A7-15 corresponds to the polynucleotide sequence of nucleotides 2401 to 7400 of SEQ ID NO: 2 in the Sequence Listing; A7-16 corresponds to the polynucleotide sequence of nucleotides 3401 to 8420 of SEQ ID NO: 2 in the Sequence Listing; A7-17 corresponds to the polynucleotide sequence of nucleotides 1 to 6400 of SEQ ID NO: 2 in the Sequence Listing; and A7-18 corresponds to the polynucleotide sequence of nucleotides 1501 to 7400 of SEQ ID NO: 2 in the Sequence Listing.

As for the polynucleotide sequences of the respective fragments of A18, A18-1 corresponds to the polynucleotide sequence of nucleotides 1 to 5040 of SEQ ID NO: 3 in the Sequence Listing; A18-2 corresponds to the polynucleotide sequence of nucleotides 1001 to 6002 of SEQ ID NO: 3 in the Sequence Listing; A18-3 corresponds to the polynucleotide sequence of nucleotides 2001 to 7000 of SEQ ID NO: 3 in the Sequence Listing; and A18-4 corresponds to the polynucleotide sequence of nucleotides 3000 to 7000 of SEQ ID NO: 3 in the Sequence Listing.

The start and end points of the respective fragments of A2, A7 and A18 are also set forth in FIG. 18.

As for the polynucleotide sequences of the respective fragments of B5, B5-1 corresponds to the polynucleotide sequence of nucleotides 1 to 4001 of SEQ ID NO: 4 in the Sequence Listing; B5-2 corresponds to the polynucleotide sequence of nucleotides 1 to 3200 of SEQ ID NO: 4 in the Sequence Listing; B5-3 corresponds to the polynucleotide sequence of nucleotides 2491 to 5601 of SEQ ID NO: 4 in the Sequence Listing; B5-4 corresponds to the polynucleotide sequence of nucleotides 5373 to 8401 of SEQ ID NO: 4 in the Sequence Listing; B5-5 corresponds to the polynucleotide sequence of nucleotides 901 to 4001 of SEQ ID NO: 4 in the Sequence Listing; and B5-6 corresponds to the polynucleotide sequence of nucleotides 4001 to 7000 of SEQ ID NO: 4 in the Sequence Listing.

As for the polynucleotide sequences of the respective fragments of C14, C14-1 corresponds to the polynucleotide sequence of nucleotides 960 to 4015 of SEQ ID NO: 5 in the Sequence Listing; C14-2 corresponds to the polynucleotide sequence of nucleotides 1987 to 5014 of SEQ ID NO: 5 in the Sequence Listing; C14-3 corresponds to the polynucleotide sequence of nucleotides 4020 to 7119 of SEQ ID NO: 5 in the Sequence Listing; C14-4 corresponds to the polynucleotide sequence of nucleotides 960 to 8141 of SEQ ID NO: 5 in the Sequence Listing; C14-5 corresponds to the polynucleotide sequence of nucleotides 960 to 6011 of SEQ ID NO: 5 in the Sequence Listing; C14-6 corresponds to the polynucleotide sequence of nucleotides 4939 to 8141 of SEQ ID NO: 5 in the Sequence Listing; C14-7 corresponds to the polynucleotide sequence of nucleotides 960 to 5014 of SEQ ID NO: 5 in the Sequence Listing; C14-8 corresponds to the polynucleotide sequence of nucleotides 2994 to 7119 of SEQ ID NO: 5 in the Sequence Listing; C14-9 corresponds to the polynucleotide sequence of nucleotides 4020 to 8141 of SEQ ID NO: 5 in the Sequence Listing; C14-10 corresponds to the polynucleotide sequence of nucleotides 1 to 5014 of SEQ ID NO: 5 in the Sequence Listing; C14-11 corresponds to the polynucleotide sequence of nucleotides 1987 to 7119 of SEQ ID NO: 5 in the Sequence Listing; C14-12 corresponds to the polynucleotide sequence of nucleotides 2994 to 8141 of SEQ ID NO: 5 in the Sequence Listing; C14-13 corresponds to the polynucleotide sequence of nucleotides 960 to 7119 of SEQ ID NO: 5 in the Sequence Listing; and C14-14 corresponds to the polynucleotide sequence of nucleotides 1987 to 8141 of SEQ ID NO: 5 in the Sequence Listing.

The start and end points of the respective fragments of B5 and C14 are also set forth in FIG. 19.

2. Acquisition of Polynucleotide

In the invention, a polynucleotide containing a foreign gene encoding a foreign protein the production of which is to be increased, which will be described later, can be obtained by common procedures as described below. For example, such a polynucleotide can be isolated by screening a cDNA library derived from cells or tissues expressing the foreign gene using a DNA probe synthesized by being based on a fragment of the foreign gene. mRNA can be prepared by methods commonly used in this technical field. For example, the cells or tissues are treated with a guanidine reagent, a phenol reagent, etc., thereby obtaining total RNA, and thereafter, poly(A)+RNA (mRNA) is obtained by an affinity column method using an oligo(dT) cellulose column or a poly U-Sepharose column containing Sepharose 2B as a carrier, or the like, or by a batch method. Also, the poly(A)+RNA may further be fractionated by sucrose density-gradient centrifugation or the like. Then, a single-stranded cDNA is synthesized using the thus obtained mRNA as a template, and also using oligo dT primers and a reverse transcriptase. From the thus obtained single-stranded cDNA, a double-stranded cDNA is synthesized using DNA polymerase I, DNA ligase, RNase H, and the like. The thus synthesized double-stranded cDNA is blunted using T4 DNA polymerase, followed by ligation to an adapter (such as EcoRI adapter), phosphorylation, and the like, and the resulting DNA is incorporated into a lambda phage such as λgt11 to achieve in vivo packaging, whereby a cDNA library can be prepared. It is also possible to prepare a cDNA library using a plasmid vector other than lambda phages. Thereafter, a clone containing a target DNA (a positive clone) may be selected from the cDNA library.

In cases where the above-mentioned DNA element to be used for increasing the production of a protein or a polynucleotide containing a foreign gene is isolated from genomic DNA, or a polynucleotide containing promoter and terminator regions is isolated from genomic DNA, according to a common procedure (Molecular Cloning (1989), Methods in Enzymology 194 (1991)), genomic DNA is extracted from a cell line of an organism to be used as a collection source, and a polynucleotide is selected and isolated. The extraction of genomic DNA can be performed according to, for example, the method of Cryer et al. (Methods in Cell Biology, 12, 39-44 (1975)) or the method of P. Philippsen et al. (Methods Enzymol., 194, 169-182 (1991)).

The target DNA element or the polynucleotide containing a foreign gene can also be obtained by, for example, the PCR method (PCR Technology. Henry A. Erlich, Atockton press (1989)). In the amplification of a polynucleotide using the PCR method, 20- to 30-mer synthetic single-stranded DNAs are used as primers and genomic DNA is used as a template. The amplified gene is used after the polynucleotide sequence of the gene is confirmed. As the template for PCR, a genomic DNA library such as a bacterial artificial chromosome (BAC) can be used.

On the other hand, the polynucleotide containing a foreign gene whose sequence is not known can be obtained by (a) preparing a gene library according to a common procedure, and (b) selecting a desired polynucleotide from the prepared gene library and amplifying the polynucleotide. The gene library can be prepared by partially digesting chromosomal DNA obtained by a common procedure from a cell line of an organism to be used as a collection source using an appropriate restriction enzyme to fragment the chromosomal DNA, ligating the obtained fragments to an appropriate vector, and introducing the vector into an appropriate host. The gene library can also be prepared by extracting mRNA from the cells, synthesizing cDNA from the mRNA, ligating the cDNA to an appropriate vector, and introducing the vector into an appropriate host. As the vector to be used in such preparation, a plasmid generally known as a vector for gene library preparation, a phage vector, a cosmid, or the like can also be used. As the host to be transformed or transfected, a host suitable for the type of the above-mentioned vector may be used. The polynucleotide containing the foreign gene is selected from the above-mentioned gene library by a colony hybridization method, a plaque hybridization method, or the like using a labeled probe containing a sequence specific for the foreign gene.

Further, the polynucleotide containing the foreign gene can also be produced by total chemical synthesis. For example, the gene can be synthesized by a method in which two pairs of complementary oligonucleotides are prepared and annealed, a method in which several annealed DNA strands are ligated by a DNA ligase, a method in which several partially complementary polynucleotides are prepared and gaps are filled by PCR, or the like.

The determination of a polynucleotide sequence can be performed by a conventional technique, for example, a dideoxy method (Sanger et al., Proc. Natl. Acad. Sci., USA, 74, 5463-5467, (1977)), or the like. Further, the above determination of a polynucleotide sequence can also be easily performed using a commercially available sequencing kit or the like.

3. Foreign Gene Expression Vector, Element Vector

As a foreign gene expression vector of the invention, a vector containing one type of the above-mentioned DNA elements, two or more copies of one type of the above-mentioned DNA elements, or two or more different types of the above-mentioned DNA elements in combination, and further containing a foreign gene expression unit is provided. When a foreign gene is expressed in a host cell using the above-mentioned foreign gene expression vector, the DNA element may be located immediately upstream or downstream of the gene expression unit, or may be located at a position away from the gene expression unit. Further, one foreign gene expression vector containing a plurality of such DNA elements may be used. Incidentally, the DNA element may be inserted in either forward or reverse orientation with respect to the gene expression unit.

Further, as the vector to be used in the invention, a vector containing one type of the above-mentioned DNA elements, two or more copies of one type of the above-mentioned DNA elements, or two or more different types of the above-mentioned DNA elements in combination, and containing no gene expression unit (hereinafter also referred to as an "element vector") is also included. Such an element vector can be used in combination with the above-mentioned foreign gene expression vector containing the DNA element or a foreign gene expression vector containing no DNA element and containing only the foreign gene expression unit. By allowing the element vector to coexist with the foreign gene expression vector, the expression of the foreign gene is enhanced as compared with cases where the foreign gene expression vector is used alone and, therefore, the combination of the above-mentioned vectors is also included in the foreign gene expression vector of the invention.

The gene encoding the foreign protein is not particularly limited, however, examples thereof include reporter genes such as secretory alkaline phosphatase (SEAP), a green fluorescent protein (GFP), and luciferase; various enzyme genes such as an α-amylase gene and an α-galactosidase gene; genes of various interferons which are pharmaceutically useful and physiologically active proteins such as interferon α and interferon γ; genes of various interleukins such as IL-1 and IL-2; various cytokine genes such as an erythropoietin (EPO) gene and a granulocyte colony-stimulating factor (G-CSF) gene; growth factor genes; and antibody genes. These genes may be obtained by any method.

The invention is particularly effective in relation to a protein which is highly hydrophobic and a protein which is difficult to get secreted and produced due to composite formation. Thus, the above-mentioned foreign protein includes a multimeric protein such as a heteromultimer which is an antibody or a functional fragment thereof. The "functional fragment of an antibody" refers to a partial fragment of an antibody having an antigen-binding activity and includes Fab, F(ab')2, Fv, scFv, diabodies, linear antibodies, polyspecific antibodies formed from antibody fragments, and the like. The functional fragment of an antibody also includes Fab' which is a monovalent fragment in a variable region of an antibody obtained by treating F(ab')2 under reducing conditions. However, the functional fragment is not limited to these molecules as long as the fragment has a binding affinity for an antigen. Further, these functional fragments include not only a fragment obtained by treating a full-length molecule of an antibody protein with an appropriate enzyme, but also a protein produced in an appropriate host cell using a genetically modified antibody gene.

The gene expression unit has, in the direction of the reading frame of transcription, at least a promoter region, a foreign gene, and a transcription terminator region (poly(A) addition signal). The promoter which can be used here may be a constitutive expression promoter or an inducible expression promoter. Examples of a constitutive expression promoter include various natural promoters such as an SV40 early promoter, an adenovirus E1A promoter, a CMV (cytomegalovirus) promoter, an EF-1α (human elongation factor-1a) promoter, an HSP70 promoter, an MT promoter, an RSV promoter, a UBC promoter, and an actin promoter; and artificial (fusion) promoters such as an SRa promoter and a CAG promoter. Further, the poly(A) addition sequence may be a sequence having the activity of causing transcription termination for the transcription from the promoter, and may be a sequence from a gene the same as or different from the promoter.

It is necessary to use a strong promoter in order to increase the production of a foreign protein. However, when it is attempted to produce a protein which is difficult to have fold or a protein which is difficult to get secreted using a highly active promoter, the protein may instead fail to be secreted. This is because when the protein is produced in an amount exceeding the capacity of the ribosome in which translation is performed and the endoplasmic reticulum where folding and secretion are performed, the excessively produced protein is denatured, accumulated, and ubiquitinated in cells, and then degraded by proteosomes. Accordingly, it is preferred that a promoter, which can attain an expression level to such an extent that the resulting protein is not denatured or aggregated or the amount of the resulting protein does not exceed the secretion capacity, is appropriately selected. Alternatively, the promoter is used by adjusting (for example, decreasing) the activity of the promoter. Among the multimeric proteins, a molecule forming a heteromultimer is susceptible to the above-described effect, and, in particular a molecule, such as an antibody, which is a heterotetramer. An antibody has two heavy chain molecules and two light chain molecules which are associated with one another, and therefore, in order to appropriately associate the molecules, the expression level thereof is an important factor.

Further, the foreign gene expression vector and the element vector of the invention can each contain a selection marker for selecting a transformant. By using, for example, a drug-resistant marker which imparts resistance to a drug such as cerulenin, aureobasidin, Zeocin, canavanine, cycloheximide, hygromycin, puromycin, blasticidin, tetracycline, kanamycin, ampicillin, or neomycin, a transformant can be selected. Further, where a gene which imparts resistance to a solvent such as ethanol, resistance to the osmotic pressure of glycerol, a salt, or the like, resistance to a metal ion such as a copper ion, or the like is used as a marker, a transformant can also be selected.

The foreign gene expression vector and the element vector of the invention may each be a vector which is not incorporated into the chromosomal DNA. In general, the foreign gene expression vector is transfected into a host cell, and thereafter randomly incorporated into the chromosome. However, by using a constituent component derived from a mammalian virus such as simian virus 40 (SV40), a papillomavirus (BPV, HPV), or EBV, the vector can be used as an episomal vector which is self-replicable in the transfected host cell. For example, a vector containing an SV40-derived replication origin (oriP) and a sequence encoding an SV40 large T antigen which is a trans-acting factor, a vector containing an EBV-derived oriP and a sequence encoding EBNA-1, or the like can be used. The effect of the DNA element can be expressed by the activity of enhancing foreign gene expression regardless of the type of vector or the presence or absence of incorporation thereof into the chromosome.

4. Transformed Cell

The transformed cell of the invention is a transformed cell into which the foreign gene expression vector described in the above item "3" containing the DNA element described in the above item "1" has been introduced. As the foreign gene expression vector, only a foreign gene expression vector containing a DNA element may be introduced (A), or a foreign gene expression vector containing a DNA element and also an element vector described in the above item "3" may be introduced in combination (B). Alternatively, a foreign gene expression vector containing no DNA element and an element vector may be introduced in combination (C).

The expression of a foreign gene in a host cell using the above combination of (B) or (C) can be performed according to, for example, the method of Girod et al. (Biotechnology and Bioengineering, 91, 2-11 (2005)) and the method of Otte et al. (Biotechnol. Prog., 2007, 23, 801-807 (2007)).

Examples of the host cell to be transformed include eucaryotic cells, preferred examples thereof include mammalian cells, more preferred examples include cells derived from humans, mice, rats, hamsters, monkeys, or cattle. Examples of such mammalian cells include COS-1 cells, 293 cells, and CHO cells (CHO-K1, DG44, CHO dhfr-, CHO-S), however, the host cell is not limited thereto.

In the invention, any method may be used for introducing the expression vector into the host cell as long as the method allows the introduced gene to be stably present in the host cell and to be adequately expressed therein. Examples of the method which is generally used include a calcium phosphate method (Ito et al., (1984) Agric. Biol. Chem., 48, 341), an electroporation method (Becker, D. M. et al., 1990; Methods. Enzymol., 194, 182-187), a spheroplast method (Creggh et al., Mol. Cell. Biol., 5, 3376 (1985)), a lithium acetate method (Itoh, H. (1983) J. Bacteriol. 153, 163-168), and a lipofection method.

5. Method for Producing Foreign Protein

In the invention, a foreign protein can be produced by culturing the transformed cell described in the above item "4", into which a gene encoding the foreign protein has been introduced using the vector described in the above item "3" by a known method, collecting the protein from the resulting culture product, followed by purification of the protein. The term "culture product" as used herein refers to cultured cells or a cell homogenate in addition to a culture supernatant. Incidentally, as the foreign protein which can be produced using the transformed cell described in the above item "4", not only a monomeric protein, but also a multimeric protein can be selected. In cases where a hetero-multimeric protein formed of a plurality of different subunits is produced, it is necessary to introduce a plurality of genes encoding these subunits into the host cell described in the above item "4", respectively.

The method for culturing the transformed cell can be performed according to conventional methods for culturing host cells.

In cases where the transformed cell is a mammalian cell, the cell is cultured under conditions of, for example, 37° C. and 5% or 8% $CO_2$ for a culture time of from about 24 to 1000 hours. The culturing can be performed through batch culture, fed-batch culture, continuous culture, or the like under static, shaking, stirring, or aeration conditions.

The confirmation of the expression product of the gene encoding the foreign protein from the above-mentioned culture product (culture solution) can be performed by SDS-PAGE, a Western analysis, ELISA, or the like. In order to isolate and purify the produced protein, a conventional protein isolation and purification method may be used. After completion of the culturing, in cases where the target protein is produced in the cells, the cells are homogenized using an ultrasonic homogenizer, a French press, a Manton-Gaulin homogenizer, Dinomil, or the like, thereby obtaining the target protein. Further, cases where the target protein is produced outside the cells, the culture solution is used as such, or the cells are removed by centrifugation or the like. Thereafter, the target protein is collected by extraction or the like using an organic solvent, and then the collected target protein may be isolated and purified by using techniques such as various chromatography techniques (hydrophobic chromatography, reverse-phase chromatography, affinity chromatography, ion exchange chromatography, etc.), gel filtration using a molecular sieve, and electrophoresis using a polyacrylamide gel or the like alone or in combination according to need.

The above-mentioned culturing methods and purification methods are only examples, and the methods are not limited thereto. The amino acid sequence of the purified gene product can be confirmed by a known amino acid analysis technique, such as automated amino acid sequence determination using the Edman degradation method.

6. Method for Producing Antibody Protein

As the hetero-multimeric protein to be produced using the production method described in the above item "5", an antibody protein can be exemplified. The antibody protein is a tetrameric protein comprising two molecules of heavy chain polypeptides and two molecules of light chain polypeptides. Accordingly, in order to obtain such an antibody protein in a state of maintaining an antigen-binding affinity, it is necessary to introduce both heavy and light chain genes into the transformed cell described in the above item "4". In this case, the heavy and light chain gene expression units may be present on the same expression vector or different expression vectors.

As the antibody to be produced in the invention, an antibody prepared by immunizing an experimental animal such as a rabbit, a mouse, or a rat with a desired antigen can be exemplified. Further, a chimeric antibody and a humanized antibody obtained by using the above-mentioned antibody as a starting material can be also exemplified as the antibody to be produced in the invention. Further, a human antibody obtained using a genetically modified animal or a phage display method is also included in the antibody to be produced in the invention.

The antibody gene to be used for the production of the antibody is not limited to an antibody gene having a specific polynucleotide sequence as long as a combination of a heavy chain polypeptide and a light chain polypeptide to be transcribed and translated from the antibody gene has an activity of binding to a given antigen protein.

Further, it is not necessary that the antibody gene encodes the full-length molecule of the antibody, and a gene encoding a functional fragment of the antibody can be used. Such a gene encoding a functional fragment thereof can be obtained by genetically modifying a gene encoding the full-length molecule of an antibody protein.

7. Production Method for Other Foreign Proteins

Examples of the foreign protein to be produced using the production method of the invention include, in addition to the above-mentioned antibodies, various proteins derived from humans or non-humans, functional fragments thereof, and modified products thereof. Examples of such proteins and the like include peptide hormones such as atrial natriuretic peptide (ANP), brain natriuretic peptide (BNP), C-type natriuretic peptide (CNP), vasopressin, somatostatin, growth hormone (GH), insulin, oxytocin, ghrelin, leptin, adiponectin, renin, calcitonin, osteoprotegerin, and insulin-like growth factor (IGF); cytokines such as interleukin, chemokine, interferon, tumor necrosis factors (such as TNF-α, TNF-β, and TNF super family), nerve growth factors (such as NGF), cell growth factors (such as EGF, FGF, PDGF, HGF, and TGF), hematopoietic growth factors (such as CSF, G-CSF, and erythropoietin), and adipokine; receptors such as TNF receptors; enzymes such as lysozyme, protease, proteinase, and peptidase; functional fragments thereof (fragments having part or all of the biological activity of the original protein), and fusion proteins comprising any of these proteins. However, the proteins are not limited thereto.

EXAMPLES

Hereinafter, the invention will be specifically described with reference to the Examples. However, these Examples do not limit the technical scope of the invention. The plasmids, restriction enzymes, DNA modification enzymes, and the like to be used in the Examples of the invention are commercially available products and can be used according to common procedures. Further, procedures used for DNA cloning, polynucleotide sequence determination, transformation of a host cell, culturing of a transformed host cell, collection of a protein from the resulting culture product, purification of a protein, and the like are also well known to those skilled in the art or can be found in the literature.

Example 1

Extraction of DNA Element (1-1) Chromatin Immunoprecipitation Using Anti-Acetylated Histone H3 Antibody ChIP using an anti-acetylated histone antibody was performed using EZ ChIP (Upstate) according to the following procedure. Incidentally, unless otherwise stated, as the antibodies, buffers, and the like used in the following procedure, Upstate's products were used.

First, 293F cells (Invitrogen) were cultured using GIBCO (registered trademark) FreeStyle™ 293 Medium (Invitrogen) under conditions of 37° C. and 8% $CO_2$, followed by centrifugation (1000 rpm, 5 min, room temperature), whereby cells in the growth phase were collected. After $2 \times 10^7$ cells were fixed in a medium containing 1% formaldehyde for 10 minutes, 10× glycine was added thereto, followed by incubation at room temperature for 5 minutes. After centrifugation (3000 rpm, 5 min, 4° C.), the supernatant was removed, and PBS was added to the cell pellet to suspend the cells. Then, the cell suspension was centrifuged again to remove PBS, and thereafter an SDS lysis buffer was added to the cell pellet to suspend and lyse the cells. Each sample obtained by cell lysis was subjected to DNA fragmentation using an ultrasonic homogenizer (BRANSON) while cooling the sample with ice water, and a dilution buffer containing a protease inhibitor cocktail and Protein G-immobilized agarose were added thereto. The resulting mixture was rotated at 4° C. for 1 hour, followed by centrifugation, and then the supernatant was collected. Subsequently, 10 μg of normal rabbit IgG or an α-acetyl histone H3 antibody was added thereto, followed by rotating overnight at 4° C. To the resulting solution, Protein G-immobilized agarose was added, and the resulting mixture was rotated at 4° C. for 1 hour, followed by centrifugation, and then the pellet was collected. The thus obtained pellet was washed twice with Low Salt Immune Complex Wash Buffer, twice with High Salt Immune Complex Wash Buffer, twice with LiCl Immune Complex Wash Buffer, and finally four times with TE Buffer. Then an elution buffer (containing 20 μl of 1 M sodium hydrogen carbonate, 10 μl of SDS, and 170 μl of sterile water) was added thereto. After 30 minutes, the mixture was centrifuged, and the supernatant was collected.

Subsequently, 5 M sodium chloride was added to the supernatant, and the resulting mixture was heated overnight at 65° C. Then RNase A was added thereto, and the resulting mixture was incubated at 37° C. for 30 minutes. Then 0.5 M EDTA, 1 M Tris-HCl, and Proteinase K were added thereto, and the resulting mixture was incubated at 45° C. for 2 hours.

Finally, Reagents A, B, and C were added thereto in an amount 5 times greater than that of the solution obtained by the treatment with Proteinase K, followed by centrifugation (10000 rpm, 30 sec, room temperature) using Spin filter, whereby chromatin-immunoprecipitated DNA was purified.

(1-2) Microarray Analysis

By using GenomePlex Complete Whole Genome Amplification (WGA) Kit (Sigma), each ChIP sample obtained in (1-1) was amplified. The procedure was in accordance with Sigma's protocol accompanying the Kit.

In order to confirm ChIP, by using 320 ng of each DNA amplified by WGA as a template, and also using the following primers and SYBR (registered trademark) Premix Ex Taq™ (Perfect Real Time) (TAKARA), a glycelaldehyde-3-phosphate dehydrogenase (GAPDH) internal gene was amplified by the PCR method (95° C. for 5 sec and 60° C. for 20 sec×45 cycles). Incidentally, GAPDH is a house keeping gene to be used as a positive control for confirming whether a DNA element is enriched by ChIP, and the PCR method was performed using primers attached to EZ ChIP (Upstate).

```
                                        (SEQ ID NO: 8)
         5'-TACTAGCGGTTTTACGGGCG-3'

(SEQ ID NO: 9)
         5'-TCGAACAGGAGGAGCAGAGAGCGA-3'
```

As shown in FIG. 1, it was confirmed that GAPDH was amplified specifically in the sample subjected to immunoprecipitation with an anti-acetylated histone H3 antibody. Each of the DNA samples amplified by WGA was subjected to microarray analysis (NimbleGen) to perform Chromatin Immunoprecipitation-on-chip (ChIP-on-chip). "ChIP-on-chip" is a technique for identifying each DNA element by subjecting each DNA enriched in (1-1) to microarray analysis.

(1-3) Extraction of DNA Element

Based on the results of the ChIP-on-chip analysis obtained in (1-2), 5 sequences having an AT content of 62% or more were extracted.

A2: chromosome 15 (80966429 to 80974878)
A7: chromosome 11 (88992123 to 89000542)
A18: chromosome 4 (111275976 to Ser. No. 11/284,450)
B5: chromosome 1 (143034684 to 143043084)
C14: chromosome 11 (46089056 to 46097482)

Example 2

Effect of DNA Element Using Expression of Secretory Alkaline Phosphatase (SEAP) as Index (2-1) Construction of SEAP Expression Vector By using pSEAP2-control (Clontech) as a template, the SEAP gene was amplified by the PCR method (94° C. for 30 sec and 68° C. for 2 min×40 cycles) using the following primers and KOD-plus- (TOYOBO).

```
                                             (SEQ ID NO: 10)
  5'-AAAGCTAGCATGCTGCTGCTGCTGCTGCTGGGCC-3'

(SEQ ID NO: 11)
  5'-AAAAGATCTTCATGTCTGCTCGAAGCGGCCGGCCGC-3'
```

Subsequently, the amplified SEAP fragment was separated by agarose gel electrophoresis and cut out from the gel, followed by purification using a QIAquick Gel Extraction Kit (Qiagen). The thus obtained DNA fragment was used as an insert. The insert was digested with the restriction enzymes NheI and BglII, and a vector pIRES hyg3 (Clontech) was digested with the restriction enzymes NheI and BamHI. The resulting DNA fragments were subjected to agarose gel electrophoresis to separate the target fragments, respectively, and the target fragments were cut out from the gel, followed by purification. Then, a ligation reaction and transformation were performed. The ligation reaction was performed using LigaFast Rapid DNA Ligation System (Promega). The transformation was performed as follows. First, frozen competent cells JM109 (TAKARA) were thawed, and 10 μl of a solution obtained after the ligation reaction was added to a solution of the thawed cells, and the resulting mixture was left to stand on ice for 30 minutes. Thereafter, a heat shock (42° C., 45 sec) was applied to the mixture, and the mixture was cooled on ice for 5 minutes. To this cell suspension, 1 ml of LB medium was added, and the resulting mixture was shaken at 37° C. for 1 hour. Then, the mixture was plated on an LB plate containing 0.1 mg/ml ampicillin, and the plate was incubated at 37° C. for 14 to 16 hours. Thereafter, by alkaline lysis, a target plasmid was collected from colonies cultured on the LB plate. Finally, the polynucleotide sequence of SEAP in the plasmid obtained by alkaline lysis was determined, whereby pCMV/SEAP ires Hygro was constructed.

(2-2) Cloning of DNA Element

Subsequently, each of the DNA elements extracted in Example 1 was cloned into the SEAP expression vector obtained in (2-1) using BAC SUBCLONING Kit (Gene Bridges) from a bacterial artificial chromosome (BAC) containing a polynucleotide sequence corresponding to each of the DNA elements.

First, pCMV/SEAP ires Hygro obtained in (2-1) was digested with the restriction enzyme SpeI for several hours, followed by ethanol precipitation, and the precipitate was dissolved in sterile water. By using the vector digested with SpeI as a template, the PCR method (94° C. for 15 sec, 55° C. for 30 sec, and 68° C. for 10 min×30 cycles) was performed using the following primers and KOD-plus- (TOYOBO).

A2D:
(SEQ ID NO: 12)
5'-GGAAATTGAGAAGTATCATTCACAACAGTACCACAAACATGAAATAA

ATGTGGATCCTATTAATAGTAATCAATTACG-3'

A2R:
(SEQ ID NO: 13)
5'-CTCATTCTGTGGGTTGTCATTTCACTTCCTTGATGCTATCCTTTCAA

GCAAAATCCTAGTCAATAATCAATGTCAACG-3'

A7D:
(SEQ ID NO: 14)
5'-CTTATTTTCTAAGTAGTATAGACTTAATTGTGAGAACAAAATAAAAA

CTTGGATCCTATTAATAGTAATCAATTACG-3'

A7R:
(SEQ ID NO: 15)
5'-CTCTTCCCATTCTCATTTGAATCTACTTCAAAAGGTTTACCATACTA

AGACCTAGTCAATAATCAATGTCAACG-3'

A18D:
(SEQ ID NO: 16)
5'-CGCCTGTAATCCCAGCACTTTGGGAGGCTGAGGCGGGTGGATCACCT

GAGGTCGATCCTATTAATAGTAATCAATTACG-3'

A18R:
(SEQ ID NO: 17)
5'-CATACAGAAGCCAGTTTGAACTGAGACCTCACTCCATTTCTTACAAG

TTATGCCCTAGTCAATAATCAATGTCAACG-3'

B5D:
(SEQ ID NO: 18)
5'-ACCGTTTTATATTGTTTAAGCATTTCCTAGACATATTTGGCTACAAA

TCTAGATCCTATTAATAGTAATCAATTACG-3'

B5R:
(SEQ ID NO: 19)
5'-GATCTTAGGGGGGCTGATTATATAAAACAATAGAAATGTAGTCTTAG

ATGAAACCTAGTCAATAATCAATGTCAACG-3'

C14D:
(SEQ ID NO: 20)
5'-CACAAAGTTCACTGTCAAGGCCAGGTGATGAGGCCCACACATGCCCG

GACCTTGATCCTATTAATAGTAATCAATTACG-3'

C14R:
(SEQ ID NO: 21)
5'-CAAAACCTCATCTCTACTGAAAATAGAAAATTAGCTGGGCGTGGTGG

CAGGTGCCCTAGTCAATAATCAATGTCAACG-3'

After the amplification was confirmed by agarose gel electrophoresis using a portion of the reaction solution, the rest of the reaction solution was subjected to ethanol precipitation. The precipitate was dissolved in sterile water, and the resulting solution was used as DNA for transformation.

Subsequently, preparation of *Escherichia coli* for transformation was performed.

BAC clones corresponding to the 5 sequences extracted in Example 1 are as follows.

| Extracted sequence | Corresponding BAC clone |
| --- | --- |
| A2 | RP11-152F13 |
| A7 | RP11-643G5 |
| A18 | RP11-115A14 |
| B5 | RP11-640M9 |
| C14 | RP11-702F3 |

Figure 2:
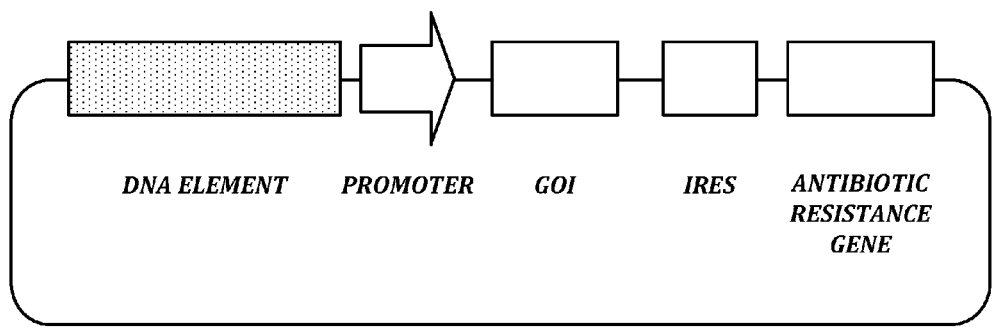
FIG. 2 is a schematic view of an SEAP expression vector into which a DNA element has been inserted.

10 µl of the above-mentioned BAC (Advanced GenoTechs Co.) which was thawed was inoculated into 1 ml of a medium (containing chloramphenicol at a final concentration of 15 µg/ml) and incubated overnight at 37° C. 30 µl of the culture solution was transferred to 1.4 ml of a medium (containing chloramphenicol at a final concentration of 15 µg/ml) and incubated at 37° C. for 2 hours. Centrifugation and washing with sterile water were repeated twice, and the cells were suspended in 20 µl of sterile water. To a cooled cuvette (0.1 cm), 1 µl of pRED/ET (Gene Bridges) and *Escherichia coli* were added, followed by electroporation (1350 V, 10 µF). Then, 1 ml of SOC medium was added thereto, and the resulting mixture was incubated at 30° C. for 70 minutes. 100 µl of the culture solution was plated on an LB plate (containing tetracycline and chloramphenicol at final concentrations of 3 µg/ml and 15 µg/ml, respectively), and incubated overnight at 30° C. On the subsequent day, each colony thus obtained was inoculated into 1 ml of a medium (containing tetracycline and chloramphenicol at final concentrations of 3 µg/ml and 15 µg/ml, respectively), and incubated overnight at 30° C. 30 µl of the culture solution was transferred to 1.4 ml of a medium (containing tetracycline and chloramphenicol at final concentrations of 3 µg/ml and 15 µg/ml, respectively), and incubated at 30° C. for 2 hours. Then, 50 µl of 10% L-arabinose was added thereto, and incubation was further performed at 37° C. for 1 hour. Thereafter, washing with sterile water was repeated twice, and *Escherichia coli* which was suspended in 30 µl of sterile water and 1 µl of the DNA for transformation were added to a cooled cuvette (0.1 cm), followed by electroporation (1350 V, 10 µF). Then, 1 ml of SOC medium was added thereto, and the resulting mixture was incubated at 37° C. for 90 minutes. The total amount of the culture solution was plated on an LB plate (containing 100 µg/ml ampicillin), and the plate was incubated. Thereafter, a target plasmid was obtained by alkaline lysis. Finally, the sequence of the obtained plasmid and the restriction enzyme sites thereof were confirmed, whereby a target plasmid was constructed. The vector construct is shown in FIG. 2.

(2-3) Evaluation Using SEAP Expression as Index

Each plasmid constructed in (2-2) was evaluated using the host cell CHO-K1 (ATCC) and transfection reagent Lipofectamine 2000 (Invitrogen).

Antibiotic selection with hygromycin at 800 µg/ml was performed for about 2 weeks starting 2 days after transfection, whereby a stably expressing polyclonal cell line was established. The thus established cell line was subjected to medium replacement on the day before measurement, and a given number of the cells were seeded into a 24-well plate (IWAKI). At 24 hours after plating the cells, the culture supernatant was collected, and the activity of SEAP was measured. The activity of SEAP in the culture supernatant was measured using SensoLyte™ pNPP Secreted Alkaline Phosphatase Reporter Assay (ANASPEC).

Figure 3:
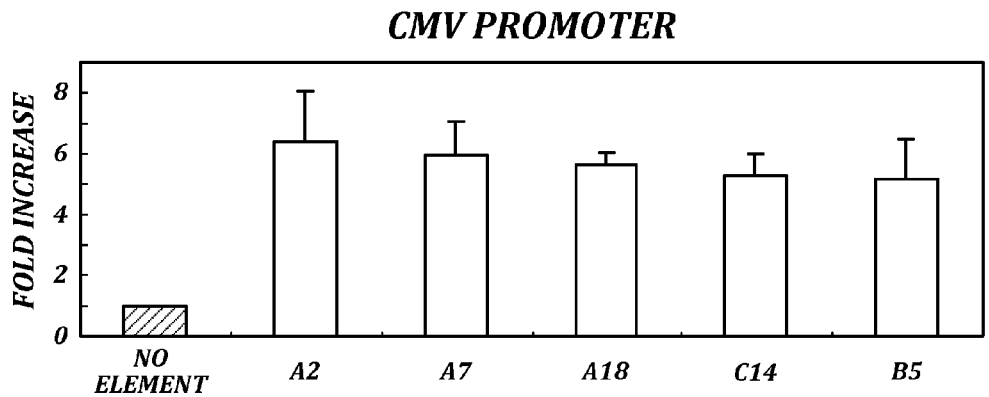
FIG. 3 is a graph showing the expression of SEAP under the control of a CMV promoter in a stably expressing CHO cell line either without a DNA element or with DNA element A2, A7, A18, B5, or C14. The effects of DNA elements A2, A7, A18, B5, and C14 on enhancement of expression were confirmed.

The measured results are shown in FIG. 3. When the activity of SEAP of the control with no element was normalized to 1, the activity of SEAP in the culture supernatant of the stably expressing CHO cell line having the DNA element A2, A7, A18, B5, or C14 showed a numerical value five times or more higher than that of the control. Based on the results, it was confirmed that all the 5 types of DNA elements dramatically enhance SEAP expression. Incidentally, the polynucleotide sequences of the above 5 types of DNA elements are represented by SEQ ID NOS: 1 to 5 in the Sequence Listing, respectively.

Example 3

Generality of Promoter to be Used in Combination

The promoter for the vector used in the evaluation of the DNA elements in Example 2 was a CMV promoter, and thus the use of DNA elements in combination with other general promoters was studied in Example 3.

(3-1) Construction of SEAP Expression Vector Using EF-1α and SV40 Promoters

By using pSEAP2-control (Clontech) as a template, the SEAP gene was amplified by the PCR method (94° C. for 30 sec and 68° C. for 2 min×40 cycles) using the primers described in (2-1) and KOD-plus-. The amplified SEAP was prepared as an insert in the same manner as in (2-1). The insert was digested with the restriction enzymes NheI and BglII, and a vector pIRES puro3 (Clontech) was digested with the restriction enzymes NheI and BamHI, and pCMV/SEAP ires Puro was constructed in the same manner as in (2-1).

Subsequently, by using pEF1/V5-His A (Invitrogen) as a template, an EF-1α promoter was amplified by the PCR method (94° C. for 15 sec, 60° C. for 30 sec, and 68° C. for 2 min×30 cycles) using the following primers and KOD-plus-.

```
                                             (SEQ ID NO: 22)
5'-AAAACTAGTCAGAGAGGAATCTTTGCAGCTAATGGACC-3'

(SEQ ID NO: 23)
5'-AAAGATATCCCTAGCCAGCTTGGGTGGTACCAAGC-3'
```

By using the above-constructed pCMV/SEAP ires Puro as a vector, digestion with the restriction enzymes SpeI and EcoRV was performed for the vector and the promoter, and pEF/SEAP ires Puro was constructed according to the method described in (2-1).

Similarly, by using pcDNA3.1+(Invitrogen) as a template, an SV40 promoter was amplified by the PCR method (94° C. for 15 sec, 60° C. for 30 sec, and 68° C. for 1 min×30 cycles) using the following primers and KOD-plus-.

```
                                             (SEQ ID NO: 24)
5'-AAAACTAGTCTGTGGAATGTGTGTCAGTTAGGGTG-3'

(SEQ ID NO: 25)
5'-AAAGATATCAGCTTTTTGCAAAAGCCTAGGCCTC-3'
```

By using the above-constructed pCMV/SEAP ires Puro as a vector, digestion with the restriction enzymes SpeI and EcoRV was performed for the vector and the promoter, and pSV40/SEAP ires Puro was constructed according to the method described in (2-1).

(3-2) Cloning of DNA Element A2 or A7

Subsequently, cloning of the DNA element A2 or A7 was performed using pEF/SEAP ires Puro and pSV40/SEAP ires Puro constructed in (3-1) as basic structures.

First, pEF/SEAP ires Puro and pSV40/SEAP ires Puro were digested with the restriction enzyme SpeI for several hours, followed by ethanol precipitation, and the precipitate was dissolved in sterile water. By using the respective vectors digested with SpeI as templates, DNA for transformation was prepared by the PCR method (94° C. for 15 sec, 55° C. for 30 sec, and 68° C. for 10 min×30 cycles) using the following primers and KOD-plus-.

```
A2 (EF/D):
                                             (SEQ ID NO: 26)
5'-GGAAATTGAGAAGTATCATTCACAACAGTACCACAAACATGAAATAA

ATGTGCTAGTCAGAGAGGAATCTTTGCAGC-3'

A2 (SV40/D):
                                             (SEQ ID NO: 27)
5'-GGAAATTGAGAAGTATCATTCACAACAGTACCACAAACATGAAATAA

ATGTGCTAGTCTGTGGAATGTGTGTCAGTTAG-3'

A2 (EF and SV40/R):
                                             (SEQ ID NO: 28)
5'-CTCATTCTGTGGGTTGTCATTTCACTTCCTTGATGCTATCCTTTCAA

GCAAAATTTTAAAACTTTATCCATCTTTGCA-3'

A7 (EF/D):
                                             (SEQ ID NO: 29)
5'-CTTATTTTCTAAGTAGTATAGACTTAATTGTGAGAACAAAATAAAAA

CTTGCTAGTCAGAGAGGAATCTTTGCAGC-3'

A7 (SV40/D):
                                             (SEQ ID NO: 30)
5'-CTTATTTTCTAAGTAGTATAGACTTAATTGTGAGAACAAAATAAAAA

CTTGCTAGTCTGTGGAATGTGTGTCAGTTAG-3'

A7 (EF and SV40/R):
                                             (SEQ ID NO: 31)
5'-CTCTTCCCATTCTCATTTGAATCTACTTCAAAAGGTTTACCATACTA

AGAACTAGTTTTAAAACTTTATCCATCTTTGCA-3'
```

By using the thus prepared DNA for transformation and BAC transfected with pRed/ET, the DNA element A2 or A7 was cloned into the vector described in (3-1). The vector construct is shown in FIG. 2. Incidentally, the procedure was performed according to the method described in (2-2).

(3-3) Evaluation Using SEAP Expression as Index

Each plasmid constructed in (3-2) was evaluated using the host cell CHO-K1 (ATCC) and transfection reagent Lipofectamine 2000 (Invitrogen).

Antibiotic selection with puromycin at 8 µg/ml was performed for about 2 weeks starting 2 days after transfection, whereby a stably expressing polyclonal cell line was established. The thus established cell line was subjected to medium replacement on the day before measurement, and a given number of the cells were seeded into a 24-well plate. At 24 hours after plating the cells, the culture supernatant was collected, and the activity of SEAP was measured. The activity of SEAP in the culture supernatant was measured using SensoLyte™ pNPP Secreted Alkaline Phosphatase Reporter Assay (ANASPEC).

Figure 4A:
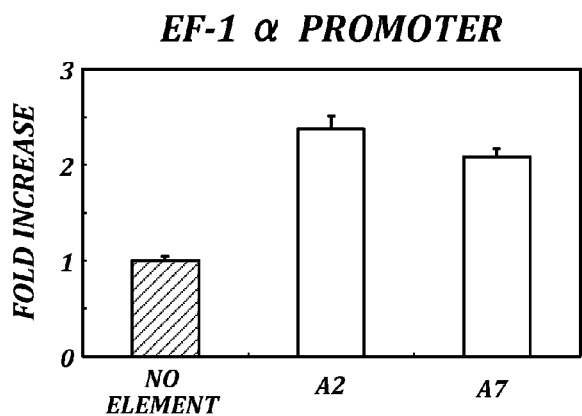
FIG. 4A and FIG. 4B comprise two graphs showing the expression of SEAP under the control of either an EF-1α (FIG. 4A) or an SV40 (FIG. 4B) promoter in a stably expressing CHO cell line either without a DNA element or with DNA element A2 or A7. The effects of DNA elements A2 and A7 on enhancement of expression were confirmed.
Figure 4B:
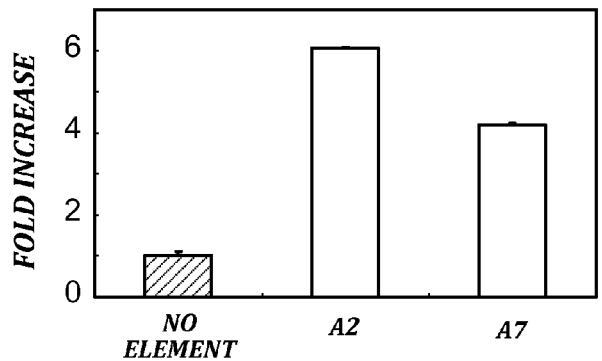

The measurement results are shown in FIG. 4. When the activity of SEAP of the control with no element was normalized to 1, the DNA element A2 or A7 exhibited an effect on enhancement of expression such that the activity of SEAP was twice or more as high in the case of use with the EF-1α promoter, and four times or more higher in the case of use with the SV40 promoter than that of the control. Based on the results, it was confirmed that these DNA elements exhibit the effect of enhancing foreign gene expression when used in combination with a general promoter.

Example 4

Evaluation Using Antibody Expression as Index (4-1) Construction of Human Light Chain Expression Vector pEF6KCL By using a plasmid pEF6/V5-HisB (Invitrogen) as a template, a DNA fragment between position 2174 (immediately downstream of BGHpA) and position 2958 (SmaI) (a DNA fragment containing an f1 origin of replication and SV40 promoter and origin, hereinafter referred to as "fragment A", the polynucleotide sequence of fragment A being represented by SEQ ID NO: 6 in the Sequence Listing) was obtained by the PCR method using the following primers and KOD-plus-.

```
                                      (SEQ ID NO: 32)
5'-CCACGCGCCCTGTAGCGGCGCATTAAGC-3'
```

```
                                      (SEQ ID NO: 33)
5'-AAACCCGGGAGCTTTTTGCAAAAGCCTAGG-3'
```

The obtained fragment A and a DNA fragment containing a DNA sequence encoding a human κ chain secretory signal, a human κ chain constant region, and a human poly(A) addition signal (hereinafter referred to as "fragment B") were ligated by overlapping PCR. The thus obtained DNA fragment in which fragment A and fragment B were ligated was digested with the restriction enzymes KpnI and SmaI, and the resulting fragment was ligated to plasmid pEF6/V5-HisB (Invitrogen) which was digested with the restriction enzymes KpnI and SmaI, whereby a human light chain expression vector pEF6KCL having a signal sequence, a cloning site, a human κ chain constant region, and a human poly(A) addition signal sequence downstream of the EF-1α promoter was constructed.

A DNA fragment obtained by cleaving the pEF6KCL obtained by the above-mentioned method with the restriction enzymes KpnI and SmaI was ligated to pEF1/myc-HisB (Invitrogen) which was digested with KpnI and SmaI, followed by transformation alkaline lysis, and its sequence confirmation, whereby a plasmid pEF1KCL was constructed.

(4-2) Construction of Human Heavy Chain Expression Vector pEF1FCCU

A DNA fragment (the polynucleotide sequence of this DNA fragment is represented by SEQ ID NO: 7 in the Sequence Listing) containing a DNA sequence encoding a human IgG1 signal sequence and a constant region amino acid sequence was digested with the restriction enzymes NheI and PmeI, and the resulting fragment was ligated to a plasmid pEF1KCL which was digested with NheI and PmeI, whereby a human heavy chain expression vector pEF1FCCU having a signal sequence, a cloning site, a human heavy chain constant region, and a human poly(A) addition signal sequence downstream of the EF-1α promoter was constructed.

(4-3) Construction of Single Humanized Antibody Gene X Expression Vector (Humanized Antibody Gene X/pEF_LHN#)

By ligating the L-chain or H-chain expression vector constructed in (4-1) or (4-2), a single humanized antibody expression vector (pEF_LHN (lacking a variable region)) was constructed.

A restriction enzyme SalI site was added by the PCR method to both ends of the gene expression unit from upstream of the promoter to downstream of poly(A) of pEF1KCL. Agarose gel electrophoresis, cutting out of a desired DNA fragment from the gel, and purification of the DNA fragment were then performed, whereby an insert was prepared. By digesting the pEF1FCCU constructed in (4-2) with the restriction enzyme SalI, the vector was linearized at the SalI site located upstream of the gene expression unit. Then, the linearized vector was ligated to the above insert, followed by transformation, alkaline lysis, and sequence confirmation, whereby a single humanized antibody expression vector (pEF_LHN (lacking a variable region)) was constructed.

Subsequently, the following oligonucleotides were introduced into an AatII site of the vector pEF_LHN (lacking a variable region).

```
                                      (SEQ ID NO: 34)
5'-CGCGGCCGCACTAGTGACGT-3'
```

```
                                      (SEQ ID NO: 35)
5'-CACTAGTGCGGCCGCGACGT-3'
```

The respective oligonucleotides were diluted to 5 pmol, and by using T4 Polynucleotide Kinase (TAKARA), a reaction was allowed to proceed at 37° C. for 1 hour. Then, 10× buffer (TAKARA) was added thereto, and annealing was performed at 96° C. for 1 minute at room temperature. These oligonucleotides and the vector pEF_LHN which was digested with the restriction enzyme AatII were ligated, followed by transformation, alkaline lysis, and sequence confirmation, whereby pEF_LHN# (lacking a variable region) was constructed.

By integrating a variable region of the humanized antibody gene X into the above-constructed universal vector (pEF_LHN# (lacking a variable region)), the construction of a humanized antibody gene X expression single vector (humanized antibody gene X/pEF_LHN#) was completed.

First, by using the following primers and KOD-plus-, an L-chain variable region of the humanized antibody gene X was amplified by the PCR method (94° C. for 15 sec, 55° C. for 30 sec, and 68° C. for 1 min×30 cycles).

```
L-chain variable region:
                                      (SEQ ID NO: 36)
5'-AAACATATGGCGACATCCAGATGAC-3'
```

```
                                      (SEQ ID NO: 37)
5'-AAACGTACGCTTGATCTCCACCTTGG-3'
```

The amplified L-chain variable region fragment and the universal vector (pEF_LHN# (lacking a variable region)) were digested with the restriction enzymes NdeI and BsiWI, followed by agarose gel electrophoresis, cutting out of a desired fragment from the gel, purification, ligation reaction, transformation, alkaline lysis, and sequence confirmation, whereby the L-chain variable region was integrated into the vector. In the same manner, by using the following primers and KOD-plus-, an H-chain variable region of the humanized antibody gene X was amplified by the PCR method (94° C. for 15 sec, 55° C. for 30 sec, and 68° C. for 1 min×30 cycles).

```
H-chain variable region:
                                    (SEQ ID NO: 38)
5'-AAAGCTGAGCCAGGTGCAGCTGCAGG-3'

(SEQ ID NO: 39)
5'-AAAGCTGAGCTCACGGTCACCAGGGTTC-3'
```

The amplified H-chain variable region fragment and the vector having the L-chain variable region inserted therein were digested with the restriction enzyme BlpI, followed by agarose gel electrophoresis, cutting out of a desired fragment from the gel, purification, ligation reaction, transformation, alkaline lysis, and sequence confirmation, whereby the H-chain variable region was integrated into the vector and a single humanized antibody gene X expression vector (humanized antibody gene X/pEF_LHN#) was constructed.

(4-4) Construction of Single Humanized Antibody Gene X Expression Vector (Humanized Antibody Gene X/pCMV_LHN#)

By using the single humanized antibody gene X expression vector (humanized antibody gene X/pEF_LHN#) constructed in (4-3) as a basic vector structure, another single humanized antibody gene X expression vector (humanized antibody gene X/pCMV_LHN#) was constructed by replacing the promoter according to the following procedure.

By using pIRES puro3 as a template, a CMV promoter fragment was amplified by the PCR method (94° C. for 30 sec and 68° C. for 3 min×40 cycles) using the following primers and KOD-plus-.

```
Upstream of H-chain:
                                    (SEQ ID NO: 40)
5'-CTTTTGCAAAAAGCTTCGCGTTACATAACTTACGGTAAATGGCC-3'

(SEQ ID NO: 41)
5'-TTCATGGTGGCGCTAGCCCGCAGATATCGATCCGAGCTCGGTA-3'

Upstream of L-chain:
                                    (SEQ ID NO: 42)
5'-TGACGTCGACAAGCTTCGCGTTACATAACTTACGGTAAATGGCC-3'

(SEQ ID NO: 43)
5'-CTGGATGTCGCCATATGCGCCGGAGATCCACAGCAGCAGGGAGATGA

ACACCTGGGTCTGCAGCACCATGGTGGCGCTAGCCCGCAGATATCGATCC

GAGCTCGGTA-3'
```

To the PCR reaction solution, the restriction enzyme DpnI was added, and a reaction was allowed to proceed at 37° C. for 1 hour, followed by purification using miniElute reaction Cleanup kit (Qiagen), whereby a sample for use in In-Fusion was prepared. Meanwhile, the humanized antibody gene X/pEF_LHN# was digested with the restriction enzymes HindIll, NheI, NdeI, and FseI, followed by agarose gel electrophoresis, whereby two large fragments among the resulting fragments were separated. Each of the fragments was cut out from the gel, and the DNA was extracted from the gel, whereby a sample for use in In-Fusion was prepared. All the samples for use in In-Fusion were put together, and cloning was performed using In-Fusion™ Advantage PCR Cloning Kit (TAKARA), followed by transformation, alkaline lysis, and sequence confirmation, whereby a single humanized antibody gene X expression vector (humanized antibody gene X/pCMV_LHN#) was constructed.

(4-5) Cloning of DNA Element A7

A7 was selected from the 5 types of the DNA elements which were confirmed to have an effect of enhancing SEAP expression, and cloned into an antibody expression vector.

In the same manner as in (2-2), by using each of the humanized antibody gene X expression single vectors (humanized antibody gene X/pEF_LHN# and humanized antibody gene X/pCMV_LHN#) digested with the restriction enzyme NotI as a template, DNA for transformation was prepared by the PCR method (94° C. for 15 sec, 55° C. for 30 sec, and 68° C. for 11 min×30 cycles) which was performed using the following primers and KOD-plus-.

```
Humanized antibody gene X/pEF_LHN# D:
                                    (SEQ ID NO: 44)
5'-CTCTTCCCATTCTCATTTGAATCTACTTCAAAAGGTTTACCATACTA

AGACTCGAGGCACTAGTGACGTCAGGTGGCACT-3'

Humanized antibody gene X/pEF_LHN# R:
                                    (SEQ ID NO: 45)
5'-CTCTTCCCATTCTCATTTGAATCTACTTCAAAAGGTTTACCATACTA

AGAGCACTAGTGACGTCAGGTGGCACTTTTCGG-3'

Humanized antibody gene X/pCMV_LHN# D:

Humanized antibody gene X/pEF_LHN# D was used.

Humanized antibody gene X/pCMV_LHN# R:

Humanized antibody gene X/pEF_LHN# R was used.
```

Figure 5:
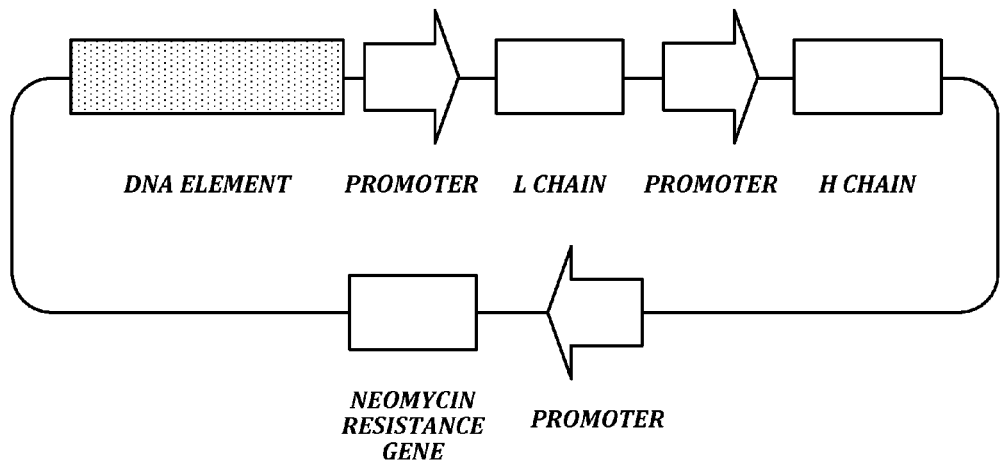
FIG. 5 is a schematic view of an antibody expression (antibody gene X heavy chain and light chain co-expression) vector into which a DNA element has been inserted.

By using the above-prepared DNA for transformation and BAC transfected with pRed/ET, the DNA element A7 was cloned into the single humanized antibody gene X expression vectors described in (4-3) and (4-4). The vector construct is shown in FIG. 5. Incidentally, the procedure was performed according to the method described in (2-2).

(4-6) Evaluation Using Antibody Expression as Index

Each plasmid constructed in (4-5) was evaluated using the host cell CHO-K1 (ATCC) and transfection reagent Lipofectamine 2000 (Invitrogen).

Antibiotic selection with Geneticin (Roche) at 800 μg/ml was performed for about 2 weeks starting 2 days after transfection, whereby a stably expressing polyclonal cell line was established. The thus established cell line was subjected to medium replacement on the day before measurement, and a given number of the cells were seeded into a 24-well plate. At 24 hours after plating the cells, the culture supernatant was collected, and the expression level of the antibody in the culture supernatant was measured by the ELISA method. Incidentally, the ELISA was performed as follows. To a 96-well plate coated with anti-kappa light chain at 50 ng/well, 100 μl of the cell-free culture supernatant was added to each well, and the plate was incubated at 37° C. for 1 hour. Subsequently, the sample (culture supernatant) was removed, and each well was washed with 200 μl of PBS-Tween (0.05%). Then, 100 μl of HRP-labeled anti-human IgG (Fc) was added to each well and the plate was incubated at 37° C. for an additional 1 hour. Thereafter, the HRP-labeled anti-human IgG (Fc) was removed, and each well was washed with PBS-Tween (0.05%). Then, a color was developed using a POD Substrate ABTS Kit (Nacalai), and an absorbance at a measurement wavelength of 405 nm was measured. For the dilution of the anti-kappa light chain, the anti-human IgG (Fc), and the sample, PBS-Tween (0.05%) was used. By using human IgG serially diluted to 12 ng, 6 ng, 3 ng, 1.5 ng, 0.75 ng, 0.375 ng, and 0.1875 ng as a standard, the concentration of the sample was calculated.

Figure 6A:
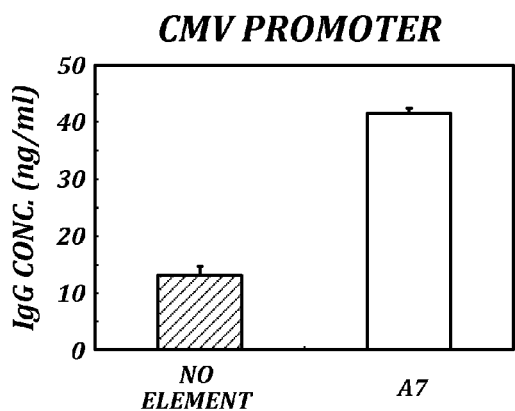
FIG. 6A and FIG. 6B comprise two graphs showing levels of secretion (measured by an ELISA method) of an antibody under the control of either a CMV (FIG. 6A) or an EF-1α (FIG. 6B) promoter in a stably expressing CHO cell line either without a DNA element or with DNA element A7. The effect of DNA element A7 on enhancement of expression was confirmed.
Figure 6B:
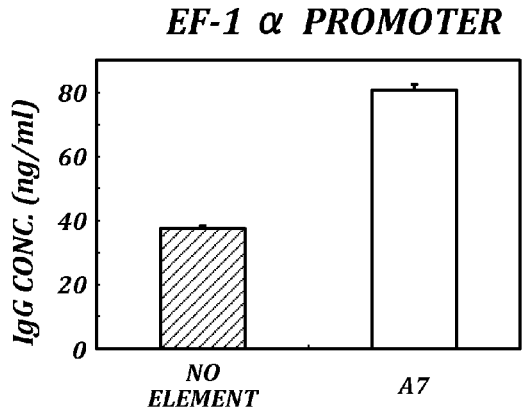
Figure 8A:
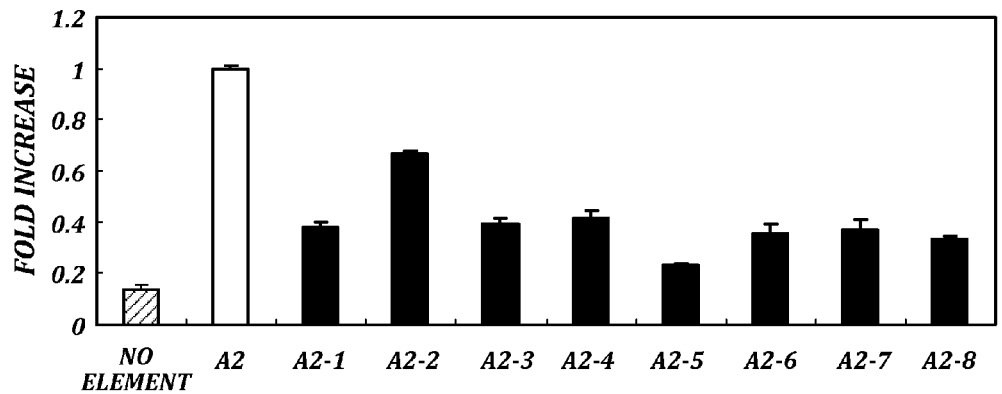
FIG. 8A (A2-1-A2-8), FIG. 8B (A2-9-A2-11), and FIG. 8C (A2-12-A2-17). The effects of DNA element A2 and related sequences on enhancement of expression were confirmed.
Figure 8B:
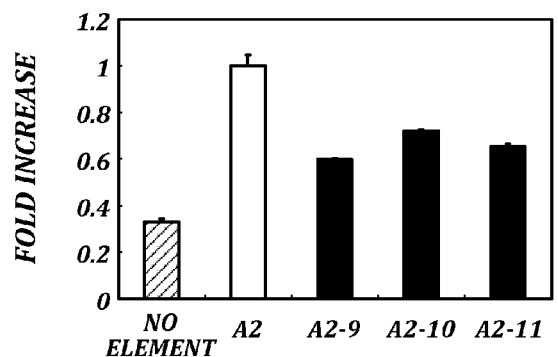
Figure 8C:
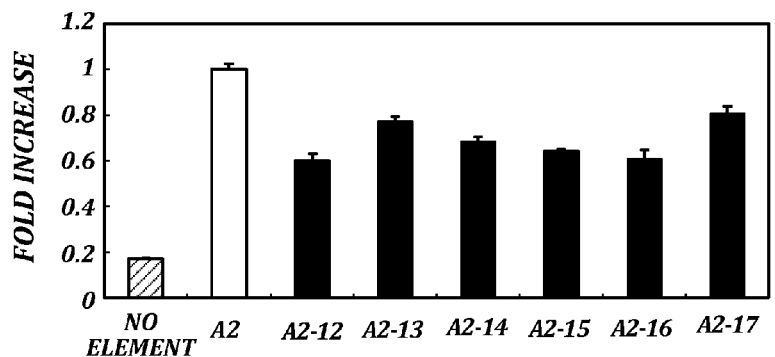
Figure 10A:
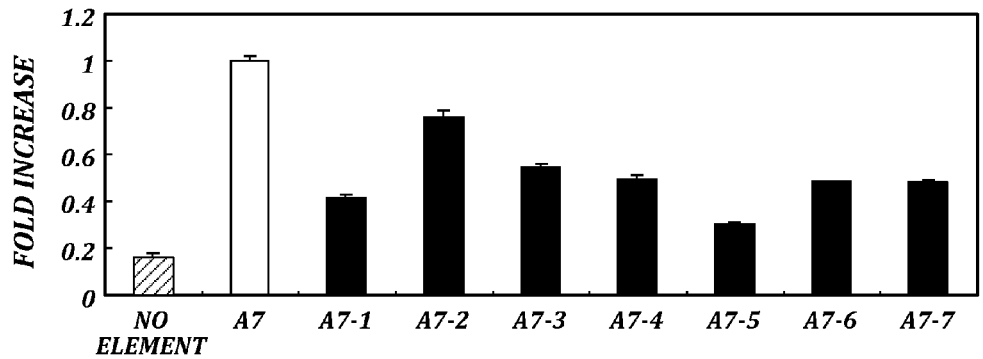
FIG. 10A through FIG. 10C comprise three graphs showing the expression of SEAP in a stably expressing CHO cell line either without a DNA element or with DNA element A7 or a related sequence.
Figure 10B:
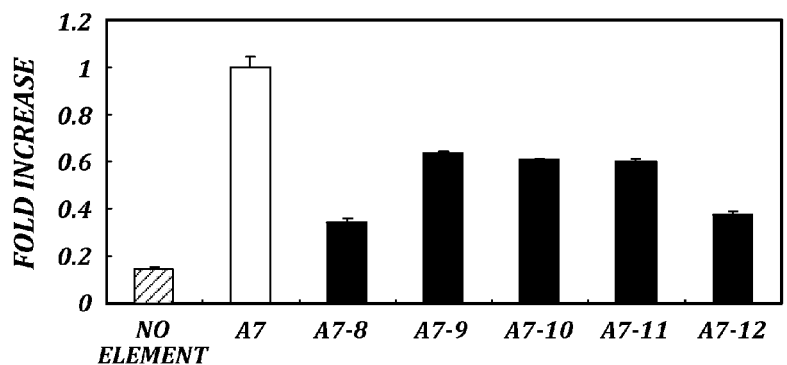
Figure 10C:
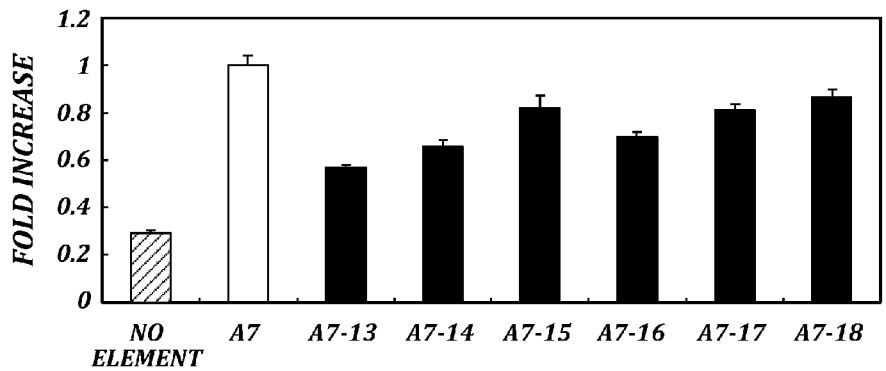
Figures 11, 12:
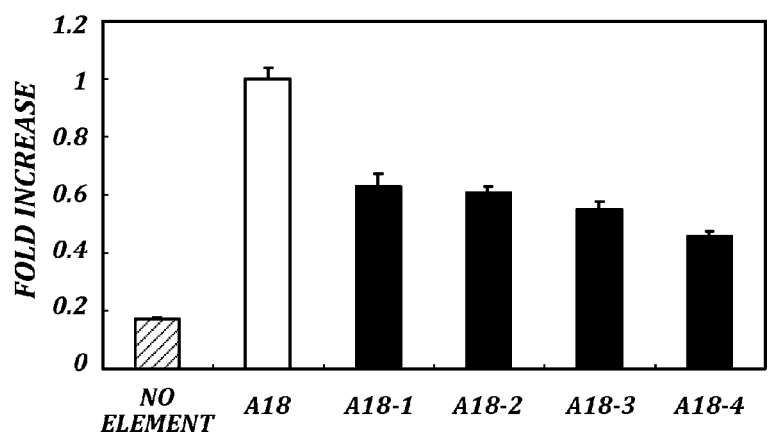
FIG. 11 is a table showing the sequence lengths of DNA element A18 and related sequences.
FIG. 12 is a graph showing the expression of SEAP in a stably expressing CHO cell line either without a DNA element or with DNA element A18 or a related sequence. The effects of DNA element A18 and related sequences on enhancement of expression were confirmed.
Figures 13, 14:
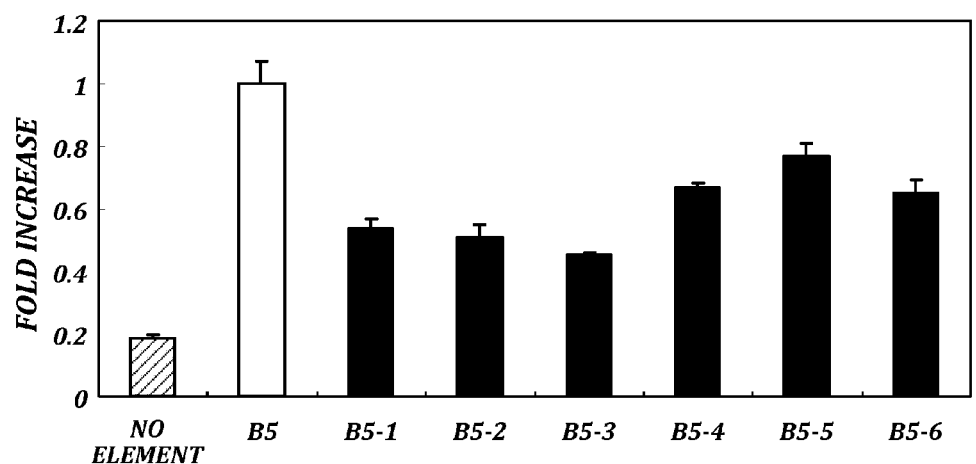
FIG. 13 is a table showing the sequence lengths of DNA element B5 and related sequences.
FIG. 14 is a graph showing the expression of SEAP in a stably expressing CHO cell line either without a DNA element or with DNA element B5 or a related sequence. The effects of DNA element B5 and related sequences on enhancement of expression were confirmed.
Figure 16A:
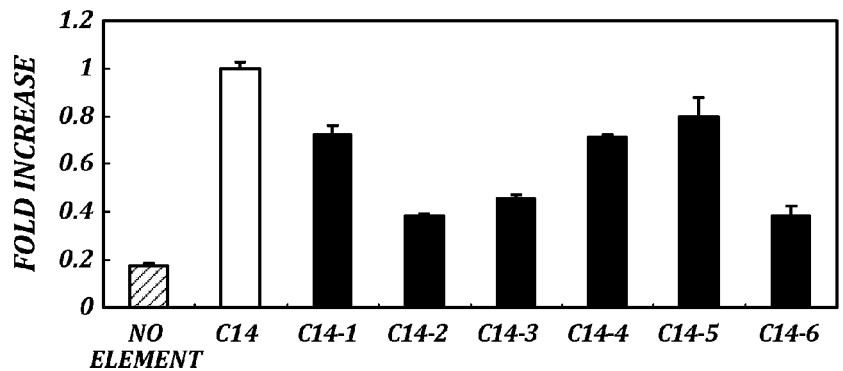
FIG. 16A through FIG. 16C comprise three graphs showing the expression of SEAP in a stably expressing CHO cell line either without a DNA element or with DNA element C14 or a related sequence.
Figure 16B:
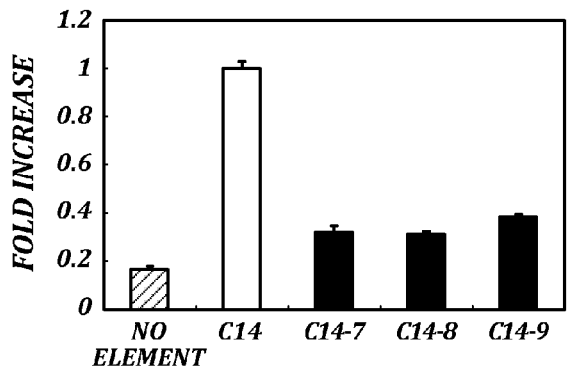
Figure 16C:
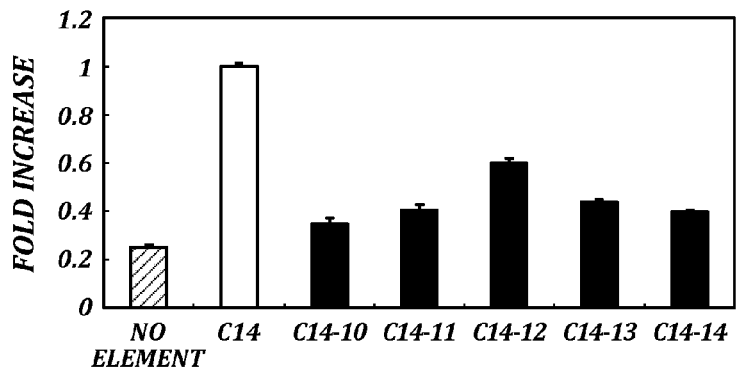

The results are shown in FIG. 6. It was confirmed that the sample having the DNA element A7 has a higher effect of enhancing antibody production as compared with a control with no element when the EF-1α promoter or the CMV promoter was used in the antibody expression vector.

Example 5

Length of Sequence Exhibiting Activity of Enhancing Foreign Gene Expression (5-1) Cloning of DNA Elements Having Different Sequence Lengths Based on the length of the sequence used in Example 2, vectors containing each of the DNA elements but having different sequence lengths were constructed.

The details of the DNA elements having different sequence lengths which were designed based on the full length of each of the DNA elements A2, A7, A18, B5, and C14 are shown in FIGS. 7, 9, 11, 13, 15, 18, and 19 respectively. The pCMV/SEAP ires Hygro described in (2-1) was digested with the restriction enzyme SpeI for several hours, followed by ethanol precipitation, and the precipitate was dissolved in sterile water. By using the vector digested with SpeI as a template, DNA for transformation was prepared by the PCR method (94° C. for 15 sec, 55° C. for 30 sec, and 68° C. for 10 min×30 cycles) using the following primers and KOD-plus-. By using the thus prepared DNA for transformation and the corresponding BAC transfected with pRed/ET, each DNA element having a different sequence length was cloned into the pCMV/SEAP ires Hygro described in (2-1). The vector construct is shown in FIG. 2. Incidentally, the procedure was performed according to the method described in (2-2).

A2-1D:
(SEQ ID NO: 46)
5'-CATGCACAGATTAGCCATTTAGTACTTACTAAATCAAACTCAATTTC

TGAAGTCTAGTTATTAATAGTAATCAATTACG-3'

A2-1R:
(SEQ ID NO: 47)
5'-CTCATTCTGTGGGTTGTCATTTCACTTCCTTGATGCTATCCTTTCAA

GCAAAATTCAATAATCAATGTCAACGCGTATAT-3'

A2-2D:
(SEQ ID NO: 48)
5'-ACACTGGTCAAAGGGACAGGTCATTGTTATGCTGGCAATGCAGGCTG

CTGAAAACTAGTTATTAATAGTAATCAATTACG-3'

A2-2R:
(SEQ ID NO: 49)
5'-ACTGTAGCTTCTTATTTTTTACCTGCAGTGCATTCCTGTAAAAGTAG

TGTGGAGTCAATAATCAATGTCAACGCGTATAT-3'

A2-3D:
(SEQ ID NO: 50)
5'-CTGGAAATTGAGAAGTATCATTCACAACAGTACCACAAACATGAAAT

AAATGTGCTAGTTATTAATAGTAATCAATTACG-3'

A2-3R:
(SEQ ID NO: 51)
5'-CCAAGCTTGTCCAACCGCGGCCTGCAGGCTGCATGCAGCCTGTGAAG

GCTTTGATCAATAATCAATGTCAACGCGTATAT-3'

A2-4D:
(SEQ ID NO: 52)
5'-TCAATCATTTATCAATTTTATCTTCAAAGTCCCTCACTTCAGGGAGA

TGATATACTAGTTATTAATAGTAATCAATTACG-3'

A2-4R:
(SEQ ID NO: 53)
5'-ATATATAAAAGTTCATGTATATATAAAATCATGCAATACACGGCCTT

TTGTGACTCAATAATCAATGTCAACGCGTATAT-3'

A2-5D:
(SEQ ID NO: 54)
5'-CGCATAAAAGGAAAAGCATCCTTAAAATAAACACCATCAATGGCTCC

TCGGTGGCTAGTTATTAATAGTAATCAATTACG-3'

A2-5R:
A2-4R was used.

A2-6D:
(SEQ ID NO: 55)
5'-GGGAGGCTACAGCTTGCCTCTCTAACCACTAAAAGGCATGACCCTCC

TCAAAGCTAGTTATTAATAGTAATCAATTACG-3'

A2-6R:
A2-4R was used.

A2-7D:
(SEQ ID NO: 56)
5'-TCTGGCTTCCCTGGGCCACGCTGGAAGAAGAATTGTCTTGCGCCACA

CATAAAACTAGTTATTAATAGTAATCAATTACG-3'

A2-7R:
(SEQ ID NO: 57)
5'-AGCTGATTTTTACGTTAAATGTAACATGTAAAGAAATATATGTGTGT

TTTTAGATCAATAATCAATGTCAACGCGTATAT-3'

A2-8D:
(SEQ ID NO: 58)
5'-GTGAAGAGGAGGAGATGTCAAAATTCAAAGTCTTAAATGATGTAGTT

TTAAGTACTAGTTATTAATAGTAATCAATTACG-3'

A2-8R:
(SEQ ID NO: 59)
5'-ATGACACTTGATATTGTTGTTTATATTGCTGGTTAGTATGTGCCTTC

ATTTACCTCAATAATCAATGTCAACGCGTATAT-3'

A2-9D:
A2-6D was used.

A2-9R:
A2R was used.

A2-10D:
A2-2D was used.

A2-10R:
A2-7R was used.

A2-11D:
A2-8D was used.

A2-11R:
A2-2R was used.

A2-12D:
A2-2D was used.

A2-12R:
A2-4R was used.

A2-13D:
A2-8D was used.

-continued

A2-13R:
A2-7R was used.

A2-14D:
A2D was used.

A2-14R:
A2-2R was used.

A2-15D:
A2-2D was used.

A2-15R:
A2R was used.

A2-16D:
A2-8D was used.

A2-16R:
A2-4R was used.

A2-17D:
A2D was used.

A2-17R:
A2-7R was used.

A7-1D:
(SEQ ID NO: 60)
5'-AAAAACAAAACTGGAGTAAACAAGATGAATTGTTTTAATAGAGGCAC

TGTATTACTAGTTATTAATAGTAATCAATTACG-3'

A7-1R:
(SEQ ID NO: 61)
5'-ATACAATGTTCCATGTATTCTGTGCCTGAACCTATGCAGCTGATGTA

GCTGAAGTCAATAATCAATGTCAACGCGTATAT-3'

A7-2D:
(SEQ ID NO: 62)
5'-GATCTTATTTTCTAAGTAGTATAGACTTAATTGTGAGAACAAAATAA

AAACTTGCTAGTTATTAATAGTAATCAATTACG-3'

A7-2R:
(SEQ ID NO: 63)
5'-TGTTGTTTTCAGCCACTAAGTTTGAGGTGATTTGTTCTGGCAGTCCT

AGGAAACTCAATAATCAATGTCAACGCGTATAT-3'

A7-3D:
A7-2D was used.

A7-3R:
(SEQ ID NO: 64)
5'-AGCCTACACTACCCTTTGCAGCCTTTGGTAACTATCCTTCTGCTGTC

TACCTCCTCAATAATCAATGTCAACGCGTATAT-3'

A7-4D:
(SEQ ID NO: 65)
5'-AGGAGCTCCTGAATGAAGGACATCACTCAGCTGTGTTAAGTATCTGG

AACAATACTAGTTATTAATAGTAATCAATTACG-3'

A7-4R:
(SEQ ID NO: 66)
5'-GACATAAAATGTAAGATATGATATGCTATGTAAGATATGATACCTGC

CTTAAAATCAATAATCAATGTCAACGCGTATAT-3'

A7-5D:
(SEQ ID NO: 67)
5'-CACTGCTTGATACTTACTGTGGACTTTGAAAATTATGAATGTGTGTG

TGTGTGTCTAGTTATTAATAGTAATCAATTACG-3'

A7-5R:
(SEQ ID NO: 68)
5'-CAATTACATTCCAGTGATCTGCTACTTAGAATGCATGACTGAACTCC

TGGGTGGTCAATAATCAATGTCAACGCGTATAT-3'

A7-6D:
(SEQ ID NO: 69)
5'-TTATTTTGAAGAGAAACTCCTGGTTCCCACTTAAAATCCTTTCTTGT

TTCCAAGCTAGTTATTAATAGTAATCAATTACG-3'

A7-6R:
(SEQ ID NO: 70)
5'-AAGCAGTGTGTGTTTACCTGCATGTGTATGTGAATTAACTCTGTTCC

TGAGGCATCAATAATCAATGTCAACGCGTATAT-3'

A7-7D:
(SEQ ID NO: 71)
5'-ATTGCATGTTCTCATTTATTTGTGGGATGTAAAAATCAAAACAATAG

AACGTATCTAGTTATTAATAGTAATCAATTACG-3'

A7-7R:
(SEQ ID NO: 72)
5'-TTGGGAGGCCGCAGCTGGTAGATCACTTGAGGCCACGAATTTGACAC

CAGCAGGTCAATAATCAATGTCAACGCGTATAT-3'

A7-8D:
A7-1D was used.

A7-8R:
A7R was used.

A7-9D:
A7-7D was used.

A7-9R:
A7-5R was used.

A7-10D:
A7-4D was used.

A7-10R:
A7-7R was used.

A7-11D:
A7-6D was used.

A7-11R:
A7-4R was used.

A7-12D:
A7-2D was used.

A7-12R:
A7-6R was used.

A7-13D:
A7-7D was used.

A7-13R:
A7R was used.

A7-14D:
A7-4D was used.

A7-14R:
A7-5R was used.

A7-15D:
A7-6D was used.

A7-15R:
A7-7R was used.

A7-16D:
A7-2D was used.

-continued

A7-16R:
A7-4R was used.

A7-17D:
A7-4D was used.

A7-17R:
A7R was used.

A7-18D:
A7-6D was used.

A7-18R
A7-5R was used.

A18-1:
(SEQ ID NO: 73)
5'-ATCCCCTGCTCTGCTAAAAAAGAATGGATGTTGACTCTCAGGCCCTA

GTTCTTGATCCTATTAATAGTAATCAATTACG-3'

A18-1R:
A18R was used.

A18-2D:
(SEQ ID NO: 74)
5'-CTAAAGTGCTGGGATTACAGGCATAAGCCACCGTGCCCGGCTGAGC

ATTGGGATCCTATTAATAGTAATCAATTACG-3'

A18-2R:
(SEQ ID NO: 75)
5'-ACTACTTACACATTTCGAGTTTTAAATAAGGCGTTCAATATAGAGTG

AACACCTAGTCAATAATCAATGTCAACG-3'

A18-3D:
(SEQ ID NO: 76)
5'-CAGGCATAAGCCACCGCACCCGGCCACCCCTTACTAATTTTTAGTAA

CGTCGATCCTATTAATAGTAATCAATTACG-3'

A18-3R:
(SEQ ID NO: 77)
5'-CTGATTGACTTTGACCTCTGCTTTCCAACTTTGCCCCAAAGAAAGTT

AGTCACCTAGTCAATAATCAATGTCAACG-3'

A18-4D:
A18-3D was used.

A18-4R:
(SEQ ID NO: 78)
5'-TTCAATGAAACAAGCTCTGTGAGGCTCATTTGTACCCATTTTGTTCA

GTACTGCCTAGTCAATAATCAATGTCAACG-3'

B5-1D:
(SEQ ID NO: 79)
5'-ACATACCCAGAGACACTGAGAGAGACAGACAGACAGTAAACAGAGGA

GCACGATCCTATTAATAGTAATCAATTACG-3'

B5-1R:
B5R was used.

B5-2D:
(SEQ ID NO: 80)
5'-GCTCAATTGTATCTTATGAAAACAATTTTTCAAAATAAAACAAGAGA

TATGATCCTATTAATAGTAATCAATTACG-3'

B5-2R:
B5R was used.

B5-3D:
(SEQ ID NO: 81)
5'-CCTGTGCTGAATACCGTCTGCATATGTATAGGAAAGGGTTAACTCAG

CAGGGATCCTATTAATAGTAATCAATTACG-3'

-continued

B5-3R:
(SEQ ID NO: 82)
5'-TATGTGAATGGAAATAAAATAATCAAGCTTGTTAGAATTGTGTTCAT

AATGACCCTAGTCAATAATCAATGTCAACG-3'

B5-4D:
B5D was used.

B5-4R:
(SEQ ID NO: 83)
5'-GAAAGTCTACAATTTTTTCAGTTTAAAATGGTATTTATTTGTAACAT

GTACCCTAGTCAATAATCAATGTCAACG-3'

B5-5D:
B5-1D was used.

B5-5R:
(SEQ ID NO: 84)
5'-CAAAGATGAAGGATGAGAGTGACTTCTGCCTTCATTATGTTATGTGT

TCATATCCTAGTCAATAATCAATGTCAACG-3'

B5-6D:
(SEQ ID NO: 85)
5'-CAGTGAATTATTCACTTTGTCTTAGTTAAGTAAAAATAAAATCTGAC

TGTGATCCTATTAATAGTAATCAATTACG-3'

B5-6R:
(SEQ ID NO: 86)
5'-GAACAGACAGGTGAATGAGCACAGAGGTCATTTGTAAACCGTTTGTG

GTTAGCCTAGTCAATAATCAATGTCAACG-3'

C14-1D:
(SEQ ID NO: 87)
5'-CTTTTTGGCTTCTGTGTTTAAGTTATTTTTCCCCTAGGCCCACAAAC

AGAGTCGATCCTATTAATAGTAATCAATTACG-3'

C14-1R:
(SEQ ID NO: 88)
5'-AACCTTGGAAAAATTCTGTTGTGTTTAGAAGCATGTACCAATCTATC

ACTCCTAGTCAATAATCAATGTCAACG-3'

C14-2D:
(SEQ ID NO: 89)
5'-CTATTCACTGTCTGTAGGATGAAAAAGTTAATAACACCCTGAGAGGT

TTCGATCCTATTAATAGTAATCAATTACG-3'

C14-2R:
(SEQ ID NO: 90)
5'-CCTTAGATTAGTTTATTGTATTTTTTATCAGCTACTATAAGGTTTAC

ACACCCTAGTCAATAATCAATGTCAACG-3'

C14-3D:
(SEQ ID NO: 91)
5'-CAAGACCCTCAAAATTCAAAAATTTCCTTTATCTTGCTGTAGCACCT

CCTGCGATCCTATTAATAGTAATCAATTACG-3'

C14-3R:
(SEQ ID NO: 92)
5'-GGAGGGGATAGGAAGGGGATGAGGCCTAACAGGTTGATGATCTAGGC

TTTACCTAGTCAATAATCAATGTCAACG-3'

C14-4D:
(SEQ ID NO: 93)
5'-CTCAAAAAGGAGATAATTCCAGCCCCTCGCCTTAAAGAATCCCTATC

AAGTGATCCTATTAATAGTAATCAATTACG-3'

C14-4R:
C14-1R was used.

-continued

C14-5D:
(SEQ ID NO: 94)
5'-CGCTTGAACCTGGGAGGCAGAGGTTGCAGTGAGCCGAGATCACGCCG

TTGGATCCTATTAATAGTAATCAATTACG-3'

C14-5R:
C14-1R was used.

C14-6D:
C14-4D was used.

C14-6R:
(SEQ ID NO: 95)
5'-TTAACTTTTTCATCCTACAGACAGTGAATAGTAAAGCTTTCTGTGAA

GACATACCCTAGTCAATAATCAATGTCAACG-3'

C14-7D:
C14-2D was used.

C14-7R:
C14-1R was used.

C14-8D:
C14-3D was used.

C14-8R:
(SEQ ID NO: 96)
5'-AAATTATTTCCTGGTGGGCAATATTAGAATATGGGGAATGTTTGCTT

CTGAGCCTAGTCAATAATCAATGTCAACG-3'

C14-9D:
C14-4D was used.

C14-9R:
C14-3R was used.

C14-10D:
C14-2D was used.

C14-10R:
C14R was used.

C14-11D:
C14-3D was used.

C14-11R:
C14-2R was used.

C14-12D:
C14-4D was used.

C14-12R:
C14-8R was used.

C14-13D:
C14-3D was used.

C14-13R:
C14-1R was used.

C14-14D:
C14-4D was used.

C14-14R:
C14-2R was used.

As for the polynucleotide sequences of the respective fragments of A2, A2-1 corresponds to the polynucleotide sequence of nucleotides 1 to 3000 of SEQ ID NO: 1 in the Sequence Listing; A2-2 corresponds to the polynucleotide sequence of nucleotides 2801 to 5800 of SEQ ID NO: 1 in the Sequence Listing; A2-3 corresponds to the polynucleotide sequence of nucleotides 5401 to 8450 of SEQ ID NO: 1 in the Sequence Listing; A2-4 corresponds to the polynucleotide sequence of nucleotides 701 to 2700 of SEQ ID NO: 1 in the Sequence Listing; A2-5 corresponds to the polynucleotide sequence of nucleotides 701 to 2200 of SEQ ID NO: 1 in the Sequence Listing; A2-6 corresponds to the polynucleotide sequence of nucleotides 701 to 3700 of SEQ ID NO: 1 in the Sequence Listing; A2-7 corresponds to the polynucleotide sequence of nucleotides 2001 to 5000 of SEQ ID NO: 1 in the Sequence Listing; A2-8 corresponds to the polynucleotide sequence of nucleotides 4001 to 7000 of SEQ ID NO: 1 in the Sequence Listing; A2-9 corresponds to the polynucleotide sequence of nucleotides 1 to 3700 of SEQ ID NO: 1 in the Sequence Listing; A2-10 corresponds to the polynucleotide sequence of nucleotides 2001 to 5800 of SEQ ID NO: 1 in the Sequence Listing; A2-11 corresponds to the polynucleotide sequence of nucleotides 2801 to 7000 of SEQ ID NO: 1 in the Sequence Listing; A2-12 corresponds to the polynucleotide sequence of nucleotides 701 to 5800 of SEQ ID NO: 1 in the Sequence Listing; A2-13 corresponds to the polynucleotide sequence of nucleotides 2001 to 7000 of SEQ ID NO: 1 in the Sequence Listing; A2-14 corresponds to the polynucleotide sequence of nucleotides 2801 to 8450 of SEQ ID NO: 1 in the Sequence Listing; A2-15 corresponds to the polynucleotide sequence of nucleotides 1 to 5800 of SEQ ID NO: 1 in the Sequence Listing; A2-16 corresponds to the polynucleotide sequence of nucleotides 701 to 7000 of SEQ ID NO: 1 in the Sequence Listing; and A2-17 corresponds to the polynucleotide sequence of nucleotides 2001 to 8450 of SEQ ID NO: 1 in the Sequence Listing.

As for the polynucleotide sequences of the respective fragments of A7, A7-1 corresponds to the polynucleotide sequence of nucleotides 601 to 3600 of SEQ ID NO: 2 in the Sequence Listing; A7-2 corresponds to the polynucleotide sequence of nucleotides 3601 to 8420 of SEQ ID NO: 2 in the Sequence Listing; A7-3 corresponds to the polynucleotide sequence of nucleotides 5401 to 8420 of SEQ ID NO: 2 in the Sequence Listing; A7-4 corresponds to the polynucleotide sequence of nucleotides 3401 to 6400 of SEQ ID NO: 2 in the Sequence Listing; A7-5 corresponds to the polynucleotide sequence of nucleotides 1501 to 4500 of SEQ ID NO: 2 in the Sequence Listing; A7-6 corresponds to the polynucleotide sequence of nucleotides 4401 to 7400 of SEQ ID NO: 2 in the Sequence Listing; A7-7 corresponds to the polynucleotide sequence of nucleotides 2401 to 5400 of SEQ ID NO: 2 in the Sequence Listing; A7-8 corresponds to the polynucleotide sequence of nucleotides 1 to 3600 of SEQ ID NO: 2 in the Sequence Listing; A7-9 corresponds to the polynucleotide sequence of nucleotides 1501 to 5400 of SEQ ID NO: 2 in the Sequence Listing; A7-10 corresponds to the polynucleotide sequence of nucleotides 2401 to 6400 of SEQ ID NO: 2 in the Sequence Listing; A7-11 corresponds to the polynucleotide sequence of nucleotides 3401 to 7400 of SEQ ID NO: 2 in the Sequence Listing; A7-12 corresponds to the polynucleotide sequence of nucleotides 4401 to 8420 of SEQ ID NO: 2 in the Sequence Listing; A7-13 corresponds to the polynucleotide sequence of nucleotides 1 to 5400 of SEQ ID NO: 2 in the Sequence Listing; A7-14 corresponds to the polynucleotide sequence of nucleotides 1501 to 6400 of SEQ ID NO: 2 in the Sequence Listing; A7-15 corresponds to the polynucleotide sequence of nucleotides 2401 to 7400 of SEQ ID NO: 2 in the Sequence Listing; A7-16 corresponds to the polynucleotide sequence of nucleotides 3401 to 8420 of SEQ ID NO: 2 in the Sequence Listing; A7-17 corresponds to the polynucleotide sequence of nucleotides 1 to 6400 of SEQ ID NO: 2 in the Sequence Listing; and A7-18 corresponds to the polynucleotide sequence of nucleotides 1501 to 7400 of SEQ ID NO: 2 in the Sequence Listing.

As for the polynucleotide sequences of the respective fragments of A18, A18-1 corresponds to the polynucleotide sequence of nucleotides 1 to 5040 of SEQ ID NO: 3 in the Sequence Listing; A18-2 corresponds to the polynucleotide sequence of nucleotides 1001 to 6002 of SEQ ID NO: 3 in the Sequence Listing; A18-3 corresponds to the polynucleotide sequence of nucleotides 2001 to 7000 of SEQ ID NO: 3 in the Sequence Listing; and A18-4 corresponds to the polynucleotide sequence of nucleotides 3000 to 7000 of SEQ ID NO: 3 in the Sequence Listing.

As for the polynucleotide sequences of the respective fragments of B5, B5-1 corresponds to the polynucleotide sequence of nucleotides 1 to 4001 of SEQ ID NO: 4 in the Sequence Listing; B5-2 corresponds to the polynucleotide sequence of nucleotides 1 to 3200 of SEQ ID NO: 4 in the Sequence Listing; B5-3 corresponds to the polynucleotide sequence of nucleotides 2491 to 5601 of SEQ ID NO: 4 in the Sequence Listing; B5-4 corresponds to the polynucleotide sequence of nucleotides 5373 to 8401 of SEQ ID NO: 4 in the Sequence Listing; B5-5 corresponds to the polynucleotide sequence of nucleotides 901 to 4001 of SEQ ID NO: 4 in the Sequence Listing; and B5-6 corresponds to the polynucleotide sequence of nucleotides 4001 to 7000 of SEQ ID NO: 4 in the Sequence Listing.

As for the polynucleotide sequences of the respective fragments of C14, C14-1 corresponds to the polynucleotide sequence of nucleotides 960 to 4015 of SEQ ID NO: 5 in the Sequence Listing; C14-2 corresponds to the polynucleotide sequence of nucleotides 1987 to 5014 of SEQ ID NO: 5 in the Sequence Listing; C14-3 corresponds to the polynucleotide sequence of nucleotides 4020 to 7119 of SEQ ID NO: 5 in the Sequence Listing; C14-4 corresponds to the polynucleotide sequence of nucleotides 960 to 8141 of SEQ ID NO: 5 in the Sequence Listing; C14-5 corresponds to the polynucleotide sequence of nucleotides 960 to 6011 of SEQ ID NO: 5 in the Sequence Listing; C14-6 corresponds to the polynucleotide sequence of nucleotides 4939 to 8141 of SEQ ID NO: 5 in the Sequence Listing; C14-7 corresponds to the polynucleotide sequence of nucleotides 960 to 5014 of SEQ ID NO: 5 in the Sequence Listing; C14-8 corresponds to the polynucleotide sequence of nucleotides 2994 to 7119 of SEQ ID NO: 5 in the Sequence Listing; C14-9 corresponds to the polynucleotide sequence of nucleotides 4020 to 8141 of SEQ ID NO: 5 in the Sequence Listing; C14-10 corresponds to the polynucleotide sequence of nucleotides 1 to 5014 of SEQ ID NO: 5 in the Sequence Listing; C14-11 corresponds to the polynucleotide sequence of nucleotides 1987 to 7119 of SEQ ID NO: 5 in the Sequence Listing; C14-12 corresponds to the polynucleotide sequence of nucleotides 2994 to 8141 of SEQ ID NO: 5 in the Sequence Listing; C14-13 corresponds to the polynucleotide sequence of nucleotides 960 to 7119 of SEQ ID NO: 5 in the Sequence Listing; and C14-14 corresponds to the polynucleotide sequence of nucleotides 1987 to 8141 of SEQ ID NO: 5 in the Sequence Listing.

The start and end points of the respective fragments on the full-length sequence are also shown in FIGS. 18 and 19.

(5-2) Evaluation of DNA Elements Having Different Sequence Lengths

Each plasmid constructed in (5-1) was evaluated using the host cell CHO-K1 (ATCC) and transfection reagent Lipofectamine 2000 (Invitrogen).

In the same manner as in (2-3), antibiotic selection with hygromycin was performed after transfection, whereby a stably expressing polyclonal cell line was established. The thus established cell line was subjected to medium replacement on the day before measurement, and a given number of the cells were seeded into a 24-well plate. At 24 hours after plating the cells, the culture supernatant was collected, and the activity of SEAP was measured.

The measurement results are shown in FIGS. 8, 10, 12, 14, and 16. It was confirmed that not only the full-length DNA element, but also clones having a sequence length shorter than the full length have an effect of enhancement of expression. Based on the results, it was confirmed that the DNA elements A2, A7, A18, B5, and C14 have an activity of enhancing foreign gene expression even cases where they have a sequence length shorter than the full length. However, they exhibit the highest effect when the sequence length is the full length.

Example 6

Effect Using Host Cells Other than CHO Cell Line

A CHO cell line was used as the cell line in the evaluation in Examples 2 to 5. However, in Example 6 an HEK293 cell line was selected as a cell line other than the CHO cell line. The HEK293 cell line was subjected to static culture at 37° C. in the presence of 5% $CO_2$ using DMEM medium (Invitrogen) containing 10% FCS, and a given number of the cells were seeded into a 6-well plate on the day before transfection. In order to evaluate the SEAP expression vector containing each DNA element constructed in (3-2), transfection was performed using each plasmid and transfection reagent Lipofectamine 2000 (Invitrogen). Antibiotic selection with hygromycin was performed for about 2 weeks starting 2 days after transfection, whereby a stably expressing polyclonal cell line was established. The thus established cell line was subjected to medium replacement on the day before measurement, and a given number of the cells were seeded into a 24-well plate. At 24 hours after plating the cells, the culture supernatant was collected, and the activity of SEAP was measured. The activity of SEAP in the culture supernatant was measured using SensoLyte™ pNPP Secreted Alkaline Phosphatase Reporter Assay (ANASPEC).

Figure 17:
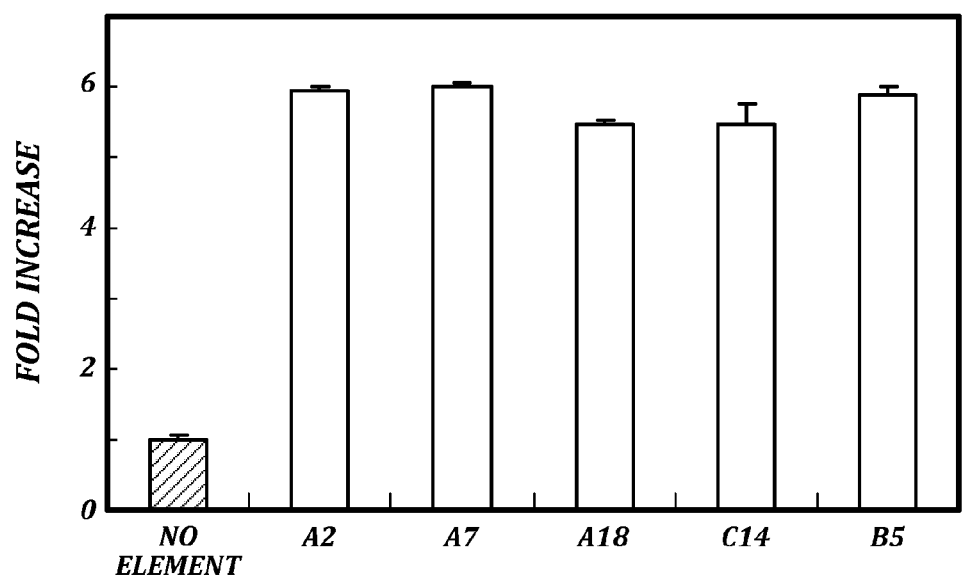
FIG. 17 is a graph showing the expression of SEAP in a stably expressing HEK293 cell line either without a DNA element or with DNA element A2, A7, A18, B5, or C14. The effects of DNA elements A2, A7, A18, B5, and C14 on enhancement of expression in HEK293 cells were confirmed.

The measurement results are shown in FIG. 17. In the same manner as in Example 3, it was confirmed that each element is also highly effective in enhancing the expression of a foreign gene (SEAP) in the HEK293 cell line.

INDUSTRIAL APPLICABILITY

By introducing a foreign gene expression vector using the DNA element according to the invention into mammalian host cells, it becomes possible to improve the productivity of a foreign gene of a therapeutic protein, an antibody, or the like.

The invention claimed is:

1. A vecter comprising a polynucleotide consisting of a polynucleotide sequence having 95% or more identity, or 99% or more identity to the polynucleotide sequence of SEQ ID NO:2, wherein said polynucleotide enhances foreign gene expression.

2. The vecter of claim 1, wherein the polynucleotide consists of at least 3000 consecutive nucleotides of a polynucleotide sequence having 95% or more identity, or 99% or more identity to the polynucleotide sequence of SEQ ID NO:2.

3. The vecter of claim 1, wherein the polynucleotide consists of at least 2000 consecutive nucleotides of a polynucleotide sequence having 95% or more identity, or 99% or more identity to the polynucleotide sequence of SEQ ID NO:2.

4. The vecter of claim 1, wherein the polynucleotide consists of at least 1500 consecutive nucleotides of a polynucleotide sequence having 95% or more identity, or 99% or more identity to the polynucleotide sequence of SEQ ID NO:2.

5. A method for enhancing foreign gene expression in a transformed cell comprising introducing the vector according to claim 1 to the transformed cell.

6. A vecter comprising a polynucleotide consisting of the polynucleotide sequence of SEQ ID NO:2.

7. A vecter comprising a polynucleotide consisting of
a polynucleotide containing two or more sequences selected from (a) to (e):
   (a) a polynucleotide sequence having 95% or more identity, or 99% or more identity to the polynucleotide sequence of SEQ ID NO:2;
   (b) a polynucleotide sequence having at least 3000 consecutive nucleotides of a polynucleotide sequence having 95% or more identity, or 99% or more identity to the polynucleotide sequence of SEQ ID NO:2;
   (c) a polynucleotide sequence having at least 2000 consecutive nucleotides of a polynucleotide sequence having 95% or more identity, or 99% or more identity to the polynucleotide sequence of SEQ ID NO:2;
   (d) a polynucleotide sequence having at least 1500 consecutive nucleotides of a polynucleotide sequence having 95% or more identity, or 99% or more identity to the polynucleotide sequence of SEQ ID NO:2; and
   (e) a polynucleotide sequence consisting of SEQ ID NO:2,
wherein said polynucleotide enhances foreign gene expression.

8. A vecter comprising a polynucleotide consisting of a polynucleotide containing:
(i) at least one sequence selected from (a) to (e):
   (a) a polynucleotide sequence having 95% or more identity, or 99% or more identity to the polynucleotide sequence of SEQ ID NO:2;
   (b) a polynucleotide sequence having at least 3000 consecutive nucleotides of a polynucleotide sequence having 95% or more identity, or 99% or more identity to the polynucleotide sequence of SEQ ID NO:2;
   (c) a polynucleotide sequence having at least 2000 consecutive nucleotides of a polynucleotide seciuence having 95% or more identity, or 99% or more identity to the polynucleotide seciuence of SEQ ID NO:2;
   (d) a polynucleotide sequence having at least 1500 consecutive nucleotides of a polynucleotide seciuence having 95% or more identity, or 99% or more identity to the polynucleotide seciuence of SEQ ID NO:2; and
   (e) a polynucleotide seiuence consisting of SEQ ID NO:2; and
(ii) at least one sequence selected from (f) to (i);
   (f) a polynucleotide sequence of SEQ ID NO: 1, a polynucleotide having 95% or more identity, or 99% or more identity thereto, or a fragment thereof;
   (g) a polynucleotide sequence of SEQ ID NO:3, a polynucleotide having 95% or more identity, or 99% or more identity thereto, or a fragment thereof of either;
   (h) a polynucleotide sequence of SEQ ID NO:4, a polynucleotide having 95% or more identity, or 99% or more identity thereto, or a fragment of either; and
   (i) a polynucleotide sequence of SEQ ID NO:5, a polynucleotide having 95% or more identity, or 99% or more identity thereto, or a fragment of either,
wherein said polynucleotide enhances foreign gene expression.

9. A foreign gene expression vector comprising a polynucleotide consisting of a polynucleotide containing one of at least one sequence selected from (a) to (e):
   (a) a polynucleotide sequence having 95% or more identity, or 99% or more identity to the polynucleotide sequence of SEQ ID NO:2;
   (b) a polynucleotide sequence having at least 3000 consecutive nucleotides of a polynucleotide sequence having 95% or more identity, or 99% or more identity to the polynucleotide sequence of SEQ ID NO:2;
   (c) a polynucleotide sequence having at least 2000 consecutive nucleotides of a polynucleotide sequence having 95% or more identity, or 99% or more identity to the polynucleotide sequence of SEQ ID NO:2;
   (d) a polynucleotide sequence having at least 1500 consecutive nucleotides of a polynucleotide sequence having 95% or more identity, or 99% or more identity to the polynucleotide sequence of SEQ ID NO:2; and
   (e) a polynucleotide sequence consisting of SEQ ID NO:2;
wherein said polynucleotide enhances foreign gene expression.

10. The foreign gene expression vector according to claim 9, wherein the protein encoded by the foreign gene is a multimeric protein.

11. The foreign gene expression vector according to claim 10, wherein the protein encoded by the foreign gene is a hetero-multimeric protein.

12. The foreign gene expression vector according to claim 11, wherein the protein encoded by the foreign gene is an antibody or a functional fragment thereof.

13. A transformed cell into which the foreign gene expression vector according to claim 9 has been introduced.

14. The transformed cell according to claim 13, wherein the cell is a cultured cell derived from a mammal.

15. The transformed cell according to claim 14, wherein the cultured cell derived from a mammal is a cell selected from COS-1 cells, 293 cells, or CHO cells.

16. The transformed cell according to claim 13, wherein the protein encoded by the foreign gene is a multimeric protein.

17. The transformed cell according to claim 16, wherein the protein encoded by the foreign gene is a hetero-multimeric protein.

18. The transformed cell according to claim 17, wherein the protein encoded by the foreign gene is an antibody or a functional fragment thereof.

19. A foreign gene expression vector comprising a polynucleotide consisting of (i) and (ii):
(i) at least one sequence selected from (a) to (e)
 (a) a polynucleotide sequence having 95% or more identity, or 99% or more identity to the polynucleotide sequence of SEQ ID NO:2;
 (b) a polynucleotide sequence having at least 3000 consecutive nucleotides of a polynucleotide sequence having 95% or more identity, or 99% or more identity to the polynucleotide sequence of SEQ ID NO:2;
 (c) a polynucleotide sequence having at least 2000 consecutive nucleotides of a polynucleotide sequence having 95% or more identity, or 99% or more identity to the polynucleotide sequence of SEQ ID NO:2;
 (d) a polynucleotide sequence having at least 1500 consecutive nucleotides of a polynucleotide sequence having 95% or more identity, or 99% or more identity to the polynucleotide sequence of SEQ ID NO:2; and
 (e) a polynucleotide sequence consisting of SEQ ID NO:2; and
(ii) at least one sequence selected from (f) to (i):
 (f) a polynucleotide sequence of SEQ ID NO:1, a polynucleotide having 95% or more identity, or 99% or more identity thereto, or a fragment thereof;
 (g) a polynucleotide sequence of SEQ ID NO:3, a polynucleotide having 95% or more identity, or 99% or more identity thereto, or a fragment thereof;
 (h) a polynucleotide sequence of SEQ ID NO:4, a polynucleotide having 95% or more identity, or 99% or more identity thereto, or a fragment; and
 (i) a polynucleotide sequence of SEQ ID NO:5, a polynucleotide having 95% or more identity, or 99% or more identity thereto, or a fragment thereof,
wherein said polynucleotide enhances foreign gene expression.

20. The foreign gene expression vector according to claim 19, wherein the protein encoded by the foreign gene is a multimeric protein.

21. The foreign gene expression vector according to claim 19, wherein the protein encoded by the foreign gene is a hetero-multimeric protein.

22. The foreign gene expression vector according to caim 21, wherein the protein encoded by the foreign gene is an antibody or a functional fragment thereof.

23. A transformed cell into which the foreign gene expression vector according to claim 19 has been introduced.

24. The transformed cell according to Claim 23, wherein the cell is a cultured cell derived from a mammal.

25. The transformed cell according to Claim 24, wherein the cultured cell derived from a mammal is a cell selected from COS-1 cells, 293 cells, or CHO cells.

26. The transformed cell according to Claim 23, wherein the protein encoded by the foreign gene is a multimeric protein.

27. The transformed cell according to Claim 26, wherein the protein encoded by the foreign gene is a hetero-multimeric protein.

28. The transformed cell according to Claim 27, wherein the protein encoded by the foreign gene is an antibody or a functional fragment thereof.

29. A method for enhancing foreign gene expression in a transformed cell, comprising introducing the foreign gene expression vector according to claim 13 or claim 23 to the transformed cell.

30. A method for producing a protein comprising culturing the transformed cell according to claim 13 or 23 and obtaining the protein encoded by the foreign gene from the resulting culture product.

\* \* \* \* \*

SEQUENCE LISTING

```
<160> NUMBER OF SEQ ID NOS: 96

<210> SEQ ID NO 1
<211> LENGTH: 8450
<212> TYPE: DNA
```

<213> ORGANISM: Homo sapiens

<400> SEQUENCE: 1

| | | | | | |
|---|---|---|---|---|---|
| attttgcttg | aaaggatagc | atcaaggaag | tgaaatgaca | acccacagaa | tgagagataa | 60 |
| tttttgcaaa | tcatgtatct | gataagggac | ctgtagtcag | aatatgcaaa | gaacccttac | 120 |
| aattcaataa | gacaacccaa | tttaaaaaca | ggcaaaggat | gtgaataggc | atttctccaa | 180 |
| agatacggaa | aaacggccaa | taagcacata | aaaagatgct | caaaatcatt | tgccatttgg | 240 |
| gaaatgcaat | caaaccaca | atgaggtatc | acttcacgcc | cattagggtg | gctatagatc | 300 |
| agaaagtcag | ataacatgtg | ttggcaagca | catggaaaca | ctgaagtcct | tacacactgc | 360 |
| tggtaggaat | gtaaaatggt | gcagccactg | tggaaaacag | ttttccaatt | tctcaaaatg | 420 |
| ttaaacacag | ttatcataca | cccaagcaat | tctactctta | ggtatatacc | caagagaaat | 480 |
| gaaaacatat | gtcttcacca | gaacttgctg | ttcacagcag | cattatgcat | aatagaccaa | 540 |
| aagtggaaac | aactcaactg | cccatcaact | ggtgaatgga | taagtaaaat | gtgatgtaac | 600 |
| cagtcattgg | actgtcattc | attaataaaa | agaacaaggt | actgattcat | gttctaacat | 660 |
| gagtgaatct | tgaaaacact | atgctaaatt | aaagaagcca | gtcacaaaag | gccgtgtatt | 720 |
| gcatgatttt | atatatacat | gaacttttat | atatatataa | ttatatatat | tatatataat | 780 |
| tttatatata | taaatttcta | tatataaata | tataaaatca | tatatatgat | atatatttt | 840 |
| tcatatacat | catatatatt | tacaaaaatt | atatatcata | tatcatatga | tatatgagat | 900 |
| atatatcatg | atatatatga | tatatgatat | atatcatatg | agatatatga | tatcatgaga | 960 |
| tatatgatat | catatgatat | atatgatata | gatatcatat | gatatatata | taatatatat | 1020 |
| atgatagata | tattatatat | gatagatatg | atagatatca | tattatatat | gatagatatg | 1080 |
| atagatatca | tattatatat | gatagatata | gatatcatat | tatatatgat | agatatgata | 1140 |
| gatatcatat | tatatatgat | agatatgata | gatatcatat | tatatatgat | agatatgata | 1200 |
| gatatcatat | tatatatgat | agatatgata | gatatcatat | tatatatgat | agatatgata | 1260 |
| gatatcatat | tatatatgat | agatatgata | gatatcatat | tatatatgat | agatatgata | 1320 |
| gatatcatat | tatatatgat | agatatgata | gatatcatat | tatatatgat | agatatgata | 1380 |
| gatatcatat | tatatatgat | agatatgata | gatatcatat | tatatatgat | agatatgata | 1440 |
| gatatcatat | tatatatgat | atcatatata | taccacatac | atcatatata | catcatatat | 1500 |
| acatcatata | tatcatacat | atatatgaac | tttccagaat | aggtatatca | ataaagacag | 1560 |
| gaagtataca | agtggttgcc | acagcctgag | aggagcaggg | aatggtgagt | gactgctaat | 1620 |
| ggatatggca | ctttttttgg | ggggtgatga | aaatgttctg | gtcagacaat | ggcaattaca | 1680 |
| aaactgtata | cacacgaaaa | accaaagaat | cacacacttt | aaaagggagg | atttagctcg | 1740 |
| gcatggtggc | atgcgcctgt | actcccagtt | actcgggagg | ctgaagcagg | actgcttaga | 1800 |
| gcccaggact | tcaaggctgc | agcgagctat | gatcgctcca | ctgcactcca | acaaggatga | 1860 |
| cagtgcgaga | cccgttttct | aaataataat | aataataata | ataataaata | acccaaggta | 1920 |
| cccagttcac | atgcaaaacc | actggtaaac | ataaattatc | tccaagtaat | ctagaaagaa | 1980 |
| aatgagcaca | taagacgtct | tctaaaaaca | cacatatatt | tctttacatg | ttacatttaa | 2040 |
| cgtaaaaatc | agctatgcag | aagttacatg | aacattttat | gttggaaagg | taaatgacta | 2100 |
| ttattaatac | agaatggtta | agtacattta | tgtttttatg | tacaaacgca | taaaaggaaa | 2160 |
| agcatcctta | aaataaacac | catcaatggc | tcctcggtgg | tcacaaaaca | aaatcctcac | 2220 |
| acctttgtct | tccttcacaa | ttgagcttta | tccacctttt | caggcttatc | tcccattatt | 2280 |

```
acctgacaca aacttgggtg ggccagagtt tccactgacc atcccccgac tattcatcca    2340
acactatgtt cactgcctcc cattcctgac catttgcctt ttgtcttcaa ctaattctgg    2400
ggacgttttg tccaaataaa tgatccatat tcttgaaggc tggaatcaag tcctattaca    2460
aatatatttt ctcaccctct ccagagcata gcaacccagc atctactggc tctcacagc     2520 tctaaccatc cacaaccota agctggcttc tcatcaaacg ggtacttttc accacccaaa   2580
ttcaattaat tcactcttac aataatgaag aatagtcgcc tacagcctac cttttccagc    2640
cttgattcaa tcatttatca attttatctt caaagtccct cacttcaggg agatgatata    2700
tcagctttca cccagagtcc taaagaaaac agcactcttg ccaatgacat agtgccacct    2760
agtggcaaca taaggtaaat cacagtggca gtagaaggat ctccacacta cttttacagg   2820
aatgcactgc aggtaaaaaa taagaagcta cagtactgtt tggcaggaca atttgtttca    2880
tacgtgcata ctatcgccct gactaaatta actcgcaagt cttacaggta ttatttgttt    2940
tcagttccat gcacagatta gccatttagt acttactaaa tcaaactcaa tttctgaagt    3000
gtcttacacc aatatattca tgcacatatg gttaaaattt tccttgagga tctatcatgt    3060
gagagtgtgg cttattataa caagtaaaca gaacaaataa atacaaaatg aaaagaaatc    3120
gtatgattta ctcgcatata agggagcttg ttgtggatta agtttcatga cccaggacac    3180
tgaaacagaa atggaataaa tgagaataaa attaaaagtt gtcatcaaaa atatagaagc    3240
catctaaaga cctaggtgtc aagcatagct ctatgagtac aatcccgtgc ctgagattac    3300
catatgccca gctgtatgct atacactaag agatttagga aggaagcggg gtcagggatt   3360
gaccccagac tccatctttt caagtgggga agaaagatct tccgattgaa aaataaaggc    3420
aaaaaaggct tcaccgtcac agaagtttca acaaccaaca ggatatttaa aacagttatc    3480
aaagcaaaac cattgtatgt tcacttacat ttttacatag tccctcaaac tcacaaaatg    3540
ctgtttactc agggacttct tccggtctta ctagggagcc tggaaagtga cgggaggatt    3600
gcaagggacc actagaaccc tcttcctcaa ttcccttct ctgagaaggg aggctacagc     3660
ttgcctctct aaccactaaa aggcatgacc ctcctcaaag ttaatagccg gattccctga    3720
tagatatttt cactaaatga attctcataa aactctcact aagatttaga gaaggcttcc    3780
agggttgaat tcctgaacat taagaacagc atgttttta aaagtttaac ttggtgattg     3840
gaccaggact tcatctaggc tatgaatgct cagaatggta ggtcctttac caaacagctt    3900
gagtttgtgt ataaagtgat ctcatcctct taagagtcag agaaacagaa ccaagcgact    3960
tcactataat ttgatctgag gaagtttctt actcacaata ggtaaatgaa ggcacatact    4020
aaccagcaat ataacaaca atatcaagtg tcattcacac atgcaaaaaa cagacaaaat     4080
cccaaactct gtgttctaac aaatcgcaaa aacctcacta acaataaatt gaaatgacca    4140
aatgtttgga ctgaaaagca atgccttggt agcctagcca tgcctaactc aaataacaga    4200
accatctcga tgttaaaatc ctcacagatc aagctgtgta tgtctcgggt caagacttcg    4260
ccaaaaagca gtgagcacac acttaagagg gaaaaaatct acctcagcct cctaaatgca    4320
atcatctcta cacgagttgc aggccccaag cttcaacgtg ttctgctgga caacgcagta    4380
gaaagctgac aagcaggtgg ccttcccaca ctgactgaac cacctccatg cccatgtcca    4440
ttcattttct tgcccacccc atgtgctata acagacctcc tggctcaggg cactctttcc    4500
ttcctgactg ccttcactta atgactttgt acttttaggt gcaaaaatta tctgcagaaa    4560
tccacactga aaaccaagct tgagaaaggc agcaataacc aacattttta caagaagaac    4620
```

```
aaggtcaata tcaagcccat cagattcaaa tagcaagcat ggatgaaaat gaaagattga      4680
aaggcttgag tgccttctta atgtattaaa tatccattta atttacaatt aagctcactg      4740
tgctcactgg cctttaatc agctttccag gtcctgctca gacttgccta ggacatggga       4800
atgaaagaac ctatacattt atggaccaat ctaccttaac taacttgtca agtgttcctg      4860
catcaagcag aagaaacatc agtgaaactg atacaggaat taacccttg ttaatccata       4920 aaacttaaag gagcgggatc caatcttctg gcttccctgg gccacgctgg aagaagaatt      4980
gtcttgcgcc acacataaaa tacacgaaca ctaataatag ctgctaagct ttaaaaaaat     5040
tgcaaaaaag gaaaatctca taatttttg tttgttgtga ggtggagcct cactctgtca      5100
cccaggccgg agtgcagtgg caccatcttg gctcactgca acctctgcct cctgggttca     5160
agccattctc ctgcctcagc ctcccgagta gctgggatga taggcgtgtg ccaccatgcc     5220
cagctaattt tcgtattttt agtagagacg gggtttcacc atgttggcca ggctggtctc     5280
aaactcctga cctcaggtga tccacccacc tcggcctccc aaagtgctgg gattacaggt     5340
gtgagccacc gtgcccggcc aatgttttaa gaacgtttac gaatttgtat tgggccacat    5400
tcaaagcctt cacaggctgc atgcagcctg caggccgcgg ttggacaagc ttggattaga    5460
gaaatctaca gagacaaact agtgacttag tagccctctg atagctcatg atttgcaaga    5520
aacttaggat gactatgtgt aaagaccaca aacatcaatt taactgaatg gttcccgcca    5580
cactggaatg aggaagctga gcaaactcag aggactctaa gaaagggctg atgtcatctg    5640
aactgttcgg aattataaac tcctctaaac atgtttcaaa gccagaactt gtaggagttg    5700
ttctgataca cggattaaaa gagggatgac aaagtgtctg tccccacac tggtcaaagg     5760 gacaggtcat tgttatgctg gcaatgcagg ctgctgaaaa gaatgtatct gtcaaaagta    5820
atcaaagtaa tgaccccaga aggctccaga aacagactgg taaattcagg ttgcttcag    5880 acttccacaa tgctggcaca caaggggaaa gacaaaacta acatttacag agcattatat    5940
ttgatattac atttaatccc cattaaaaag atactatttc ccgtttcact agtgaaaaag    6000
ttgatctttc aaaggttaaa ttatttaaca ccaaggtcaa agggtaagtt ggagagacca    6060
gattcaaacc cagtctgaca ttaaaacatg tgttttcccc ccacatcgtc tcctgctaat    6120
aacctcaaat ctaaaaactg acttgcccta caccttgagc cccatcctac aaactctccc    6180
tgacgttatt aattcagctg tcactgtgca cctacaacgt gccagacacc atactcctca    6240
acactctgta ggcacagaag gaacagataa aaatccctac cttcatagat attattctag    6300
gggtaacaca ggtaaataaa acattaaaat agttttcaca tagtagcaaa ttccatatag    6360
caaaataaaa cagaagaagg aatagcaaat gagggagatg ccctcttaaa catggtgctg    6420
agggaaggcc tccctgagaa agatatcatt taccccaaaa ataaaaaagc aagtaataga    6480
aaaaacaggt aaaaggtgtt ctagacactt aaacctgcca cattgagaac tcagggttct    6540
gatgcaaaac ctcgctgcat agaatgcatt aacttatttt tatacattta aacaaacaaa    6600
ctctacttaa gaactgtgtt ctaaaggaag gagcatatta caggaaggca atttttggtc    6660
agagtagaca cacttaaaaa ctaaacctat tgaaagacca agaacaactg aaagtctttg    6720
ctttgtcaga tttttgacca aaaggaaaat taaagaaaca caccgtgccc atccaatgat    6780
ttcaccaagg aattttaaga gagaaaatcc tacttcttcc tcacccagta gccagtgaaa    6840
tgactgagca aattcacaag ttcactgggg ctgctttcat gtaacacagg acaacacat     6900 gacagacaca gtggaaccct acaggttgcc tagtatttga aagactgtga agaggaggag    6960
atgtcaaaat tcaaagtctt aaatgatgta gttttaagta tgttcagcaa tttcaccact    7020
```

```
cagtagtaaa gccagctaca gttgaaagca atcagaaatt tgaggggtgt gaaataagca    7080
gaagcacaga agttaaggat ttgtattctt cccacatttt ccactttatt ttatactgct    7140
gagaaaaaac aaatttaata gttttctgct gtataagaga gacacattca ctttatgtca    7200
cagtaagagt cactcaattt taatacaact atctcaatgt ataaattaac attctccccc    7260
ctgcccacac atagtaagtc tcttatgatg ttgctgatta gagaagcaaa agttgccgct    7320
acaattctct tcctgcattt taatataaac aatcatcagt cttttcttca tagagtgcag    7380
tgtgggcact atcatcagaa tgtaccagca ctgggtgtgc aaagtttaca aagattagca    7440
agagcaaaag tgttgagatt tttgaaattc atgctgctgc aaagaagtat gtaaaaactc    7500
actcaccata gaggaccaca cagaaactca ggcatgaagt tatatggctg tgtgagtggt    7560
ttgggagaag gaacggaaag cacttccacc aacctatatg cctgagcaaa ttaatgcaaa    7620
acctcagaag ctacaaaaaa gtttatctac ctaaattaaa attggtgtcc acagcagtag    7680
ccagcaaaat gcctgcgaag cgcaaagtgg taaatatttt agggtctgta ggtcatatgg    7740
tctctgttaa acaatatgta aatgaatggg tgtggctgtg ttccaataaa acttcattta    7800
taaaaagagg cagcatggta catccagtca gcaagctata atgtaccaac ccccggtcta    7860
acactaacca aatacctctt aataagccaa agaaactgtg tcctcttagg ccggaagcgg    7920
tggctcacac ctataatccc agcattttgg gaggccgagg cggggagatc acctgaggtc    7980
aggagtttga ccatcctg gccaacatgg tgaaacccta tttctactaa aaatacaaaa    8040
attagccagg cgtgctggcg ggcgcctgta atgccaacta ctggggaggc tgaagcacga    8100
gaatcgcttg aacccaggag gcagaggttg cagcgagcct agatcacgcc attgcactcc    8160
agcctgggca acaagagaga aactccgtct caaaaaaaaa aaggaaaata aaagtataca    8220
aagtgaaaac aaagaaatta aactgccctt atttgccagt gacattactg tctatgcaca    8280
aaattccaaa aatctacaaa aaagcttcta gtactaaaaa tgagtttagc aaggttgtag    8340
aatccaaggt cagcatataa cataaaatca ccttcctata tactagcaat caccaactgg    8400
aaattgagaa gtatcattca caacagtacc acaaacatga aataaatgtg              8450
```

<210> SEQ ID NO 2
<211> LENGTH: 8420
<212> TYPE: DNA
<213> ORGANISM: Homo sapiens

<400> SEQUENCE: 2

```
tcttagtatg gtaaaccttt tgaagtagat tcaaatgaga atgggaagag agaaaaggga      60
gagaagcaac ataagaaatc tcttttaagg aattttatat agagagaaac agaggaatca    120
gttgatagtt ggaaattatt ttaaagaaaa tgggttattt taaagaaaaa aggtattaca    180
acatgtttgc actattgtgg gaataatcaa gttgagacag aaaattattt tttaaggaag    240
agtctaattg ctgaagtgaa agagaatgaa tgagaccctg tgcataagtg tgatcagata    300
ggagcatgta cagctcaagt aagaacagga agaaagagac aataaacatg tacagatagg    360
atgggctggt cgatgtggtg gtgaaaagac atgcgagtta ttactgatta cttctatttc    420
cccagtgaaa taggaagcca ggttcataaa ccaaaatgaa gaggagcgag gcagtattgg    480
aagttcagga aaagtaatag gtgtaaaaat atgtaaagta gaattaccag ggagtatgaa    540
gatacatttc caattaagga tgaagaattt aaagtgaggc cagccaatac ccctgctttg    600
cttcagctac atcagctgca taggttcagg cacagaatac atggaacatt gtatttaaat    660
```

-continued

```
agggcctgga ttttacaaaa gtaacacaat gaagaagaga gatgcaaggc tatttgaggg    720
tgtttgtggg agagattgta aaatattagc taagtaagaa ggggactgca aattttagtg    780
gtataaagga atgaggaaaa gtgtaaatac agtggggtca agaatgtttt ggagccaagg    840
cactagaggc aattagctga aaatgtaggt gattattggt gagtgacatg gtttaaatga    900
aaagtataga agggtacaat tatccatcat gaaaagttct agggtacaac taagatctga    960
gtagctgaag tagaatgaaa gtagaatgga ccttttccata tccagccagg ttcagtgaca   1020
gaaggttagg aaacaaatta taaaccactt gagagaacat atcccctaag ttgttttttgc   1080 tattttctt tcagcatata tttgttggaa tgccaactat gttcagttca attaatatgg    1140
gcttcttaaa taagggctcc agcactggat aatcctgcca tttattttga tacattccat   1200
cctgctgctc agatctattg gcatctacag gatgtctttt gagaagatgg gcattcacat   1260
ccctatgtcc tagcaaattt ccaactcaga aaaccacatt aggcttctct atatatcttc   1320
caactatttc aatggaaaat acaattctct gatttcttcc tatgatattt atcaaagaga   1380
atggtgcctg ccagttctag ggtgggggaa ctcaatacaa atcaccaacc tttagatgac   1440
accctgtctt caaagtgctt tcaaagtctg gcagaaaaaa agtacccagt ggctataaga   1500
ccacccagga gttcagtcat gcattctaag tagcagatca ctggaatgta attggctagt   1560
gagttcattt tactcttctc ttcttggtca catgttaccg cccttgtacc ctgcacgttc   1620
tctttcccag acttacaaag catgttctct tgaattcgtt ctcttttaa attcacacag    1680 tcttaatgat tcttctttca caagagtctt tcactcttac aattcagttc aagtcatcca   1740
catgcttatt atgagcaagg gtctgggact taggggaaaa gggaataaaa agatgaatga   1800
aatgtgatcc ctgcagtcca agagcttgct gtgaaaaagg aagtttggct tacattgcct   1860
ccctaatccc ttggctaggc cagaacagaa tattgtctaa aacctcctca cgtcagcagt   1920
cctctggggt ggtgactgga agtagaattt aaacaaaaat ataattgaca cataataatt   1980
gtgcatactt atagggtaca atctgatgtt tcgatatgtg tttaaatggg tgcattgtgt   2040
aatgatcaaa ttgaggtaat ttatccacca ccttgaagag agattttca atattctcat    2100 tgcgaagaag caggaatttt tagcagacaa ctgagatgcc tcttgttcac actaagtcat   2160
tctgacgatg gatttacata acttgttgtt tttttgtgt gtgtgttttt gagacagagt    2220
cttactttgt cgactaggct gaagtgcagt ggcacaatct cggctcactg caacctccac   2280
ctcccgggtt caaacgattc tcctgcctca gcctcctgag tagctgggat tacaggtgca   2340
tgcaactagg cctggctaat ttttatattt ttaatacaga tgggatttca ccatgttggc   2400
cctgctggtg tcaaattcgt ggcctcaagt gatctaccag ctgcggcctc ccaaagtgca   2460
gggattacag gtgtgagaca ccaagcctgg tacatttaca tttcttatct ggatcttttcc   2520 tttagtaagt gctaaggaat cctacttccc ccaatatttt ttcctatttc aatgttttag   2580
catgtatcat gttactactt tgcagacatt tgattttccc ctttgtttac tgtaaagtat   2640
atttttatag cctttgtaat agaagtattc taaaatctgc ctgcaaccta tctttctgac   2700
tctgcatttt agggaataat tctctgttgt ggaatgaaaa aaaaaacaga gcctgtggag   2760
tcagagatct catttcaaat tatagttatc cctaggaata atctgagtg acaggtagta    2820 tagtataata ataagtataa agctatggtt aaggaaaact caacaacctt atctgtaaat   2880
tgggatgaca acagcctacg tcaaaaaaat gtgaaggtaa atgagataat gtaaggctga   2940
tacttagtaa gcaatttaaa aacacccaaa aaactattgc catgattact ctacttactc   3000
tatttctcta tgctccaggc aaatgaacta ctaatgaccc aggggtcctt ccccattctc   3060
```

```
ttcttcacaa ggaaatattc tctctctgtg tgctgtttat taaaatctac tgcccctttt    3120
agaagccttt ccagatcatc ccatggccaa gaacgatcgc tgcttcctct tctttacata    3180
cagatgtttt tctcctgctt gacaattatt tttgtgcaat tattttcctt ttgattgtgt    3240
ttttaatgtc ccccccaccc cacaattttc cagactgttt gctccacgag agaggagacc    3300
atcatctctg tgctcaccgt tgtatgacca gtatcctgag gagtggctgt tacataatta    3360
catcaggcac tcaataaaaa tttgatgaat aaacactgga ttttaaggca ggtatcatat    3420
cttacatagc atatcatatc ttacatttta tgtccctcac ataaatacca cagagtgaag    3480
tatatgacag ataaggtcat ttctcttgat aagtacatag tccagtctga aacagatatg    3540
ccaaaaaaaa acaaaactgg agtaaacaag atgaattgtt ttaatagagg cactgtatta    3600
gtttcctagg actgccagaa caaatcacct caaacttagt ggctgaaaac aacaaaaatt    3660
tattgtctca cagttataga tgttagaagt ataaaattaa ggtgtcagtg ggattggttc    3720
cttctggggg ctgtggaaga gaatctgtcc caagccttca cactgtaaag tacagtactg    3780
gagggatagg acttcaactt gctctatctc agatagagag gagccatttg ttgtgaattg    3840
agaagagggg tatgttgaat ccataataag cacataaaaa cttggctggt tcataggaga    3900
agtaacatgt ttccagctct agtaaaaaac aaattgaagt ggcctataaa aaggtacaga    3960
gtacgacaga atgaaaaata aatgaacaag aatacagaga ggatgtggta aattatcatg    4020
tttccctaat atgttattgg acactaaatg gtattagaat tatttatcaa taataattct    4080
aaactgttgc aattgaaaga atatattaag tggtgttata tgagaagtgc cagggcattc    4140
tcatttctgt ccaatgggag aaacattttc gtttgagacc tccgtgaata atacagtctt    4200
ttagttagga gagctgcatt ttgagtggtg caggcagaat ggcgatctct cacccacaca    4260
aacactaaga tagagagaga cagagacaga gacagagaca gcagagagag acagagaaag    4320
gaagtacagg tactcagata gagataagcc atttcttgac attaagaaat aaagtagaat    4380
ccattggagg gaaataaaac tgcctcagga acagagttaa ttcacataca catgcaggta    4440
aacacacact gcttgatact tactgtggac tttgaaaatt atgaatgtgt gtgtgtgtgt    4500
gtgtgtacat tcagccctcc atatccatgg attttgcatt cacagattca accaaccatg    4560
aattaaaaac atttggaaat aacaaacatt aaaatataac aatacaacaa taaaaataat    4620
acaaataaaa aatatagtgt aacaactgtt tacatagcat gtatgttgta ttaagtagta    4680
taaatctaga gattacttaa tgtataccag aggatgcata ggctatatgc aaatactatg    4740
ccactttaaa ctgataagaa cagatactaa acttcatctt agccaaaagt cagagaaaca    4800 ataaactat gccattttac ataagggact tgagctgagc atcctcagat ttcagtatct    4860
ttggagttcc tggaaacaat tccttgtttt atatatatat atgtgtgtgt atatatatat    4920
atatatatac acacatatat atatatatat atatatgata gctactgagt gacaggtgat    4980
attataccat accacttgtc actcagtagc tgtatatgca tatgtatata tacatatata    5040
catatatgtg tgtatgtgta tgtgtgtgtg tgtgtgtgtg tgtgtgtatg ctgtctttcc    5100
tcggtatcac agggaattgg agatatatat attcttttca gtacaaaaaa aattgaacac    5160
agatgggtat ggtaccagaa cagaaggtaa agacacatga aaaaaatttg caacaacatg    5220
aatggaactg gagatcatta tttgaggaga aataatccag gcacagaaaa acaagcattt    5280
tattatttta ggtgaaagac aaacatttta ttttaggtga ataatccag gcacagaaag    5340 acaaacattg catgttctca tttatttgtg ggatgtaaaa atcaaaacaa tagaacgtat    5400
```

```
ggaggtagac agcagaagga tagttaccaa aggctgcaaa gggtagtgta ggctttgagg     5460
gtgaggtggg gatggttatt gggtacaaaa aatagttaga aagaataaat aatatctagt     5520
atttaatagc acaacaggtt gactatagtc aaaataacat aattgtacaa tttaaatatg     5580
aaattaaata tatatacaag actagaacac caagttgaat gactccagct tgcgaaaccc     5640
acattgatca ccatgcttgc cccaagggaa gctgtacaat gtctggctcg tccagaaccc     5700
catcatttat cactagcaat ctattgtcca taatcatgtt taaattaata gcattttaaa     5760
ggtacaaata ttttttaaaa aacaaataat tatttaattc gccttttaaa agctttttaa     5820
aaacgttttt aaaaacttttt ttaaagtcct gaggactatt ttctttaaag tgctcagtta     5880
cagagctcca tatattgggc tatgatagcc ttacctgatt cttgccaaga atctagtgcc     5940
cagaaaatgc aaatacaaag taagcaactg aaaaataaac aaataagttg gaggtatgct     6000
acctgttgaa atatgaccta gcgcaaacac ctatgccact tgcttatgaa atcatatagg     6060
ttttcggtgt gcagttttga ctgaatgagg gagtttacgc tggaccacaa gggggcccct     6120
ctgtcaataa cgtactccat ttgtgtatta agtcaaaaat gaaatggaag agaaaagaaa     6180
catcgatgac cccaagtctc tttaattgaa tggaggtaaa agggaaacaa cgaatgagaa     6240
aagtactctg cccttttaag aatcttgcat tcacattcct gatgaagtta tttttcctcc     6300
tctcactgat tcccatttca ctctattaca tagcaccgtg ttccccagga gctcctgaat     6360
gaaggacatc actcagctgt gttaagtatc tggaacaata aatatactag tttcaatgtc     6420
taggctatgg gtattccttt ttactgaagg tatgacatat agctgcccag gctgactaa     6480 attaatagta ataataatta ataatggcaa attttattc tattaagtta cttggcttga     6540
cttgtagaaa tagcaacatt catctgaaat gcccctcct acacttatgt ctaaggacaa     6600
atcccacata caccacagat aacttcattt tacatgtttt attctgttac caaactaaat     6660
ttttatcata tagtctgttg ctcactgaac tcttcagtaa ttctcaacat accatgtaaa     6720
gcattaagca cagttccaac acagagcaaa tgagcaataa ctgttagtta ttataacatt     6780
attatgtgtt ttcagtgcat taaaccactg gtctgatacc tagcccaaca ttctattaaa     6840
ccacataatc cagttgaata atatatgata atataataaa atggcgataa gtgctaaata     6900
tccagataga aacacagatg gaatcagaca gctttcccaa gaaatagaga aaatagtaga     6960
taggcgatct aggcctaagc actctaagca gaagctaagt tatcacagga tatcttggca     7020
atctgtggca cgtgaaccct tttcttctgg agtctggaac tatgttgcaa ctctcacttt     7080
ctccctatct agagactcag tttgttccct tgtgattatc agcagttgag aaatccttag     7140
accttctgaa aggactactt tttaaattta tatatataat atttaaaata catatcttta     7200
tatataatat atatttaaat atataatatt taaattaata tatatttaaa tatataaatat     7260 ttaaattaat atatatttaa ataaataaat ttatatttaa atatataata attaaaatat     7320
atttttaatg aacagagagt aaaggattat tttgaagaga aactcctggt tcccacttaa     7380
aatcctttct tgtttccaag ttttttcaaat ggagccctct ttaccagctt gcccccctcag    7440 agataagctg ttcccctact tattcagatc tgagatctga aaacattcct tttcctgtga     7500
gttcagctag gacaaagatg gagcttttg ataaaatttg gcaaacacat ttttttaaga     7560
tgaaaatttt taaaaattga aaaaaaaaca tttatagaaa gagacttcta atccaaattt     7620
aacttctcaa actatgtttt gaccggctag cataatgttt cagtcttct ggagaatgcc     7680 ccttgaaact gttttcttct acacaacttc ctccctttcct ttgactttcc tgctctggaa     7740
gggaagaaca ggaagaggac agatcaaatt actcaagagg aaggacaaga aataaggaac     7800
```

-continued

```
caaattatca acaattggag aaagaaagct gatgtcagta tcatttcata tatgattatg    7860
tcagagtcag gtggataagc caatcctgtt gaatagcata cttttcctgc tactcctgaa    7920
gggtaaagag gtctttctct tacaaagccg tcctagctag taatcttaca ggtgcaaaaa    7980
gcttgttttc atgttatttc ttagtaactc aaaatacctc taaagttata catattatga    8040
aagtactaca gtcacagtgc tgagaaaagg agtaaataag acaatgtata taaaaacact    8100
tggctcagcc cctggctctg tggttgataa atattaagtt agtattcatt attattataa    8160
tttccaaaga gtccattaaa agatatagaa gaagggaggc agcaataaca ctaagagaaa    8220
attccattat ctccaactat ttatcctcta gcccaaaata attgccatta gaagagcaa     8280
cttaacaaa aatttaagt tgcaatagat gttcaacttt aaatccatcc cagaaaaatt     8340
tctaaccaaa ggagcataga agatttgatc ttattttcta agtagtatag acttaattgt    8400
gagaacaaaa taaaaacttg                                                 8420
```

<210> SEQ ID NO 3
<211> LENGTH: 8475
<212> TYPE: DNA
<213> ORGANISM: Homo sapiens

<400> SEQUENCE: 3

```
gcataacttg taagaaatgg agtgaggtct cagttcaaac tggcttctgt atgacttcaa      60
agccaaagtc agcaacttag aaggcaaaaa ttataattta gttggcaaat acgagaaaag     120
gtcagaaaca catgaaatga agctcaatag gaacacttac agggtagcag ggtagtagcc     180
tagggaaaaa agtcagacac taaaattgtt taaataggta agttcaaggg acaggtaaag     240
accttagtgg gtaagaagcc aatcagcaga cgaactgcaa gcaagcactg tctctctttc     300
ccttctgtct cctcttgtag taactgacca caattaaggc tgcctagggg aataatgaag     360
taatcctcct attatcagca atggtctgat ccagtgccag gcaccacaga caacttggtg     420
ttcagagaag atccttcaag atgaacaaag ggtcaaaata aaaaattcta gaagagagaa     480
gactgatcac aatttaatgt aaggcttgga aggaactgat ctctaccttc cttaacatct     540
caagaacttc ctcagattca ttggatgttg agtgtgtgtg agtctagtag aaaaatgaat     600
ttttgtttct taacttggat atgtgattag gatgttaata attaagtctg gctaatatt      660
gaaggtatct tatgatgggc ttcttaaagc attgatcaca aagactgcat gttcataaac     720
tgagctgcac ttgttaggat tctagatgtt tgaaatttct tgtgttattt tggtctcaga     780
tttctagaca aattttctca aattcctatt tcacttttg acatatcatg agtgactcaa      840
atgtttgccc ttgagtcgga aaacacccag cattaggaat aggcacataa acataatact     900
tcaagcttca gatttaagct caattataaa gtgtttaaag gctgtgctga tagttcttct     960
gagtagaatt cctacaacta tgggtttgtc tataataaaa tgttcactct atattgaacg    1020
ccttatttaa aactcgaaat gtgtaagtag taataaagaa aatatgtcct cctgtaacca    1080
aagctaggac cgattacatg ttcacttgac tgacagatac aatcacctat attaggagca    1140
atcagcactt ccttacaaac taacaacttg agatgtagtg ttcccattgg ctatgaagat    1200
tttcttatt tactcagaat agtctgtagg atctgccagc tgcccctgat tataccagct     1260
gcacccaatg atcacagtga acattatttt acattctaaa taactggtgc aaggtgagcc    1320
atggttttct gagtttccta tcaccttgt gtttcaggtc ctcaaatgtt aatttgtaaa     1380
gctgctgttt caggcaaaac taacaaaatt agcatctaat caataaccat actatgtcca    1440
```

-continued

```
cccatatcct ataacacaga agtaggggaa gagtgagaaa ggtggaagtg gagaaataga    1500
ggcccaaaaa gaaagtttta tcacaggaat atctagatgt cttctgggat tgtctgttaa    1560
agagctgtga cactcatata aatgcagaat tactctcttt cttccttgtt ggttagaagg    1620
ccaagggtgc catggtaata ctaccaaaca tatatcaaag cttggcagga aaaatggtac    1680
cttcagaaat tttataatct gatatcaaat aggtcaagaa atataataaa actagtttct    1740
ttggtttcct tagaaacctg gaaaacttta aattagaaac ttagaaagct ttaaatcaga    1800 cttttgtagtt aaaaaaggaa attttagttc cttccagcat tagaattccg tgattctctg    1860
actctgagcc tggattaaat ctagcccagc tgagtggaaa cttaagtaac tagctggttg    1920
cctttagtga tcttccactt tatggctgct tccgcctaag aagttcatca tcgtgactta    1980
ctttctttgg ggcaaagtcg tgactaactt tctttggggc aaagttggaa agcagaggtc    2040
aaagtcaatc agaaatggga caaactcact tcctactgcc tggtgaaggg gccattttca    2100
gtagcccctt ttcaagatta gtttcattca agatttgata agctgttttg actttactat    2160
agatcttatt atccatgtca gttaagttta tgcttccact aaatctatct gaattcaaaa    2220
ggtaaaaagc taatgctcag tcttatcaga tttatcttat ttattaatag aatgtggatt    2280
tttttaagca tataacaata atagtaatga taggaccata aatgtggatg gctctttaca    2340
agtcactaac attacataaa ttcctcaaca acacactctg aggccataac aaacttttag    2400
aaataacaca attggctacg gaactccagc catctagctt catgggctcc cactttaatt    2460
tcaaaacaac agaactgtgc acattcattt acatgattag ggcagagctt aactgtatct    2520
catgtagcac ctacatcatt cttcagacaa acttattgcc ttttacagac aagaaaactg    2580
gggctcaaaa aaggacttgc ttataactgg ctaataaaga ggaactctgg gttcaaagtg    2640
agtccaattc tttcttccac ccacagcttc tgctaaagtc attacagaaa tgcatagagc    2700
agttcttcca cgttattgct taggtttcta aagagcagtg acctaataca acatgctcta    2760
taatttatta ctgatttaac tatttcacta aggattcact tttaactttt aacttgtaaa    2820
tatgtctaat aaacaccact gaaatagcaa cctctttctt catggccttg tggttgtaaa    2880
gcaagctagt aatatatgtc tgtggatttg tgctaataaa gttctataca cctcattaat    2940
tccacaaatc ctactgggta tttcttatct gccagatcct acgctaggta ctggatacac    3000
agtactgaac aaaatgggta caaatgagcc tcacagagct tgtttcattg aaaagcagag    3060
agatacacac taatcaacaa attaatagta acacactacg atgtgttttg aaggaaaatt    3120
agagcatcaa agagacggtg ttagcaggtg gaggggagct cttttagatg gagaatgaga    3180
atgcctccct aaagacatgg gaataaattg agatcacaaa aaatgagaaa tagccagcct    3240
tgagaagagc agaaggaaga acattcaaag gaaaagaaag tgcatactgg aaagcctgaa    3300
cactagagtt tggtgtatgt aaggagctga gcaatggtca cttgtgtgat aagatgtgtg    3360
gatgtggggt gggggggcagg ggtgagtccc acgcagctct taagtgtgtc ctcagactcc    3420
tgtggtttcc atcagccaca acctgaataa ctgtgtggta atccaaaaat gattacagat    3480
taaacatata aaatatcat tacacccata gtacctaagc caaggacaca gtattctatc    3540
ttttcaatga agatctgcat gaagtaaaat tattatatat aatttaggt attgatatag    3600 atacatcagt ggatagatat agatatgtgt ctctggtata gaaaaaagtt ttaaagggat    3660
attaaaagtt cttatcttgc agggttgaag attgtggcaa ctttcatttc ttttaatttt    3720
taagaaaaaa gtggtattat gggggattag catgtttgtg ggtatatgta tatttttaat    3780
taaaaaataa acaacaaaat gaaaacgttt ttcttctatg aaagcctaat aagaagaaat    3840
```

```
ttcagctgtt ttaacttagg gagctaaaaa catcaaatcc aagaatgttc tctggaactg    3900
agctcaatac attttatttt gagtaagaat tggatacatt tccatcccct tggggctcca    3960
gtctgtcaat attttacttt tcagcgataa aaagacacat gtagataatc acagtgacct    4020
cagtaacttt ccttctctta tttaagttta ttttatttct atcgtagttt tccctgttaa    4080 agatttttc ttttgctta catatataat tttagagaat aacaatgcac acacaaaaaa    4140
ttcctcttgt tctgctagac ctggactttt tctctaatat atatctccat tttttgtctt    4200
ttttcagacg tattttggaa gcaaaggaga gaattgctat atagctgact tcctcttctc    4260
atcaacagtg ttttaacagt ttttaagcaa aagtcagctt tgtttatcta agattttttt    4320
tgctggcatt taacctaccc ctgcctcccc tttcccaagt ccacttcagc caacctctca    4380
ttcgacaggt accaccctct aacataactg aaataatgtc taccattact ggatcttgct    4440
agcaaagaat ctcaaatttt cccacttggt tgtaaattat tttgtaatct ctagtgttta    4500
aggtgcgctt gtcctatcta atcccctccc tggcaggaca ccttacagaa cctacccctt    4560
acactagtca ttaagcacca tcagggacgg atggctgtgt cactggtctg tttggtattc    4620
cctactgatc ctaccatgtg gtgattatct atgacttccc taatccctgg ctgccttagc    4680
tgggactggc tgacatgctt ctcaggttgc cgctggcttt acagtccttt actgcccatg    4740
ccactttgga gataggcagg gctagtactt ttctatataa gccccaaac ttgactttgt    4800 gtttcacagt aggtgaaaaa gttgggtctc tttctttta cttttctttc cacaagatga    4860
taaagctagg ggaagcctgt ggacatggtt tatttctgca actgcaatga ttgattggtg    4920
cttcctgctg cttacttcct aaactttgtg ctcagtgtca gatccctagc agtttctatc    4980
ccctgctctg ctaaaaaaga atggatgttg actctcaggc cctagttctt tttaattaaa    5040
ttgtattttt gttatcatta ttattattat tattttgaga tggggtctta ctctgtcgcc    5100
caggctgaag tgcagtggtg caatcacagc tcactgtttt agcctcctga gtagctggga    5160
ctacaagcgt catgccacca tgcttctttt taattttttta aaatggtttt ctgccttcaa    5220
ttctaagcac ttctcaattg taaccaagag ataatacttt ttatgaattc ttaaagttat    5280
caacagatac tcaaagtttt agcaaagtct aaatgatatt aagcttgtcc ttattgccca    5340
agtgacttca atgactattt gttaattgca accaagggtc atttttaaa tgaatatata    5400 ttattattat atatataata ttaaggtcct caaatcccta aaagtttagc aaaatctaaa    5460
taatattgtg catattcttt tattactgta ttagtccgtt ttcatgttgc tgataaagac    5520
atacccaaga ctgggcaatt tacaaaagaa agaggttcac tggactcaca gttccacgtg    5580 gctgggagg cctcacaatc acggcagctt acggattgt tgagaaatga cacttctcaa    5640 gctgggcta aactatctct gtggtagttg ttctgattca agtattgaat ggttttttt    5700 tgttttttt gagatggagt ttcgttcttg ttgcccaggc tggagtgcaa tggcacgatc    5760
tcagctcacc gcaacctctg cctcccgggt tcaagtgatt ctcctgcttc agcctcccaa    5820
gtagctggga ctacaggcat gagccaccac acccagctaa ttttgtattt ttagtagaga    5880
catggtttct ccatgttggt caggctggtc tcaaactccc aacctcaggt gatccacctg    5940
ccttggcctc ctaaagtgct gggattacag gcataagcca ccgtgcccgg ctggagcatt    6000
ggtatataaa agctgcctag gtaactctaa ccttggccc catacatctg aaggatacct    6060
acaatgcacc tgaaaaatgc aactgaaaca gtagttccct gggaccacac actcagaaag    6120
ggggtgtatc aggagatcta gggaccagga gggtggaaga cctaaggcag cactacagat    6180
```

-continued

```
gatggagaaa aacccactgg ggaggggcga tcctaacctt gagaatcact gagatcatgc    6240
agaagtattt gatcctacag cattaatatt gtattgtatt gtattagtat atatatatag    6300
tgtatatata tagtattagt atatatattg tattgtatta gcatatatat actaattgta    6360
ttgtattgta tttatatata tagtattgta ttagtatata tatacagtat atatgtatat    6420
atactaatac aatgtactaa tacaatacaa taccatatat atatacacta acacaataca    6480
attagtatat atatatatat atatactaat acaatacaat actatatata tactaataca    6540
atatatacat atatactcac caagacatat tagtggtctg atgtctggct gccacactca    6600
tcttctacct tcagctctgc tctaccaaat atcatttgtt tctgggatct ttgcagtcca    6660
aggaacttca tccttgatat cccaccccct actaactttt tttttttttt ttttttttga    6720
gacggagtct cgctgtgtca cccaggctgg agtgcagtgg tgtgatctcg gctcactgca    6780
agctccacct cctgggatca caccattctc ctgcctcagc ctcccaagta gctgggacta    6840
caggtgcccg ccaccacacc aggctaatgt tttaccgtgt tagcaaggat ggtctcgatc    6900
tcctgacctc atgatccatc cgccttggcc tcctaaagtg ctgggattac aggcataagc    6960
caccgcaccc ggccacccct tactaatttt tagtaacgtc caaggattaa aggaaatttg    7020
ccttacctat ttaacaggaa tcaacagggt taatctcact cccttcctaa aaataattta    7080
taaacattgc agacaatctc atctatccct gtctaaactg tgtgaattac tgccatttta    7140
atgtaatcag tctactcatt tagtttgcct aaggaatttt tgaaaaaaca gttaaatgaa    7200
tgacttaatg gaataaccag gaagttgaag tctccaatag taagaatgaa ctcttgctct    7260
ctggataatc aaatgggtcc ttcctccttc aggtagatca tgccatttcc tcacttacac    7320
tgaacaggta aacaacataa ttactgactt caacttctag ttaattcctt cttttatcac    7380
tgagtatcct ttggctggga gttttgttgg ctatgctgcc atttttttcta gttatcacag    7440
tcctataaca taccaatcct tcaatataac tcatctttaa attgtggttt taccttctca    7500
agaagttatt aattatgcca gtgctaaatc ttctaaaatg attgttgact tgttgattag    7560
cccccatgca attcccctct cccgtccctc agcacgtaag aatggcccct tgcttactt    7620
ccacagatcc ttaaatctac cagttagaag ctaatagcct acctctctac caggaaggaa    7680
ctgtgggctg aacataata catgttgact tataatttct tagaaaattg tgtgagaaac    7740
atcaaactcc tgattccagg atatgccaaa gacacatcat taaaaagcaa aacaaaacaa    7800
aacaaacctc atttgacgtt gctagtagtg gcatatttca tcaagatcag ctcaaataaa    7860
tagaagtgag attttcacac aaattagact gtagtgcttt ttttttttaac ttatctttac    7920
catatgattt ttaacggtaa aaaaaatcgt ttgagatatt agatgtataa tatttatcat    7980
ccaattactt cattagttca atctttttc aatggcgctc ctgcatctga gaataaggtc    8040
agaaaatttc atgttctgat ttcatgctga ttttcagaag aaaaatgtta gttttgtata    8100
gaataaccca tcctaagaaa tacatttctt attatatttc ttatcttata tttcttagga    8160
caatgagcta ttcaaagggt gatgataacc agcaccatca gtcagcatta tctaagaata    8220
agaatctgtg tttctacata cagacctcct aaaaaggaac ctacacttaa caggattccc    8280
caggcaattt ggatgcacat taaagcttga gcaacactgc attagaaagt tagttttcca    8340
tcacaaaaac agtaacaaaa ggaatataaa gtaagttact ttaataatat aagaagaggg    8400
gcaggccggg cgcagtggct cacgcctgta atcccagcac tttgggaggc tgaggcgggt    8460
ggatcacctg aggtc                                                    8475
```

<210> SEQ ID NO 4
<211> LENGTH: 8401
<212> TYPE: DNA
<213> ORGANISM: Homo sapiens

<400> SEQUENCE: 4

```
tttcatctaa gactacattt ctattgtttt atataatcag cccccctaag atcaacatgt      60
ccacattttt tggcaaagac aaagcctact gatttcagga tcattatttt ccttttttcaa    120
aagcacaaac ccaaactgag aaataaatca agagaaattc tccttttttc tatgctaatt    180
tagaagtaga gtctttatt cttttcaaac ccaaagagaa tcagacatac aatatgaatt     240
tatctacttt cgcttgctca gactgagagg aaagattaat attttcaggc tgttagtcaa    300
aactgttcat tcaaatatta tttaataaaa tccaagaacc agctaaaaag tcgcttaagc    360
taagaaacct tcaccagcct catgggaaat tgtgtacagt tttccactag aatagcctat    420
aaatgcttac tgaaaatgtc taagttcata tcttggtaac taacatttta attcaatctg    480
cagaataata tatgcttctt tagtgctaag atatgaatat tagaggcatt ctttcttaaa    540
atttctattt agttatactt tcacaaataa ctatataata ttaaaattct gcatgtggca    600
taaaacatat tttaatggag aaggtaatgt gtagggagtt tatttctgtt tgctattaga    660
acttgtgttt attcttggtt aaaaaaactg cagattacaa catagaaaaa aacaaaagta    720
tgttgtatat ctcttacagt agaagataaa gagtagttct aaatttagaa aggaaaaata    780
aatatacaca gtgaaaatat gtgtcagtga gatgttaatc aaagatcaac tattgctgag    840
accagcaata ttaaatccct gcacaattac tcatattata atgagaattt taaaagaaa     900
atatgaacac ataacataat gaaggcagaa gtcactctca tccttcatct ttgtattccc    960
aattcaggaa gctggtatag tatcttcatt ataattacta ttcaacaaac atttgtaaaa   1020
tgaatgaata aggaatgaat gatgagaaaa atgataaaca tctccctctg tctcctggga   1080
gttaactgca ctactttctt ttaaatttaa ttaatcctca atgtccttgt aaaatagcca   1140
aagggaaaat gtatttacat tactctaaat attgatgcaa tctacaaaaa gtgttaaaca   1200
acttcctcaa agtaaataaa atgttcacaa tccagctagg ataaaaggat ttaaatcatt   1260
tcctaggtag agggctttca attagagccc ctgctgcatt aaccatggga actcatctca   1320
ctctcttcat gatggagccc tgagtgttgc tgctaatctg tactctacca ttctaatgct   1380
tttaaggttc cttttcagcc cttcctcctc gtaatccaca aatactgaga ccaaggcatt   1440
ttttgggtca gtcctaattt caagcattct atcctgccct ccccaaatga actcacactt   1500
attagaccat atgttcctat attagttcag gaaggggggaa aaaatgttaa tcacacttgt   1560
atataagaga tcatagaaaa acagtttact aacctgtgaa aataccattc attctctgtt   1620
tacctctggt ccacagctaa gcaatcagca ggatataaat gtaccctatg ttcactattc   1680
agtattcata agtatactac ttatgaattg gaaatctgac acaacattta catgacctaa   1740
tttttgaaaat ttaaaatagt gtaaggcccc taggcttaat tttacagggg aaagattaaa   1800
gggacacaag caaacatata ttctctctct gtgctgtggg acactggtaa ttttttgact   1860
taaaatattt gatacttaaa atgccaaact tctacatttc tgcagtaaca aggcagttat   1920
catattgaat accatttctt tctctccagt aagtagagtt aatattagca catgaactga   1980
aaatattaag tgattataaa aacgtccaaa taaattcatt aaaatttagc ttggcaaaat   2040
gttagtttca tgttcttggt agaagtcctt ttatatttat attcaaatga atgaacaat    2100
ttacaagcaa aggaaatggc atcaaatatt tcacaccctg cctcccaagg tgtattgatt   2160
```

```
catgcttttt gctcagatct aggtttctcc actcaggaaa agaggagaat gtacccatac    2220
ttgggaaaac aagtttccga tggcacagct ttgatcaaac agcaaaattc tatccatcta    2280
tgtattgcca tctgacagta tgacaaatgg tcccatgtgc gatattcaca ctgcattgca    2340
gtcaaacctg taagtcaaag gatatgaaat aatagtaact atacattaag cacagaagaa    2400
aatgaaacaa acaaaaaggt tttaaaccaa ccaaaaatat gtcttatttt ggatgttcta    2460
tatgttctta cattctctca ggtcttttgt gtcattatga acacaattct aacaagcttg    2520
attattttat ttccattcac atattacagg caacaagctg aaaaagtaga acggggtgta    2580
gagagacagg acaaagtaca gattagggct tgaagtgccc ctgaccagtc gacagcaacc    2640
acatggaata atgactcatg tgcattaatg atcacactaa atgatatttg tttttttacc    2700
tagtccttca actgacagct taaagaactt caggttgttc tgattcttga gcctcctcta    2760
cagcttcaga gaggactttc attttatttt ggatcaaatg ctccacaact agttgaaact    2820
ggaattaaat tttatatgaa gttcctagat gatttaaagc tgtaagaaga agaataatga    2880
atcataagaa aacttgctgc tacagatatc aaaaaggaat gttaccatcc ctcatgctaa    2940 tcctttcat tttaaataaa caggatctaa aaaaaataat gctgggaagt cctaaccaca    3000
tcaagaatgc ctcagatcag tgacccaggg aaccttccag aatggatgaa atagacccaa    3060
agctgaattc acctaatttt agggccaaaa acccaaaaaa caaaacaaga ccaaaaaaat    3120
cttcagatac tgggagaaca aatctcaatt gctcaattgt atcttatgaa acaattttt    3180 caaaataaaa caagagatat ttaagattca ttaagttctt gtcatttcaa attttaagaa    3240
aaatattttc taatggaatt acatatattt atatgattct tctagttata tccatggtaa    3300
taaatactct tttcagttgg aaataaaacc catttgtgct atattattag ggaaaatatc    3360
tacataaatt agttttttaat ttaactaaag tctatctttt gaattcataa gcataaaatt    3420
ttaaccactt gcaaaattta taacacactt aaggtagtca gatgccttgt caagtagttt    3480
aacaaaagtg attttcacct gtttgtttta ataacagtgc atcgatttta tgaaaatcag    3540
gcatgccctc gggtcctaac aaagtatacg aagctgaatg gatctatgcc aaatatgcca    3600
gattttactt tctgagtctg attttatact tctgtcctct ttcttaccac atggcttcca    3660
gtatcactta cagactaacc cttcaaaagg agaaggctaa gttactaaca tttggaaggc    3720
ttatgaaagt gaagcatagt tatgagccag caatgttttt atttagggaa tgtgtgcaaa    3780
ccatacactt aagcaagctc tggggaatga gagttggggg gaatcaactc ttttatttgc    3840
taattggtat ttcctttaaa agatagagtt cttccagatt ttaactgtgt taatagttac    3900
tctagaaaaa ttggagattt gtgtgcatat atttatgtt gtaaacagac acatacccag    3960
agacactgag agagacagac agacagtaaa cagaggagca ctaaccacaa acggtttaca    4020
aatgacctct gtgctcattc acctgtctgt tccccacctt gcctttata gcaactatag    4080 caacagccat gagagtcatt gtggaaagaa ataaaataaa attaaaaaat cctggaagct    4140
tgtaaagaat gtgagcaaag gggaggaagt tgtgaaaaaa atgaataaag ggcaccgatc    4200
cagagtattg aagaaggcag agtggagagc ctagtaatga gtatctggta ccccagtatc    4260
ctctcccaca gaatcgtac agctctccgt ttatgacagt ttaaacttaa tttaaattat    4320
caaacagaca ctttcctcaa acatataaat gatgaggcag ttcattcagg ctgtatgtat    4380
aaagttgttc cagccacctt tttctaatgg cttctctata tcttttacat ggagacaatg    4440
agagatttgc ttaggacaat ttgactgtaa tttagaagta ggaaatggga agtatttgta    4500
tcttctttgc ctaactcaca ttagttactc aagtaagcat ttcttccgtt attgcatttt    4560
```

```
cctgattaca agttttatgt tttctctaaa acacatatca aaagaaatgt cctaagcact      4620
atgcaggggg aagccatgac atttatccac cactgtcagc aaaaacatga acttagccct      4680
caacagaata tttcacttca ttctagtgtc acctctgcgt cacctgcact ggagtcacca      4740
cttgcctgtt gggtaagacc aggatgcacc gctgaaataa aaaggggtca gacaatacaa      4800
gaaaagccag tagaaattgc caaatgtatc agaatacaca caggctttct aaggatatgg      4860
cccaagagga aggctctaga gcccaccctg aaacaggatt tttgacttca cagataaatt      4920
atttaatttt caataacaca attcaattaa agaaagggaa atacaaggct aaacaaataa      4980
gaaatgaaga caaaacccca acctttcaaa tctaaagaaa ataatctgtt ttaaagacac      5040
agatgaagat caggaaccca aaacagaaga aaggaaaggc aattaacgct ggcatctgat      5100
aacaacgaaa agtatggagt ctggagaatc gctagactct aaaaattata aaggtttaga      5160
cttggacttt gtacactgaa gaaaagaaaa ctgcatgcat ttatactgac caatgtacac      5220
tattgctgct tttaactttt tgtgtatatg tagggtagat ttttttttaa gtgaaagcaa      5280
gcttattaag aaagtaaaag aataaaaagg tggcttctcc ataggcagaa aactagcgta      5340 gttttttat tagaaattgt tattcaataa tagtacatgt tacaaataaa taccatttta      5400
aactgaaaaa attgtagact ttcaaatcag ttagggtggt caccctaaaa aagggcattt      5460
tttcccctta gtctccttgt tcatgttgct cacaacaaga aatgggctaa tgctatgaat      5520
aataataaca aacactgcct tctgtcaggc cctgtgctga ataccgtctg catatgtata      5580
ggaaagggtt aactcagcag gtcttgtttg cccagactct gtacatttcc aagaaaggtc      5640
tgcctttagg actggtcctt ggccagctcc tggagaatga gctctcagct tttagaaaat      5700
tctatctgct aagaatagtt ttgcatgtct caggtcttgg gccacaaaat atcagtttaa      5760
tcagatggtt tatgttaaca agtatgattt atggcaaaca tagatctcta atctccattt      5820
ctctctcata tatctatatt tatctatcca tatatatgta cctatatata tcaaatatga      5880
agatatgttt atagcaattg catataaata gagagatagt atgtagtagg aagagagaca      5940
tagatattat tcttcatttt agaatgttat cttggtatgt ttaaaaggaa aaacttaaga      6000
tgtgttgcaa ttgcagtatg agtttcaggt atgtacatgt tatgtgtgtg tgtgagagac      6060
acacacaaac acatttcaaa catgttttat gtttaagctc aatattcaaa cacagaaata      6120
taacatctat tcttaatatg ttttatgtaa gtacagcagc agcattatta aatactgtat      6180
ttctatggtg attgaaaatt agtaggcaga gaattttgt aatggttctt ataattttt      6240 gtaatagtaa atgattactt tttgtttagt atagttttat aatctataca tgaataaagt      6300
ggatatttct attcatatag aaatgtgatt tactctcatg tacttatcta catgctaaaa      6360
ccataagtta tcaattttag ttctgtgcca aggcactttt actgaataaa aataatcagc      6420 taatttata ttttcctgat tcaaatttat atgcccgtgt aatgttccgg ggttttttt      6480 tttaatttct gtaaatcaga atattcagat gttgaaaaag tctttgcctt cagatttaaa      6540
agataccttt gaaatgtagc atatcccaaa atgcaaccca gaggctggca atgtcaacat      6600
ttttctgttt taaaaaacct cttatgaaaa ctattgccat actaaatttt ttacttgctg      6660
atgacttaca gctggaaagg attctgtaca tataagacat caaatattga ggatactgga      6720
acttttaaat taatggcaaa gaaagtcaac aaaggaagtt catatgaaat caaactagta      6780
atatgattac aaaaaaaaaa gtttaaaatt tttcttggcc ccagtcttat catttctgag      6840
ccaaatacaa ttctatcgaa atcacctgaa actgaaatca ccattctagg ctggttttcc      6900
```

```
cataaagatg gactgctcca aaaagaggaa tcaagaaaga atttggctca cagtgaatta      6960
ttcactttgt cttagttaag taaaaataaa atctgactgt taactacaga atcatttca      7020 aattctgtgg tgataataaa gtaatgacca cttttcagct ggagggacta acttcttttt      7080 ttttttgct gcatatatag ctgtggtaca ttttaatgtg aaatgatgac tgcatcagct      7140
tatatccatg gagcagattt tagcattcag cttgggtctc ccagtcaata tctacgagtc      7200
tcttcttaag gagatcgatg acacagatac atacagacta caaatgtga taccaataat      7260 caagaattca ctcagttaag attttgccca ctgatttcca cacaagaaac ctagaattta      7320
ctagattctt gtgcctgtga ggctccactc atttccctga atcacaaaag ctacagagta      7380
tttagataga aatataccta ctcttaacat gaaccatttt aaatatatgt attactgtgt      7440
ccacaggagt acactttaaa gcagggactt cactcttcaa tctctccaat cacgtgttac      7500
ctaaagtggc atgtggttcc ctaaagctta ataactgaca ttgccttaaa aagggtttt    7560 gcttcccgac taatgtggaa aaagtctgaa aaatgatttt aaatcttca ctaaattct      7620 catttggtca cgtggaggaa aatgattca ccaaatagat actctcatta attttttaat      7680
gtaatttatc aaagaaatga aatatttaga taaattccag atttccccca ccatgagctt      7740
ctccgaaagt atactccatc acagactgct cactaagaag ctctactgca gtcaaagtga      7800
ccgaatttaa ggggacataa tgactacttc tgctacacag aaacattatc catctctaac      7860
acttccctat gagatggaag acggacttct aatcaggtac cagagagggc tctgccaact      7920
tcagggcttt gatgaataag aatggttgag agcgctcatc ataaatgaat tcagtataac      7980
tgagtgagaa agtgagagaa ccagagaaat aaatcctcat gtagaaaatt taggggtatg      8040
aaatgccaaa tgccagttaa ccaaagcttt ctttgtcata agcaacttc tataaaaatt      8100 gctgaaaata aattcttcat ggctcaatgt gaatcagtaa tttccatctc tattacactg      8160
ttgtttaccc aaaaactatt tttaatgact aagactcaga gtttgccaga gtgttttcca      8220 caaacaact gttttgagat actccagatc tgtaatcaag taagtctgaa aaaccccaaa      8280
tacctcactc acctcttgga tatgcataaa gcacactaat atataacgtt ctaaaaagcc      8340
aatcattaaa accgttttat attgttaag catttcctag acatatttgg ctacaaatct      8400
a                                                                     8401

<210> SEQ ID NO 5
<211> LENGTH: 8427
<212> TYPE: DNA
<213> ORGANISM: Homo sapiens

<400> SEQUENCE: 5
gcacctgcca ccacgcccag ctaattttct attttcagta gagatgaggt tttgccatgt       60
tggccaggct ggtctcgaac tcttgacctc aggtgatcca cccgcctcag cctaccaaag     120
agctgggatt acaggcgtga gccaccgcgc ctggccatat taacaaattt taaatcacaa     180
ctatgtgggg ggggaggcta gtattattac agcagattgg tttgctatat aaacaagtac     240
tttaaaaaat atttcttggg ccaggcgtgg tggctcacgc ctgtaatccc agcactttgg     300
gaggccgagg tgggcagatc acttgaggcc aagagttaag agaccagcct ggccaacatg     360
gtgaaacccc atctctacta aaaatataac aattagccag gcatggaggt gcatgcctgt     420
aattccagct gctcgagagg ctgaggcatg agaactgctg gatcctggga ggcagaggtt     480
gcagtgagct gatattgcgc cactgcactc catatccagc ctgggcaaca tggcaagact     540
ccgtctcaaa taaataaata aataaataaa taaaactaaa ggcagagttt tcttaaataa     600
```

```
acatggtagc cctcagcaac aatattgtaa gaactcctcg caagagaaaa agctggaata    660
agatactggc taagcaagta agaaaggcac tgccctgctt ctgcatacat tcaaactaag    720
acatatacat tgcagcttac acttacattt tccaatatcc ccaggcatcc ctttcccttc    780
tcaaacagcc aaaaggaacc agccatgcaa ataaaaatac aagttcaaga gcctaaaaga    840
agtcagtgtc ctaaaagaga aaattaatgt aaagaattaa gattttttga aactacactt    900
tctttctggg gctgtttact ggcctccaat acatcaatcc tgtaacactg tgaactacag    960
tgatagattg gtacatgctt ctaaacacaa cagaattttt ccaaggttac atacactgta   1020
acaaaagggg cattttgcag catcttattt tccttaatca actagtttgg atattctaac   1080
agtgcaaaca ttgtaaacaa taaattttca ttaccttttg aactttctga agtcaaccaa   1140
aggcttgtgg tatggatgca atgagtacta gacaggcaga gctgaatact agtcaaaata   1200
ttcagttact ggtgtgatag tccttttggg ggcatacatc acttagggag aaactgaggt   1260
gcaaggacat tttacacaca gcaaaaacat tctcaggaat ttgtcacatc attaccataa   1320
gccaaaaatc tcaaggtctt agaacagcct gagcttctga tcaaattata ttgtaaaaag   1380
agaggaaaaa aatgtgaagc gtgctatttt ttaaaataac agtaactact actactgctg   1440
ctgctgctaa ttctaaacgt ttactgagcc cttattatgt gccaagcacc gtgctaggta   1500
cggtcataga ttttaacaat taatccctgt aacaaccctc tgatattagt taataaaatt   1560
aaagtagaat cctcaccaaa aaaatttaaa cttttccaaat aaaaatataa ataaattatt   1620
aaagacattt cacctctttc tctgcctcag actacatttt caagtattaa atttacacta   1680
aaaccacatt tattttcagg aattccagtt aaagcgtaca gatattcaag atgttgacaa   1740
ttattacaga agaatcacag aactctgaaa ttaaatactg gcacagaaaa ccttccatcc   1800
aaccttacgg aacaactatc cccatttttaa aaaaaaagga acagcatata tatcaggctt   1860
gataataaga ggcttctcat gcccacacta gcaatgaatg atgccataat tataaagaga   1920
cctgtatcgc cacatgcata aaaataattt acatctgcta agtcaagttt tcaatatatt   1980
attttgtgtg taaaccttat agtagctgat aaaaaatata ataaactaat ctaaggtaaa   2040
ctaaaacact aggttgtttc tgaagactca ctttagaatt tgagcagcat aataatcata   2100
atattagtaa tcaaactact tagcagaaag ttcttagagg gctgggaagc tgtgtataat   2160
aaaatggagc agacaagaag gaagggtttt ccgtactgtt taaatcaact acaggtccca   2220
gcatgcagtg ctctaatctg aagttaagca aaaactgcaa tgcatactgg gacttgtagt   2280
aagtaaacca cgttatcaca gcaagtttca agaaagtctg aactatctag cacaatttga   2340
ctatatctta ttatcagagt ctaatcaaat ttaaatcaaa tttgtatgtt ctctgatgtg   2400
gcacacagtt tctctagcac ataccggaaa aagtatcaat atttagacca acattttcac   2460
attagaaaaa tcttacgtag gagaagcaca gaaaaaaatg ctgaaaaagc aaaaaaactt   2520
gatgaataaa aaatataatt tttgaaatag ttttttaaag tttgaatgga tccatttcaa   2580
cattctctaa tcctccccca caaaaagttt aattgttttg gccgggcgcg gtggctcacg   2640
cctgtaatcc caacacttta ggaggctgag gcgggtgaat tacgagatca agagatcgag   2700
accatcctgg ccaacatggt gaaaccatct ctactaaaaa tacaaaaatt agttgggcgt   2760
ggtggcgcac gcctgtagtc ccagctactc aggaggctga gacaggagaa ttgcttgaac   2820
ctgggaggtg gaggctgcag tgagctaata tcgcaccact gcactccagc ctgggacaag   2880
tgtgagattc attctcaaaa aaaaaaaaaa aaaagtttta attgttttaa caggttgctt   2940
```

```
tttaacaatt attcaagatg tattttataa ataattttc ttgaagaaaa ttctcagaag    3000
caaacattcc ccatattcta atattgccca ccaggaaata attttttag taatacgcac    3060 acaccccatc acaaaaacaa acaaaaaaca ctgaagttct gcttttgtca agtccttact   3120
caatatttat gccctccatt cctcacctct aattccctac acacacacac acacgcac     3180 acatccccac acacacgc ttctacaaag aacacttaga aaacagtat tccaactaca      3240 agcccacttc tctcatccac tgacctcttc tgaaaacaca aaagatttt taagctatca    3300 gtaacacgtc caaacacaag ctgataagtt tgagctagaa tttacatata tacagttgct   3360
acacaccctc ctattttctg caagtctgtg gaaggaggct gggaaagaac taagtgcaat   3420
ctgcatcagg aggcctaaca caggtggtgg gttattttca ggcaacagca ccttcacaaa   3480
catgttttgg aatatagtcc aagaaattcc taacaaggaa agataagctg gcacacaaat   3540
ttaacgcaat ccagctaaaa atcatctgca acacatgcta ctacatttca ccataaaagt   3600
gacgggctac tataaaggat ttgaagcttc gtcaatacaa catactgtcc ataaggccag   3660
agatagcagt tgccatggtt actatacca ctttttatcag gaaattactg tcattacccc   3720
aaagttttgg gtacttattt aaaatttaaa aaaaacacac acaatttagg gttctgactg   3780
ttaattgagt gaaataatca actactgttt gatttgtaag tatgtcgctt ggagatgca    3840 catggttaac aatacttgga tctgcagcag aaaaaaaatc aattccttc tgctgctcct    3900 tctcctcaag tactgacagt ttgtattctc aatgcagcca aaacaataaa acaaaaccca   3960 tcttttggc ttctgtgttt aagttatttt tccctaggc ccacaaacag agtcaaaata     4020
aagcctagat catcaacctg ttaggcctca tccccttcct atcccctcca tactggttca   4080
ctttcttgac tacttagaaa aggcagaaaa catttctgta actgattcca agtatagaa    4140 aagaatagtt gccttcaact gagatatttt caccaaagtc ttttttattt acttttttt    4200 taaggcaggg agaggggaga gacttgcagg gtactgaaag ggagaagtgg aggagtattc   4260
aaattgccac acaagtctag tgtaagaaag ttgctttaga agagtccaaa ggatggctga   4320
acctcacata taatttctaa aagctttgga agagttcacc ataatttaa gactgaattg    4380 agggacaagt aatagaaaag ttattcataa agtctacttc aacattttta caaaagataa   4440
ctattcaaaa atttaacaca catataagaa ttatacgaaa gcctacaaaa tagtatggcc   4500
acatatacac acaaacatac aaagtagaaa acataagcta tttaagaaat aattatctac   4560
aataaattca atgcaatgtt aacatattat ctctttttta aaaaatcgca aagcagcaaa   4620
aacatacacc tgagaaaatt aatgtgatca aaacgttaaa gaattcttag gcctataaaa   4680
aaagcccatg tacaaaagct cctgagaagt caacataaat cattaatatt tcccagcaca   4740
aaataatatg aaaattcaaa catgtttcaa gaaatcagtt ctagatatag atataaaaga   4800
attccattaa aggtcagaga cctaaaactt taattccttc ccttctctgt ttgaatagta   4860
attaaataca aaagccttca gcaataaaat actaaggata caaaatttaa aagcacatta   4920
atataagctt aacttcagta tgtcttcaca gaaagctta ctattcactg tctgtaggat    4980 gaaaagtta ataacaccct gagaggtttc attttatct aaacagttaa gtgttttct      5040 caccgttcac agaagcaagt ttctatattt actttctaaa gggggcaatt tcaaaagaat   5100
agtcacttct aaaatttaag atactatacc ttttgatagg ctcataaaca cagggttcct   5160
aattatctat attttacttt aaaatgtttc tattccaaat ttgtgagcag agtttataag   5220
aaagctgaaa ctcaaggctt taaactttg ggttatttt acacaaaaat atttcagtgc     5280
actcctctag atttgagtag tcatttcctt gtgcatcctt ctaaaataga aaacaaaaa    5340
```

```
tgatatatcc atatatacct aatactaaca catacagata tacatctttt tcactgtgaa    5400
acaagcttga aagctttagg cagtaagaat ttttcagaaa gttagcagag tcagtcaaaa    5460
cattcaaaac ttgaaccatg acatctgtta ctctgtcaat aagagtctat agaagaatca    5520
gggaacttac atactcacta aaatcaacta ctatcacatc acatcaatgg agaaatgaag    5580
aaaaactgta atagggggaca tacaattcac aggatcttca aaagggaaaa tgatctttt     5640 ttttttttta aattatgaga aactgactag gcagcatttt ttcaaaagca gcttcaaaac    5700
tataacaaag acattttggg taaccacagc agtatttaaa aaacaaaaat ttaggccggg    5760
cgtggtggct cacgcctata atcccagcac tttgggaggc caaggcaggt ggatcacctg    5820
agtcaggagt tcaagaccag cctgaccaac atggtgatac cccgtctcta ctcaaaatac    5880
aaaacttagc cgggcgtagt ggcggacacc tctataatca cagctactca ggaggctgag    5940
aggcaggaga atcgcttgaa cctgggaggc agaggttgca gtgagccgag atcacgccgt    6000
tgcactccag cctgggaaac agagcgagac tccgtctcaa aaataaaaa aataaaaaaa     6060 ctatagtgtc cagggtgcac tttaaatgta ttactttctc aactgatatg gaaaagtta     6120 gcatttaaag acagaagctt ctgtccatgt attaattagt tacctatctc aacaacttaa    6180
tatctgcatg ctttcttacc atttatgaag aacttttata tgtattatct catttggtct    6240
tactgagaaa acagtatttt gcctacaaaa tagacaaaat tcaaagcaga tttatcaaac    6300
tttctagcat ccccaaattt ttaaaacttc gacacaaaac tttacaagca accacagtgg    6360
catgatattt tcagtgataa tcaattcacc taacactaac agagtttcaa aggaccatgt    6420
gctataaatg ctatgaaact gttaaagtag ctatattcat ctttatgcag ttactgttac    6480
atcaacaatg acctaccact gatcaacttg acttacagt tcaagaatct cagtctttgc     6540
aggctaactt aagtacatca accatatgta tttataaagc cgagtgccta aaaattgatc    6600
tatattagaa tcatagtctg taaatccgag ggaaaaaac tacaagaagt ctaaaatttt     6660
ttcaacacac tatacccctt tccaaaatct caactactct atatcctatt tgtattaata    6720
ttatagggat gataacaagg cttaaagccc taaatcatac caactacttt tgtttataac    6780
aattacaaat aattttttaa aatacatgct caacatccca ctcatcaaca caagactaat    6840
tccccttcca aataaaataa ttctaaacag tgctctgtac caagggccag aatccttata    6900
ctatccgcaa tcgcacatct actttgtaca gtcaaagact tcactttcaa gtagcaaaca    6960
ttatttatga atggaatttt taaatggact tactcaaaat cttctggaa ctttaaggtg      7020 ttaatcctgt tgcttagctg aagctaagca gagctgtaat aagtagcaag accctcaaaa    7080
ttcaaaaatt tcctttatct tgctgtagca cctcctgctg gatagcattt agagatcttc    7140
atgtaagcag aagaagagta tttcagaggc agctccttcc agaagactga ataggaaaaa    7200
ggatggaccc ttcaaagcta aagaaatag gccccatcca tcacttatac cttctaaaaa     7260
tacaatttag cccaggtagg tgtcttttc atctattact actccagttc cacaaagact      7320
tgcctcagtc caaaatacaa catgcttaaa taaagcctgc aaaattgtct aaaaactaag    7380
ttaaaaagca ttcaatagca cccaagcaaa acactttatt atgggcagcc aagcaatgtc    7440
agtcaaactg taaatactat tatgttacca aaagcaaaag tctgatgtta aaaaaaaaa     7500 aaaaaagcc cctggaatat tcgtaacatg ttagccagat gtttgtgttt tgagaacttt      7560
gtgcactatt actatgctct tcacttaagg atagttgtac atctacaaac gttttaagta    7620
cagaaatttt tttataaaca ttagcataac tgtacacaaa atttcctctt tgccatgaaa    7680
```

```
agataggtcc tgggatttga aaatgtattt ttcagacatt tttaatgacc ccctaaaata   7740
aactagtttt aagcccacaa caccgattcc ataaacaagt aaagacagaa gaagagaata   7800
agaaggaact taccaaaatt aaaatgaata atagtatttc cagtaaaaat gtagtaacag   7860
tttccaacaa tgctgtaaac caaataaatt gtgaaactta aaaaaggaag gaggggggcca  7920 gtcttcaaag accaaaagca aagctgacct atttatttct attgcttaga gtgaacacca   7980
gatgtaaaca aatatcataa acactgaaaa gtacgcttac atggtttagc ctcaatttca   8040
gtacccttac caggccctca ataaagctac agatgttggt gagaactcgc tcaaaaagga   8100
gataattcca gcccctcgcc ttaaagaatc cctatcaagt gaacctgtga aaagacttcc   8160
ttcccagagt gcacaactgc tttaaaaaaa aaaaactttc atcagcccaa attaatctga   8220
ttctaatatt caactatcca ttatttatat ataaatgttc ttccctctct aactttccca   8280
gctcgagcat ctacattcct gacaccgact attagcaaaa atgcacaact ccttccccag   8340
ctatggggca aatctttgaa atctgaaaca cagccacaaa gttcactgtc aaggccaggt   8400
gatgaggccc acacatgccc ggaccctt                                      8427

<210> SEQ ID NO 6
<211> LENGTH: 1704
<212> TYPE: DNA
<213> ORGANISM: Artificial Sequence
<220> FEATURE:
<223> OTHER INFORMATION: Synthetic

<400> SEQUENCE: 6
ggtaccaccc aagctggcta ggtaagcttg ctagcgccac catggtgctg cagacccagg     60
tgttcatctc cctgctgctg tggatctccg gcgcatatgg cgatatcgtg atgattaaac    120
gtacggtggc cgcccctcc gtgttcatct tcccccctc cgacgagcag ctgaagtccg      180
gcaccgcctc cgtggtgtgc ctgctgaata acttctaccc cagagaggcc aaggtgcagt    240
ggaaggtgga caacgccctg cagtccggga actcccagga gagcgtgacc gagcaggaca    300
gcaaggacag cacctacagc ctgagcagca ccctgaccct gagcaaagcc gactacgaga    360
agcacaaggt gtacgcctgc gaggtgaccc accaggcct gagctccccc gtcaccaaga    420
gcttcaacag gggggagtgt taggggcccg tttaaacggg tggcatccct gtgacccctc    480
cccagtgcct ctcctggccc tggaagttgc cactccagtg cccaccagcc ttgtcctaat    540
aaaattaagt tgcatcattt tgtctgacta ggtgtccttc tataatatta tggggtggag    600 ggggtggta tggagcaagg gcaagttgg aagacaacc tgtagggcct gcggggtcta       660
ttgggaacca agctggagtg cagtggcaca atcttggctc actgcaatct ccgcctcctg    720
ggttcaagcg attctcctgc ctcagcctcc cgagttgttg ggattccagg catgcatgac    780
caggctcacc taattttgt tttttggta gagacggggt ttcaccatat tggccaggct      840
ggtctccaac tcctaatctc aggtgatcta cccaccttgg cctcccaaat tgctgggatt    900
acaggcgtga accactgctc cacgcgccct gtagcggcgc attaagcgcg gcgggtgtgg    960
tggttacgcg cagcgtgacc gctacacttg ccagcgccct agcgcccgct cctttcgctt   1020
tcttcccttc ctttctcgcc acgttcgccg gctttcccg tcaagctcta aatcgggggc    1080
tccctttagg gttccgattt agtgctttac ggcacctcga ccccaaaaaa cttgattagg   1140
gtgatggttc acgtagtggg ccatcgccct gatagacggt ttttcgccct ttgacgttgg   1200
agtccacgtt ctttaatagt ggactcttgt tccaaactgg aacaacactc aaccctatct   1260
cggtctattc ttttgattta agggatttt gccgatttc ggcctattgg ttaaaaaatg     1320
```

```
agctgattta acaaaaattt aacgcgaatt aattctgtgg aatgtgtgtc agttagggtg    1380
tggaaagtcc ccaggctccc cagcaggcag aagtatgcaa agcatgcatc tcaattagtc    1440
agcaaccagg tgtggaaagt ccccaggctc ccagcaggc agaagtatgc aaagcatgca    1500
tctcaattag tcagcaacca tagtcccgcc cctaactccg cccatcccgc cctaactcc    1560 gcccagttcc gcccattctc cgccccatgg ctgactaatt ttttttattt atgcagaggc    1620
cgaggccgcc tctgcctctg agctattcca gaagtagtga ggaggctttt ttggaggcct    1680
aggcttttgc aaaaagctcc cggg                                            1704

<210> SEQ ID NO 7
<211> LENGTH: 1120
<212> TYPE: DNA
<213> ORGANISM: Artificial Sequence
<220> FEATURE:
<223> OTHER INFORMATION: Synthetic

<400> SEQUENCE: 7
tgctagcgcc accatgaaac acctgtggtt cttcctcctg ctggtggcag ctcccagatg      60
ggtgctgagc caggtgcaat gtgcaggcg gttagctcag cctccaccaa gggcccaagc     120
gtcttccccc tggcaccctc ctccaagagc acctctggcg gcacagccgc cctgggctgc     180
ctggtcaagg actacttccc cgaacccgtg accgtgagct ggaactcagg cgccctgacc     240
agcggcgtgc acaccttccc cgctgtcctg cagtcctcag gactctactc cctcagcagc     300
gtggtgaccg tgccctccag cagcttgggc acccagacct acatctgcaa cgtgaatcac     360
aagcccagca caccaaggt ggacaagaga gttgagccca atcttgtga caaaactcac      420 acatgcccac cctgcccagc acctgaactc ctggggggac cctcagtctt cctcttcccc     480
ccaaaaccca aggacaccct catgatctcc cggacccctg aggtcacatg cgtggtggtg     540
gacgtgagcc acgaagaccc tgaggtcaag ttcaactggt acgtggacgg cgtggaggtg     600
cataatgcca agacaaagcc ccgggaggag cagtacaaca gcacgtaccg ggtggtcagc     660
gtcctcaccg tcctgcacca ggactggctg aatggcaagg agtacaagtg caaggtctcc     720
aacaaagccc tcccagcccc catcgagaaa accatctcca agccaaagg ccagccccgg      780 gaaccacagg tgtacaccct gcccccatcc cgggaggaga tgaccaagaa ccaggtcagc     840
ctgacctgcc tggtcaaagg cttctatccc agcgacatcg ccgtggagtg ggagagcaat     900
ggccagcccg agaacaacta caagaccacc cctcccgtgc tggactccga cggctccttc     960
ttcctctaca gcaagctcac cgtggacaag agcaggtggc agcagggcaa cgtcttctca    1020
tgctccgtga tgcatgaggc tctgcacaac cactacaccc agaagagcct ctccctgtct    1080
cccggcaaat gagatatcgg gccgtttaa acgggtggca                            1120

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
tactagcggt tttacgggcg                                                   20

<210> SEQ ID NO 9
<211> LENGTH: 24
<212> TYPE: DNA
```

```
<213> ORGANISM: Artificial Sequence
<220> FEATURE:
<223> OTHER INFORMATION: Synthetic

<400> SEQUENCE: 9
tcgaacagga ggagcagaga gcga                                              24

<210> SEQ ID NO 10
<211> LENGTH: 37
<212> TYPE: DNA
<213> ORGANISM: Artificial Sequence
<220> FEATURE:
<223> OTHER INFORMATION: Synthetic

<400> SEQUENCE: 10
aaagctagca tgctgctgct gctgctgctg ctgggcc                                37

<210> SEQ ID NO 11
<211> LENGTH: 36
<212> TYPE: DNA
<213> ORGANISM: Artificial Sequence
<220> FEATURE:
<223> OTHER INFORMATION: Synthetic

<400> SEQUENCE: 11
aaaagatctt catgtctgct cgaagcggcc ggccgc                                 36

<210> SEQ ID NO 12
<211> LENGTH: 78
<212> TYPE: DNA
<213> ORGANISM: Artificial Sequence
<220> FEATURE:
<223> OTHER INFORMATION: Synthetic

<400> SEQUENCE: 12
ggaaattgag aagtatcatt cacaacagta ccacaaacat gaaataaatg tggatcctat       60
taatagtaat caattacg                                                     78

<210> SEQ ID NO 13
<211> LENGTH: 78
<212> TYPE: DNA
<213> ORGANISM: Artificial Sequence
<220> FEATURE:
<223> OTHER INFORMATION: Synthetic

<400> SEQUENCE: 13
ctcattctgt gggttgtcat ttcacttcct tgatgctatc ctttcaagca aaatcctagt       60
caataatcaa tgtcaacg                                                     78

<210> SEQ ID NO 14
<211> LENGTH: 77
<212> TYPE: DNA
<213> ORGANISM: Artificial Sequence
<220> FEATURE:
<223> OTHER INFORMATION: Synthetic

<400> SEQUENCE: 14
cttattttct aagtagtata gacttaattg tgagaacaaa ataaaaactt ggatcctatt       60
aatagtaatc aattacg                                                      77

<210> SEQ ID NO 15
<211> LENGTH: 74
<212> TYPE: DNA
<213> ORGANISM: Artificial Sequence
```

<220> FEATURE:
<223> OTHER INFORMATION: Synthetic

<400> SEQUENCE: 15
ctcttcccat tctcatttga atctacttca aaaggtttac catactaaga cctagtcaat    60
aatcaatgtc aacg    74

<210> SEQ ID NO 16
<211> LENGTH: 79
<212> TYPE: DNA
<213> ORGANISM: Artificial Sequence
<220> FEATURE:
<223> OTHER INFORMATION: Synthetic

<400> SEQUENCE: 16
cgcctgtaat cccagcactt tgggaggctg aggcgggtgg atcacctgag gtcgatccta    60
ttaatagtaa tcaattacg    79

<210> SEQ ID NO 17
<211> LENGTH: 77
<212> TYPE: DNA
<213> ORGANISM: Artificial Sequence
<220> FEATURE:
<223> OTHER INFORMATION: Synthetic

<400> SEQUENCE: 17
catacagaag ccagtttgaa ctgagacctc actccatttc ttacaagtta tgccctagtc    60
aataatcaat gtcaacg    77

<210> SEQ ID NO 18
<211> LENGTH: 78
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t

<400> SEQUENCE: 18
naccgtttta tattgtttaa gcatttccta gacatatttg gctacaaatc tagatcctat    60
taatagtaat caattacg    78

<210> SEQ ID NO 19
<211> LENGTH: 77
<212> TYPE: DNA
<213> ORGANISM: Artificial Sequence
<220> FEATURE:
<223> OTHER INFORMATION: Synthetic

<400> SEQUENCE: 19
gatcttaggg gggctgatta tataaaacaa tagaaatgta gtcttagatg aaacctagtc    60
aataatcaat gtcaacg    77

<210> SEQ ID NO 20
<211> LENGTH: 79
<212> TYPE: DNA
<213> ORGANISM: Artificial Sequence
<220> FEATURE:
<223> OTHER INFORMATION: Synthetic

<400> SEQUENCE: 20
cacaaagttc actgtcaagg ccaggtgatg aggcccacac atgcccggac cttgatccta    60
ttaatagtaa tcaattacg    79

<210> SEQ ID NO 21
<211> LENGTH: 78
<212> TYPE: DNA
<213> ORGANISM: Artificial Sequence
<220> FEATURE:
<223> OTHER INFORMATION: Synthetic

<400> SEQUENCE: 21
caaaacctca tctctactga aaatagaaaa ttagctgggc gtggtggcag gtgccctagt    60
caataatcaa tgtcaacg    78

<210> SEQ ID NO 22
<211> LENGTH: 38
<212> TYPE: DNA
<213> ORGANISM: Artificial Sequence
<220> FEATURE:
<223> OTHER INFORMATION: Synthetic

<400> SEQUENCE: 22
aaaactagtc agagaggaat ctttgcagct aatggacc    38

<210> SEQ ID NO 23
<211> LENGTH: 35
<212> TYPE: DNA
<213> ORGANISM: Artificial Sequence
<220> FEATURE:
<223> OTHER INFORMATION: Synthetic

<400> SEQUENCE: 23
aaagatatcc ctagccagct tgggtggtac caagc    35

<210> SEQ ID NO 24
<211> LENGTH: 35
<212> TYPE: DNA
<213> ORGANISM: Artificial Sequence
<220> FEATURE:
<223> OTHER INFORMATION: Synthetic

<400> SEQUENCE: 24
aaaactagtc tgtggaatgt gtgtcagtta gggtg    35

<210> SEQ ID NO 25
<211> LENGTH: 34
<212> TYPE: DNA
<213> ORGANISM: Artificial Sequence
<220> FEATURE:
<223> OTHER INFORMATION: Synthetic

<400> SEQUENCE: 25
aaagatatca gcttttgca aaagcctagg cctc    34

<210> SEQ ID NO 26
<211> LENGTH: 77
<212> TYPE: DNA
<213> ORGANISM: Artificial Sequence
<220> FEATURE:
<223> OTHER INFORMATION: Synthetic

<400> SEQUENCE: 26
ggaaattgag aagtatcatt cacaacagta ccacaaacat gaaataaatg tgctagtcag    60
agaggaatct ttgcagc    77

<210> SEQ ID NO 27
<211> LENGTH: 79
<212> TYPE: DNA
<213> ORGANISM: Artificial Sequence
<220> FEATURE:
<223> OTHER INFORMATION: Synthetic

<400> SEQUENCE: 27
ggaaattgag aagtatcatt cacaacagta ccacaaacat gaaataaatg tgctagtctg     60
tggaatgtgt gtcagttag                                                  79

<210> SEQ ID NO 28
<211> LENGTH: 78
<212> TYPE: DNA
<213> ORGANISM: Artificial Sequence
<220> FEATURE:
<223> OTHER INFORMATION: Synthetic

<400> SEQUENCE: 28
ctcattctgt gggttgtcat ttcacttcct tgatgctatc ctttcaagca aaattttaaa     60
actttatcca tctttgca                                                   78

<210> SEQ ID NO 29
<211> LENGTH: 76
<212> TYPE: DNA
<213> ORGANISM: Artificial Sequence
<220> FEATURE:
<223> OTHER INFORMATION: Synthetic

<400> SEQUENCE: 29
cttattttct aagtagtata gacttaattg tgagaacaaa ataaaaactt gctagtcaga     60
gaggaatctt tgcagc                                                     76

<210> SEQ ID NO 30
<211> LENGTH: 78
<212> TYPE: DNA
<213> ORGANISM: Artificial Sequence
<220> FEATURE:
<223> OTHER INFORMATION: Synthetic

<400> SEQUENCE: 30
cttattttct aagtagtata gacttaattg tgagaacaaa ataaaaactt gctagtctgt     60
ggaatgtgtg tcagttag                                                   78

<210> SEQ ID NO 31
<211> LENGTH: 80
<212> TYPE: DNA
<213> ORGANISM: Artificial Sequence
<220> FEATURE:
<223> OTHER INFORMATION: Synthetic

<400> SEQUENCE: 31
ctcttcccat tctcatttga atctacttca aaaggtttac catactaaga actagtttta     60
aaactttatc catctttgca                                                 80

<210> SEQ ID NO 32
<211> LENGTH: 28
<212> TYPE: DNA
<213> ORGANISM: Artificial Sequence
<220> FEATURE:
<223> OTHER INFORMATION: Synthetic

```
<400> SEQUENCE: 32
ccacgcgccc tgtagcggcg cattaagc                                          28

<210> SEQ ID NO 33
<211> LENGTH: 30
<212> TYPE: DNA
<213> ORGANISM: Artificial Sequence
<220> FEATURE:
<223> OTHER INFORMATION: Synthetic

<400> SEQUENCE: 33
aaacccggga gcttttttgca aaagcctagg                                        30

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
cgcggccgca ctagtgacgt                                                   20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
cactagtgcg gccgcgacgt                                                   20

<210> SEQ ID NO 36
<211> LENGTH: 25
<212> TYPE: DNA
<213> ORGANISM: Artificial Sequence
<220> FEATURE:
<223> OTHER INFORMATION: Synthetic

<400> SEQUENCE: 36
aaacatatgg cgacatccag atgac                                             25

<210> SEQ ID NO 37
<211> LENGTH: 26
<212> TYPE: DNA
<213> ORGANISM: Artificial Sequence
<220> FEATURE:
<223> OTHER INFORMATION: Synthetic

<400> SEQUENCE: 37
aaacgtacgc ttgatctcca ccttgg                                            26

<210> SEQ ID NO 38
<211> LENGTH: 26
<212> TYPE: DNA
<213> ORGANISM: Artificial Sequence
<220> FEATURE:
<223> OTHER INFORMATION: Synthetic

<400> SEQUENCE: 38
aaagctgagc caggtgcagc tgcagg                                            26

<210> SEQ ID NO 39
<211> LENGTH: 28
```

```
<212> TYPE: DNA
<213> ORGANISM: Artificial Sequence
<220> FEATURE:
<223> OTHER INFORMATION: Synthetic

<400> SEQUENCE: 39
aaagctgagc tcacggtcac cagggttc                                        28

<210> SEQ ID NO 40
<211> LENGTH: 44
<212> TYPE: DNA
<213> ORGANISM: Artificial Sequence
<220> FEATURE:
<223> OTHER INFORMATION: Synthetic

<400> SEQUENCE: 40
cttttgcaaa aagcttcgcg ttacataact tacggtaaat ggcc                      44

<210> SEQ ID NO 41
<211> LENGTH: 43
<212> TYPE: DNA
<213> ORGANISM: Artificial Sequence
<220> FEATURE:
<223> OTHER INFORMATION: Synthetic

<400> SEQUENCE: 41
ttcatggtgg cgctagcccg cagatatcga tccgagctcg gta                       43

<210> SEQ ID NO 42
<211> LENGTH: 44
<212> TYPE: DNA
<213> ORGANISM: Artificial Sequence
<220> FEATURE:
<223> OTHER INFORMATION: Synthetic

<400> SEQUENCE: 42
tgacgtcgac aagcttcgcg ttacataact tacggtaaat ggcc                      44

<210> SEQ ID NO 43
<211> LENGTH: 107
<212> TYPE: DNA
<213> ORGANISM: Artificial Sequence
<220> FEATURE:
<223> OTHER INFORMATION: Synthetic

<400> SEQUENCE: 43
ctggatgtcg ccatatgcgc cggagatcca cagcagcagg gagatgaaca cctgggtctg     60
cagcaccatg gtggcgctag cccgcagata tcgatccgag ctcggta                  107

<210> SEQ ID NO 44
<211> LENGTH: 80
<212> TYPE: DNA
<213> ORGANISM: Artificial Sequence
<220> FEATURE:
<223> OTHER INFORMATION: Synthetic

<400> SEQUENCE: 44
ctcttcccat tctcatttga atctacttca aaaggtttac catactaaga ctcgaggcac     60
tagtgacgtc aggtggcact                                                 80

<210> SEQ ID NO 45
<211> LENGTH: 80
<212> TYPE: DNA
<213> ORGANISM: Artificial Sequence
<220> FEATURE:
```

<223> OTHER INFORMATION: Synthetic

<400> SEQUENCE: 45
ctcttcccat tctcatttga atctacttca aaaggtttac catactaaga gcactagtga    60
cgtcaggtgg cacttttcgg                                                80

<210> SEQ ID NO 46
<211> LENGTH: 79
<212> TYPE: DNA
<213> ORGANISM: Artificial Sequence
<220> FEATURE:
<223> OTHER INFORMATION: Synthetic

<400> SEQUENCE: 46
catgcacaga ttagccattt agtacttact aaatcaaact caatttctga agtctagtta    60
ttaatagtaa tcaattacg                                                 79

<210> SEQ ID NO 47
<211> LENGTH: 80
<212> TYPE: DNA
<213> ORGANISM: Artificial Sequence
<220> FEATURE:
<223> OTHER INFORMATION: Synthetic

<400> SEQUENCE: 47
ctcattctgt gggttgtcat ttcacttcct tgatgctatc ctttcaagca aaattcaata    60
atcaatgtca acgcgtatat                                                80

<210> SEQ ID NO 48
<211> LENGTH: 80
<212> TYPE: DNA
<213> ORGANISM: Artificial Sequence
<220> FEATURE:
<223> OTHER INFORMATION: Synthetic

<400> SEQUENCE: 48
acactggtca aagggacagg tcattgttat gctggcaatg caggctgctg aaaactagtt    60
attaatagta atcaattacg                                                80

<210> SEQ ID NO 49
<211> LENGTH: 80
<212> TYPE: DNA
<213> ORGANISM: Artificial Sequence
<220> FEATURE:
<223> OTHER INFORMATION: Synthetic

<400> SEQUENCE: 49
actgtagctt cttatttttt acctgcagtg cattcctgta aaagtagtgt ggagtcaata    60
atcaatgtca acgcgtatat                                                80

<210> SEQ ID NO 50
<211> LENGTH: 80
<212> TYPE: DNA
<213> ORGANISM: Artificial Sequence
<220> FEATURE:
<223> OTHER INFORMATION: Synthetic

<400> SEQUENCE: 50
ctggaaattg agaagtatca ttcacaacag taccacaaac atgaaataaa tgtgctagtt    60
attaatagta atcaattacg                                                80

```
<210> SEQ ID NO 51
<211> LENGTH: 80
<212> TYPE: DNA
<213> ORGANISM: Artificial Sequence
<220> FEATURE:
<223> OTHER INFORMATION: Synthetic

<400> SEQUENCE: 51
ccaagcttgt ccaaccgcgg cctgcaggct gcatgcagcc tgtgaaggct ttgatcaata    60
atcaatgtca acgcgtatat                                                80

<210> SEQ ID NO 52
<211> LENGTH: 80
<212> TYPE: DNA
<213> ORGANISM: Artificial Sequence
<220> FEATURE:
<223> OTHER INFORMATION: Synthetic

<400> SEQUENCE: 52
tcaatcattt atcaatttta tcttcaaagt ccctcacttc agggagatga tatactagtt    60
attaatagta atcaattacg                                                80

<210> SEQ ID NO 53
<211> LENGTH: 80
<212> TYPE: DNA
<213> ORGANISM: Artificial Sequence
<220> FEATURE:
<223> OTHER INFORMATION: Synthetic

<400> SEQUENCE: 53
atatataaaa gttcatgtat atataaaatc atgcaataca cggccttttg tgactcaata    60
atcaatgtca acgcgtatat                                                80

<210> SEQ ID NO 54
<211> LENGTH: 80
<212> TYPE: DNA
<213> ORGANISM: Artificial Sequence
<220> FEATURE:
<223> OTHER INFORMATION: Synthetic

<400> SEQUENCE: 54
cgcataaaag gaaaagcatc cttaaaataa acaccatcaa tggctcctcg gtggctagtt    60
attaatagta atcaattacg                                                80

<210> SEQ ID NO 55
<211> LENGTH: 79
<212> TYPE: DNA
<213> ORGANISM: Artificial Sequence
<220> FEATURE:
<223> OTHER INFORMATION: Synthetic

<400> SEQUENCE: 55
gggaggctac agcttgcctc tctaaccact aaaaggcatg accctcctca aagctagtta    60
ttaatagtaa tcaattacg                                                 79

<210> SEQ ID NO 56
<211> LENGTH: 80
<212> TYPE: DNA
<213> ORGANISM: Artificial Sequence
<220> FEATURE:
<223> OTHER INFORMATION: Synthetic

<400> SEQUENCE: 56
```

```
tctggcttcc ctgggccacg ctggaagaag aattgtcttg cgccacacat aaaactagtt        60
attaatagta atcaattacg                                                    80

<210> SEQ ID NO 57
<211> LENGTH: 80
<212> TYPE: DNA
<213> ORGANISM: Artificial Sequence
<220> FEATURE:
<223> OTHER INFORMATION: Synthetic

<400> SEQUENCE: 57
agctgatttt tacgttaaat gtaacatgta aagaaatata tgtgtgtttt tagatcaata        60
atcaatgtca acgcgtatat                                                    80

<210> SEQ ID NO 58
<211> LENGTH: 80
<212> TYPE: DNA
<213> ORGANISM: Artificial Sequence
<220> FEATURE:
<223> OTHER INFORMATION: Synthetic

<400> SEQUENCE: 58
gtgaagagga ggagatgtca aaattcaaag tcttaaatga tgtagtttta agtactagtt        60
attaatagta atcaattacg                                                    80

<210> SEQ ID NO 59
<211> LENGTH: 80
<212> TYPE: DNA
<213> ORGANISM: Artificial Sequence
<220> FEATURE:
<223> OTHER INFORMATION: Synthetic

<400> SEQUENCE: 59
atgacacttg atattgttgt ttatattgct ggttagtatg tgccttcatt tacctcaata        60
atcaatgtca acgcgtatat                                                    80

<210> SEQ ID NO 60
<211> LENGTH: 80
<212> TYPE: DNA
<213> ORGANISM: Artificial Sequence
<220> FEATURE:
<223> OTHER INFORMATION: Synthetic

<400> SEQUENCE: 60
aaaaacaaaa ctggagtaaa caagatgaat tgttttaata gaggcactgt attactagtt        60
attaatagta atcaattacg                                                    80

<210> SEQ ID NO 61
<211> LENGTH: 80
<212> TYPE: DNA
<213> ORGANISM: Artificial Sequence
<220> FEATURE:
<223> OTHER INFORMATION: Synthetic

<400> SEQUENCE: 61
atacaatgtt ccatgtattc tgtgcctgaa cctatgcagc tgatgtagct gaagtcaata        60
atcaatgtca acgcgtatat                                                    80

<210> SEQ ID NO 62
<211> LENGTH: 80
<212> TYPE: DNA
<213> ORGANISM: Artificial Sequence
```

```
<220> FEATURE:
<223> OTHER INFORMATION: Synthetic

<400> SEQUENCE: 62
gatcttattt tctaagtagt atagacttaa ttgtgagaac aaaataaaaa cttgctagtt    60
attaatagta atcaattacg                                                80

<210> SEQ ID NO 63
<211> LENGTH: 80
<212> TYPE: DNA
<213> ORGANISM: Artificial Sequence
<220> FEATURE:
<223> OTHER INFORMATION: Synthetic

<400> SEQUENCE: 63
tgttgttttc agccactaag tttgaggtga tttgttctgg cagtcctagg aaactcaata    60
atcaatgtca acgcgtatat                                                80

<210> SEQ ID NO 64
<211> LENGTH: 80
<212> TYPE: DNA
<213> ORGANISM: Artificial Sequence
<220> FEATURE:
<223> OTHER INFORMATION: Synthetic

<400> SEQUENCE: 64
agcctacact accctttgca gcctttggta actatccttc tgctgtctac ctcctcaata    60
atcaatgtca acgcgtatat                                                80

<210> SEQ ID NO 65
<211> LENGTH: 80
<212> TYPE: DNA
<213> ORGANISM: Artificial Sequence
<220> FEATURE:
<223> OTHER INFORMATION: Synthetic

<400> SEQUENCE: 65
aggagctcct gaatgaagga catcactcag ctgtgttaag tatctggaac aatactagtt    60
attaatagta atcaattacg                                                80

<210> SEQ ID NO 66
<211> LENGTH: 80
<212> TYPE: DNA
<213> ORGANISM: Artificial Sequence
<220> FEATURE:
<223> OTHER INFORMATION: Synthetic

<400> SEQUENCE: 66
gacataaaat gtaagatatg atatgctatg taagatatga tacctgcctt aaaatcaata    60
atcaatgtca acgcgtatat                                                80

<210> SEQ ID NO 67
<211> LENGTH: 80
<212> TYPE: DNA
<213> ORGANISM: Artificial Sequence
<220> FEATURE:
<223> OTHER INFORMATION: Synthetic

<400> SEQUENCE: 67
cactgcttga tacttactgt ggactttgaa aattatgaat gtgtgtgtgt gtgtctagtt    60
attaatagta atcaattacg                                                80
```

```
<210> SEQ ID NO 68
<211> LENGTH: 80
<212> TYPE: DNA
<213> ORGANISM: Artificial Sequence
<220> FEATURE:
<223> OTHER INFORMATION: Synthetic

<400> SEQUENCE: 68
caattacatt ccagtgatct gctacttaga atgcatgact gaactcctgg gtggtcaata      60
atcaatgtca acgcgtatat                                                  80

<210> SEQ ID NO 69
<211> LENGTH: 80
<212> TYPE: DNA
<213> ORGANISM: Artificial Sequence
<220> FEATURE:
<223> OTHER INFORMATION: Synthetic

<400> SEQUENCE: 69
ttattttgaa gagaaactcc tggttcccac ttaaaatcct ttcttgtttc caagctagtt      60
attaatagta atcaattacg                                                  80

<210> SEQ ID NO 70
<211> LENGTH: 80
<212> TYPE: DNA
<213> ORGANISM: Artificial Sequence
<220> FEATURE:
<223> OTHER INFORMATION: Synthetic

<400> SEQUENCE: 70
aagcagtgtg tgtttacctg catgtgtatg tgaattaact ctgttcctga ggcatcaata      60
atcaatgtca acgcgtatat                                                  80

<210> SEQ ID NO 71
<211> LENGTH: 80
<212> TYPE: DNA
<213> ORGANISM: Artificial Sequence
<220> FEATURE:
<223> OTHER INFORMATION: Synthetic

<400> SEQUENCE: 71
attgcatgtt ctcatttatt tgtgggatgt aaaaatcaaa acaatagaac gtatctagtt      60
attaatagta atcaattacg                                                  80

<210> SEQ ID NO 72
<211> LENGTH: 80
<212> TYPE: DNA
<213> ORGANISM: Artificial Sequence
<220> FEATURE:
<223> OTHER INFORMATION: Synthetic

<400> SEQUENCE: 72
ttgggaggcc gcagctggta gatcacttga ggccacgaat ttgacaccag caggtcaata      60
atcaatgtca acgcgtatat                                                  80

<210> SEQ ID NO 73
<211> LENGTH: 79
<212> TYPE: DNA
<213> ORGANISM: Artificial Sequence
<220> FEATURE:
<223> OTHER INFORMATION: Synthetic

<400> SEQUENCE: 73
```

```
atcccctgct ctgctaaaaa agaatggatg ttgactctca ggccctagtt cttgatccta    60
ttaatagtaa tcaattacg                                                 79

<210> SEQ ID NO 74
<211> LENGTH: 78
<212> TYPE: DNA
<213> ORGANISM: Artificial Sequence
<220> FEATURE:
<223> OTHER INFORMATION: Synthetic

<400> SEQUENCE: 74
ctaaagtgct gggattacag gcataagcca ccgtgcccgg ctggagcatt gggatcctat    60
taatagtaat caattacg                                                  78

<210> SEQ ID NO 75
<211> LENGTH: 75
<212> TYPE: DNA
<213> ORGANISM: Artificial Sequence
<220> FEATURE:
<223> OTHER INFORMATION: Synthetic

<400> SEQUENCE: 75
actacttaca catttcgagt tttaaataag gcgttcaata tagagtgaac acctagtcaa    60
taatcaatgt caacg                                                     75

<210> SEQ ID NO 76
<211> LENGTH: 77
<212> TYPE: DNA
<213> ORGANISM: Artificial Sequence
<220> FEATURE:
<223> OTHER INFORMATION: Synthetic

<400> SEQUENCE: 76
caggcataag ccaccgcacc cggccacccc ttactaattt ttagtaacgt cgatcctatt    60
aatagtaatc aattacg                                                   77

<210> SEQ ID NO 77
<211> LENGTH: 76
<212> TYPE: DNA
<213> ORGANISM: Artificial Sequence
<220> FEATURE:
<223> OTHER INFORMATION: Synthetic

<400> SEQUENCE: 77
ctgattgact ttgacctctg ctttccaact ttgccccaaa gaaagttagt cacctagtca    60
ataatcaatg tcaacg                                                    76

<210> SEQ ID NO 78
<211> LENGTH: 77
<212> TYPE: DNA
<213> ORGANISM: Artificial Sequence
<220> FEATURE:
<223> OTHER INFORMATION: Synthetic

<400> SEQUENCE: 78
ttcaatgaaa caagctctgt gaggctcatt tgtacccatt tgttcagta ctgcctagtc     60 aataatcaat gtcaacg                                                   77

<210> SEQ ID NO 79
<211> LENGTH: 77
<212> TYPE: DNA
```

```
<213> ORGANISM: Artificial Sequence
<220> FEATURE:
<223> OTHER INFORMATION: Synthetic

<400> SEQUENCE: 79
acatacccag agacactgag agagacagac agacagtaaa cagaggagca cgatcctatt      60
aatagtaatc aattacg                                                    77

<210> SEQ ID NO 80
<211> LENGTH: 76
<212> TYPE: DNA
<213> ORGANISM: Artificial Sequence
<220> FEATURE:
<223> OTHER INFORMATION: Synthetic

<400> SEQUENCE: 80
gctcaattgt atcttatgaa acaatttttt caaaataaaa caagagatat gatcctatta     60
atagtaatca attacg                                                    76

<210> SEQ ID NO 81
<211> LENGTH: 77
<212> TYPE: DNA
<213> ORGANISM: Artificial Sequence
<220> FEATURE:
<223> OTHER INFORMATION: Synthetic

<400> SEQUENCE: 81
cctgtgctga ataccgtctg catatgtata ggaaagggtt aactcagcag ggatcctatt      60
aatagtaatc aattacg                                                    77

<210> SEQ ID NO 82
<211> LENGTH: 77
<212> TYPE: DNA
<213> ORGANISM: Artificial Sequence
<220> FEATURE:
<223> OTHER INFORMATION: Synthetic

<400> SEQUENCE: 82
tatgtgaatg gaaataaaat aatcaagctt gttagaattg tgttcataat gacccctagtc     60 aataatcaat gtcaacg                                                    77

<210> SEQ ID NO 83
<211> LENGTH: 75
<212> TYPE: DNA
<213> ORGANISM: Artificial Sequence
<220> FEATURE:
<223> OTHER INFORMATION: Synthetic

<400> SEQUENCE: 83
gaaagtctac aattttttca gtttaaaatg gtatttattt gtaacatgta ccctagtcaa     60
taatcaatgt caacg                                                    75

<210> SEQ ID NO 84
<211> LENGTH: 77
<212> TYPE: DNA
<213> ORGANISM: Artificial Sequence
<220> FEATURE:
<223> OTHER INFORMATION: Synthetic

<400> SEQUENCE: 84
caaagatgaa ggatgagagt gacttctgcc ttcattatgt tatgtgttca tatcctagtc     60
aataatcaat gtcaacg                                                   77
```

<210> SEQ ID NO 85
<211> LENGTH: 76
<212> TYPE: DNA
<213> ORGANISM: Artificial Sequence
<220> FEATURE:
<223> OTHER INFORMATION: Synthetic

<400> SEQUENCE: 85
cagtgaatta ttcactttgt cttagttaag taaaaataaa atctgactgt gatcctatta    60
atagtaatca attacg                                                    76

<210> SEQ ID NO 86
<211> LENGTH: 76
<212> TYPE: DNA
<213> ORGANISM: Artificial Sequence
<220> FEATURE:
<223> OTHER INFORMATION: Synthetic

<400> SEQUENCE: 86
gaacagacag gtgaatgagc acagaggtca tttgtaaacc gtttgtggtt agcctagtca    60
ataatcaatg tcaacg                                                    76

<210> SEQ ID NO 87
<211> LENGTH: 79
<212> TYPE: DNA
<213> ORGANISM: Artificial Sequence
<220> FEATURE:
<223> OTHER INFORMATION: Synthetic

<400> SEQUENCE: 87 cttttggct tctgtgttta agttattttt ccctaggcc cacaaacaga gtcgatccta      60
ttaatagtaa tcaattacg                                                 79

<210> SEQ ID NO 88
<211> LENGTH: 74
<212> TYPE: DNA
<213> ORGANISM: Artificial Sequence
<220> FEATURE:
<223> OTHER INFORMATION: Synthetic

<400> SEQUENCE: 88
aaccttggaa aaattctgtt gtgtttagaa gcatgtacca atctatcact cctagtcaat    60
aatcaatgtc aacg                                                      74

<210> SEQ ID NO 89
<211> LENGTH: 76
<212> TYPE: DNA
<213> ORGANISM: Artificial Sequence
<220> FEATURE:
<223> OTHER INFORMATION: Synthetic

<400> SEQUENCE: 89
ctattcactg tctgtaggat gaaaaagtta ataccccct gagaggtttc gatcctatta     60
atagtaatca attacg                                                    76

<210> SEQ ID NO 90
<211> LENGTH: 75
<212> TYPE: DNA
<213> ORGANISM: Artificial Sequence
<220> FEATURE:
<223> OTHER INFORMATION: Synthetic

```
<400> SEQUENCE: 90
ccttagatta gtttattgta ttttttatca gctactataa ggtttacaca ccctagtcaa    60
taatcaatgt caacg                                                      75

<210> SEQ ID NO 91
<211> LENGTH: 78
<212> TYPE: DNA
<213> ORGANISM: Artificial Sequence
<220> FEATURE:
<223> OTHER INFORMATION: Synthetic

<400> SEQUENCE: 91
caagaccctc aaaattcaaa aatttccttt atcttgctgt agcacctcct gcgatcctat    60
taatagtaat caattacg                                                   78

<210> SEQ ID NO 92
<211> LENGTH: 75
<212> TYPE: DNA
<213> ORGANISM: Artificial Sequence
<220> FEATURE:
<223> OTHER INFORMATION: Synthetic

<400> SEQUENCE: 92 ggagggata ggaagggat gaggcctaac aggttgatga tctaggcttt acctagtcaa     60
taatcaatgt caacg                                                      75

<210> SEQ ID NO 93
<211> LENGTH: 77
<212> TYPE: DNA
<213> ORGANISM: Artificial Sequence
<220> FEATURE:
<223> OTHER INFORMATION: Synthetic

<400> SEQUENCE: 93
ctcaaaaagg agataattcc agcccctcgc cttaaagaat ccctatcaag tgatcctatt    60
aatagtaatc aattacg                                                    77

<210> SEQ ID NO 94
<211> LENGTH: 76
<212> TYPE: DNA
<213> ORGANISM: Artificial Sequence
<220> FEATURE:
<223> OTHER INFORMATION: Synthetic

<400> SEQUENCE: 94
cgcttgaacc tgggaggcag aggttgcagt gagccgagat cacgccgttg gatcctatta    60
atagtaatca attacg                                                     76

<210> SEQ ID NO 95
<211> LENGTH: 78
<212> TYPE: DNA
<213> ORGANISM: Artificial Sequence
<220> FEATURE:
<223> OTHER INFORMATION: Synthetic

<400> SEQUENCE: 95 ttaactttt catcctacag acagtgaata gtaaagcttt ctgtgaagac ataccctagt    60
caataatcaa tgtcaacg                                                   78

<210> SEQ ID NO 96
<211> LENGTH: 76
```

```
<212> TYPE: DNA
<213> ORGANISM: Artificial Sequence
<220> FEATURE:
<223> OTHER INFORMATION: Synthetic

<400> SEQUENCE: 96
aaattatttc ctggtgggca atattagaat atggggaatg tttgcttctg agcctagtca      60
ataatcaatg tcaacg                                                      76
```